United States Patent
Han et al.

(10) Patent No.: US 10,550,145 B2
(45) Date of Patent: Feb. 4, 2020

(54) SINGLE-STRANDED DNA NANOSTRUCTURES

(71) Applicant: President and Fellows of Harvard College, Cambridge, MA (US)

(72) Inventors: Dongran Han, Brookline, MA (US); Cameron Myhrvold, Cambridge, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 154 days.

(21) Appl. No.: 15/556,436

(22) PCT Filed: Mar. 4, 2016

(86) PCT No.: PCT/US2016/020893
§ 371 (c)(1),
(2) Date: Sep. 7, 2017

(87) PCT Pub. No.: WO2016/144755
PCT Pub. Date: Sep. 15, 2016

(65) Prior Publication Data
US 2018/0044372 A1    Feb. 15, 2018

Related U.S. Application Data

(60) Provisional application No. 62/241,821, filed on Oct. 15, 2015, provisional application No. 62/129,821, filed on Mar. 7, 2015.

(51) Int. Cl.
| | |
|---|---|
| C07H 21/04 | (2006.01) |
| C12P 19/34 | (2006.01) |
| C07H 1/00 | (2006.01) |
| C12N 15/10 | (2006.01) |
| B82Y 5/00 | (2011.01) |

(52) U.S. Cl.
CPC .............. *C07H 21/04* (2013.01); *C07H 1/00* (2013.01); *C12N 15/10* (2013.01); *C12P 19/34* (2013.01); *C12Y 207/00* (2013.01); *C12Y 301/11003* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,386,020 A | 1/1995 | Seeman et al. | |
| 6,255,469 B1 | 7/2001 | Seeman et al. | |
| 7,842,793 B2 | 11/2010 | Rothemund | |
| 8,877,438 B2 | 11/2014 | Yin | |
| 9,671,392 B2 * | 6/2017 | Jeppsen ............... | C07D 495/04 |
| 9,796,749 B2 | 10/2017 | Yin et al. | |
| 2003/0219790 A1 | 11/2003 | Seeman et al. | |
| 2006/0078910 A1 | 4/2006 | Seeman et al. | |
| 2007/0117109 A1 | 5/2007 | Rothemund | |
| 2008/0221315 A1 | 9/2008 | Garibotti et al. | |
| 2010/0216978 A1 | 8/2010 | Shih | |
| 2012/0022244 A1 | 1/2012 | Yin | |
| 2012/0251583 A1 | 10/2012 | Rothemund | |
| 2013/0316358 A1 | 11/2013 | Navon et al. | |
| 2015/0218204 A1 | 8/2015 | Yin et al. | |
| 2015/0329584 A1 | 11/2015 | Yin et al. | |
| 2017/0015698 A1 | 1/2017 | Iinuma et al. | |
| 2017/0190573 A1 | 7/2017 | Shen et al. | |

FOREIGN PATENT DOCUMENTS

| | | |
|---|---|---|
| JP | 2008-504846 A | 2/2008 |
| WO | WO 2007/012807 A2 | 2/2007 |
| WO | WO 2009/043184 A1 | 4/2009 |
| WO | WO 2009/093558 A1 | 7/2009 |
| WO | WO 2013/022694 A1 | 2/2013 |
| WO | WO 2014/018675 A1 | 1/2014 |

OTHER PUBLICATIONS

Andersen et al., Self-assembly of a nanoscale DNA box with a controllable lid. Nature. May 7, 2009;459(7243):73-6. doi:10.1038/nature07971.
Barish et al., An information-bearing seed for nucleating algorithmic self-assembly. Proc Natl Acad Sci U S A. Apr. 14, 2009;106(15):6054-9. doi: 10.1073/pnas.0808736106. Epub Mar. 24, 2009.
Bath et al., DNA nanomachines. Nat Nanotechnol. May 2007;2(5):275-84. doi:10.1038/nnano.2007.104.
Bhatia et al., Icosahedral DNA nanocapsules by modular assembly. Angew Chem Int Ed Engl. 2009;48(23):4134-7.doi:10.1002/anie.200806000.
Chen et al., DNA-directed assembly of single-wall carbon nanotubes. J Am Chem Soc. Jul. 18, 2007;129(28):8696-7. Epub Jun. 23, 2007.
Chen et al., Invadable self-assembly: combining robustness with efficiency. Proceeding SODA '04 Proceedings of the fifteenth annual ACM-SIAM symposium on Discrete algorithms. 2004:890-9.
Chworos et al., Building programmable jigsaw puzzles with RNA. Science. Dec. 17, 2004;306(5704):2068-72.
Delebecque et al., Organization of intracellular reactions with rationally designed RNA assemblies. Science. Jul. 22, 2011;333(6041):470-4. doi: 10.1126/science.1206938. Epub Jun. 23, 2011.
Dietz et al., Folding DNA into twisted and curved nanoscale shapes. Science. Aug. 7, 2009;325(5941):725-30. doi: 10.1126/science.1174251.
Douglas et al., Self-assembly of DNA into nanoscale three-dimensional shapes. Nature. May 21, 2009;459(7245):414-8.doi: 10.1038/nature08016.
Erben et al., A self-assembled DNA bipyramid. J Am Chem Soc. Jun. 6, 2007;129(22):6992-3. Epub May 15, 2007.
Fu et al., DNA double-crossover molecules. Biochemistry. Apr. 6, 1993;32(13):3211-20.
Geary et al., A single-stranded architecture for cotranscriptional folding of RNA nanostructures. Science. Aug. 15, 2014;345(6198):799-804. doi: 10.1126/science.1253920.

(Continued)

*Primary Examiner* — Robert M Kelly
(74) *Attorney, Agent, or Firm* — Wolf, Greenfield & Sacks, P.C.

(57) ABSTRACT

The present disclosure relates to nanostructures assembled from nucleic acid consisting of a single strand of DNA rationally-designed to self-assemble into a hairpin loop, helical domains, and locking domains.

15 Claims, 51 Drawing Sheets

Specification includes a Sequence Listing.

(56) References Cited

OTHER PUBLICATIONS

Han et al., DNA origami with complex curvatures in three-dimensional space. Science. Apr. 15, 2011;332(6027):342-6. doi:10.1126/science.1202998.
Han et al., Unidirectional scaffold-strand arrangement in DNA origami. Angew Chem Int Ed Engl. Aug. 19, 2013;52(34):9031-4. doi: 10.1002/anie.201302177. Epub Jul. 14, 2013.
He et al., Hierarchical self-assembly of DNA into symmetric supramolecular polyhedra. Nature. Mar. 13, 2008;452(7184):198-201. doi: 10.1038/nature06597.
Jones et al., Nanomaterials. Programmable materials and the nature of the DNA bond. Science. Feb. 20, 2015;347(6224):1260901. doi:10.1126/science.1260901. 12 pages.
Jungmann et al., DNA origami-based nanoribbons: assembly, length distribution, and twist. Nanotechnology. Jul. 8, 2011;22(27):275301. 6 pages. doi: 10.1088/0957-4484/22/27/275301. Epub May 20, 2011.
Ke et al., A study of DNA tube formation mechanisms using 4-, 8-, and 12-helix DNA nanostructures. J Am Chem Soc. Apr. 5, 2006;128(13):4414-21.
Ke, Designer three-dimensional DNA architectures. Curr Opin Struct Biol. Aug. 2014;27:122-8. doi: 10.1016/j.sbi.2014.07.010. Epub Aug. 11, 2014.
Leontis et al., Self-assembled RNA nanostructures. Science. Aug. 15, 2014;345(6198):732-3. doi:10.1126/science.1257989.
Li et al., A replicable tetrahedral nanostructure self-assembled from a single DNA strand. J Am Chem Soc. Sep. 16, 2009;131(36):13093-8. doi: 10.1021/ja903768f.
Li et al., Nucleic acid-based nanoengineering: novel structures for biomedical applications. Interface Focus. Oct. 6, 2011;1(5):702-24. doi: 10.1098/rsfs.2011.0040. Epub Jun. 28, 2011.
Linko et al., The enabled state of DNA nanotechnology. Curr Opin Biotechnol. Aug. 2013;24(4):555-61. doi: 10.1016/j.copbio.2013.02.001. Epub Apr. 6, 2013.
Liu et al., Approaching the limit: can one DNA oligonucleotide assemble into large nanostructures? Angew Chem Int Ed Engl. Mar. 13, 2006;45(12):1942-5.
Liu et al., DNA nanotubes self-assembled from triple-crossover tiles as templates for conductive nanowires. Proc Natl Acad Sci U S A. Jan. 20, 2004;101(3):717-22. Epub Jan. 6, 2004.
Marchi et al, Toward larger DNA origami. Nano Lett. Oct. 8, 2014;14(10):5740-7. doi: 10.1021/nl502626s. Epub Sep. 1, 2014.
Mitchell et al., Self-assembly of chiral DNA nanotubes. J Am Chem Soc. Dec. 22, 2004;126(50):16342-3.
Nie et al., Self-assembly of DNA nanoprisms with only two component strands. Chem Commun (Camb). Apr. 7, 2013;49(27):2807-9. doi:10.1039/c3cc39177a.
Park et al., Programmable DNA self-assemblies for nanoscale organization of ligands and proteins. Nano Lett. Apr. 2005;5(4):729-33.
Rothemund et al., Design and characterization of programmable DNA nanotubes. J Am Chem Soc. Dec. 22, 2004;126(50):16344-52. Erratum in: J Am Chem Soc. Feb. 20, 2013;135(7):2864.
Rothemund, Folding DNA to create nanoscale shapes and patterns. Nature. Mar. 16, 2006;440(7082):297-302.
Scheible et al., A compact DNA cube with side length 10 nm. Small. Oct. 21, 2015;11(39):5200-5. doi: 10.1002/smll.201501370. Epub Aug. 21, 2015.
Seeman et al., Nucleic acid nanostructures: Bottom-up control of geometry on the nanoscale. Rep. Prog. Phys, 2005, 68: 237-70.
Seeman et al., The design and engineering of nucleic acid nanoscale assemblies. Curr Opin Struct Biol. Aug. 1996;6(4):519-26.
Seeman, Nanomaterials based on DNA. Annu Rev Biochem. 2010;79:65-87. doi:10.1146/annurev-biochem-060308-102244.
Shih et al., A 1.7-kilobase single-stranded DNA that folds into a nanoscale octahedron. Nature. Feb. 12, 2004;427(6975):618-21.
Shih et al., Knitting complex weaves with DNA origami. Curr Opin Struct Biol. Jun. 2010;20(3):276-82. doi: 10.1016/j.sbi.2010.03.009. Epub Apr. 22, 2010.
Takusagawa et al., A real knot in protein. J. Am. Chem. Soc., 1996, 118 (37), pp. 8945-8946.
Taylor, A deeply knotted protein structure and how it might fold. Nature. Aug. 24, 2000;406(6798):916-9.
Tørring et al., DNA origami: a quantum leap for self-assembly of complex structures. Chem Soc Rev. Dec. 2011;40(12):5636-46. doi: 10.1039/c1cs15057j. Epub May 19, 2011.
Winfree, Algorithmic Self-Assembly of DNA. Doctoral Thesis. California Institute of Technology. May 1998. 109 pages.
Yin et al., Programming biomolecular self-assembly pathways. Nature. Jan. 17, 2008;451(7176):318-22. doi: 10.1038/nature06451.
Zhang et al., Conformational flexibility facilitates self-assembly of complex DNA nanostructures. Proc Natl Acad Sci U S A. Aug. 5, 2008;105(31):10665-9. doi:10.1073/pnas.0803841105. Epub Jul. 30, 2008.
Zheng et al., From molecular to macroscopic via the rational design of a self-assembled 3D DNA crystal. Nature. Sep. 3, 2009;461(7260):74-7. doi:10.1038/nature08274.

\* cited by examiner

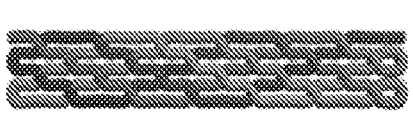 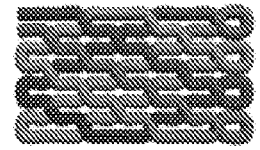
 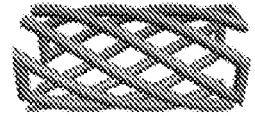
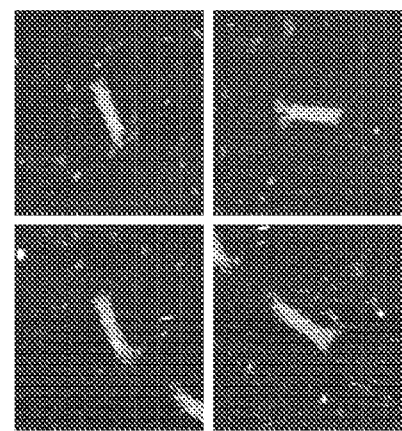
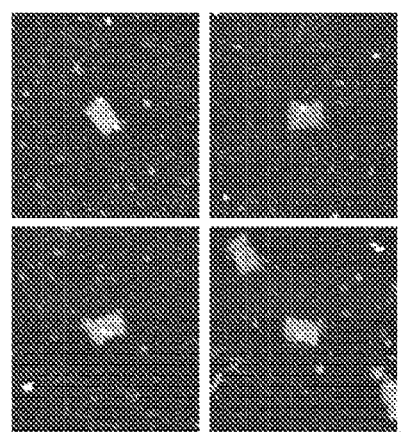
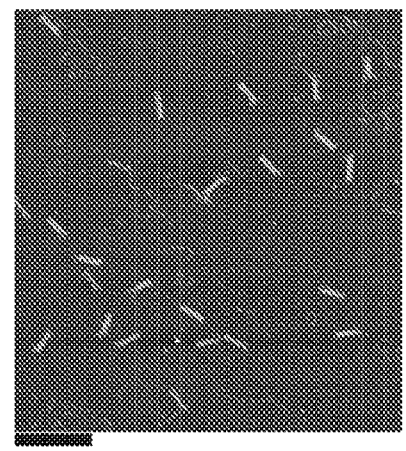
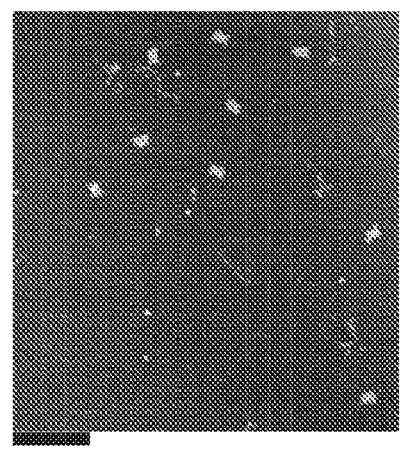
Fig. 3A            Fig. 3B

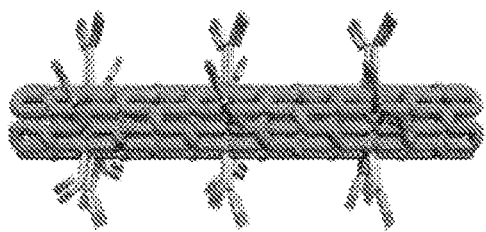 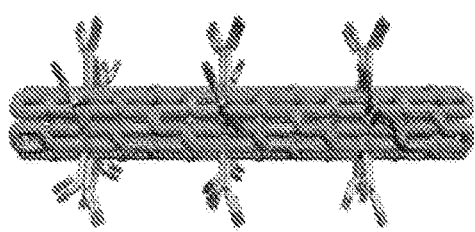
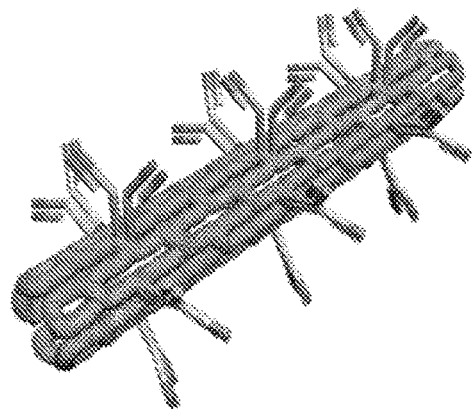 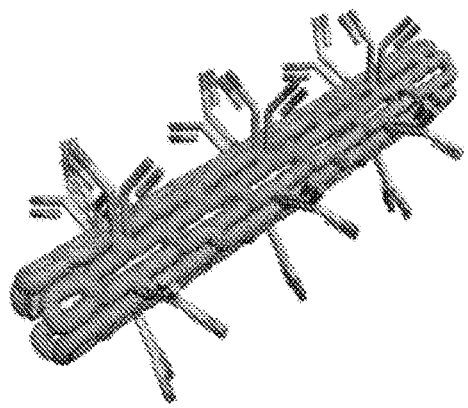
Fig. 6E                    Fig. 6F

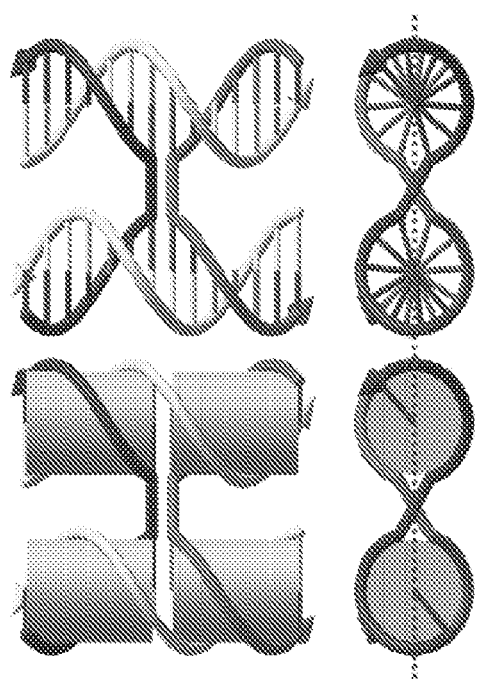 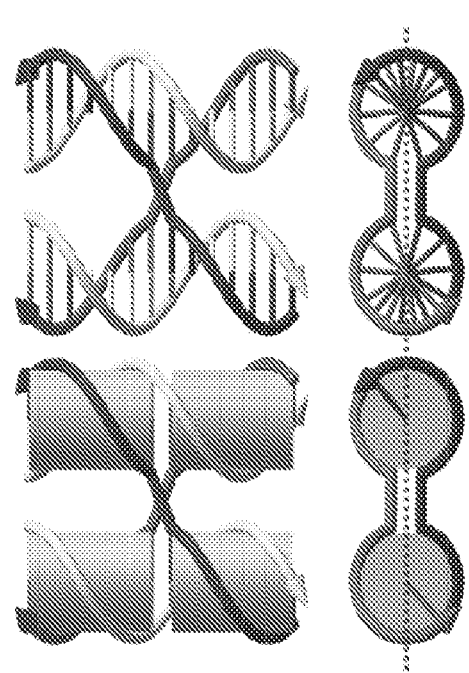
Anti-parallel crossover
Fig. 8A
Parallel crossover
Fig. 8B Helical Domain (10 bp)

Locking Domain (6 bp)

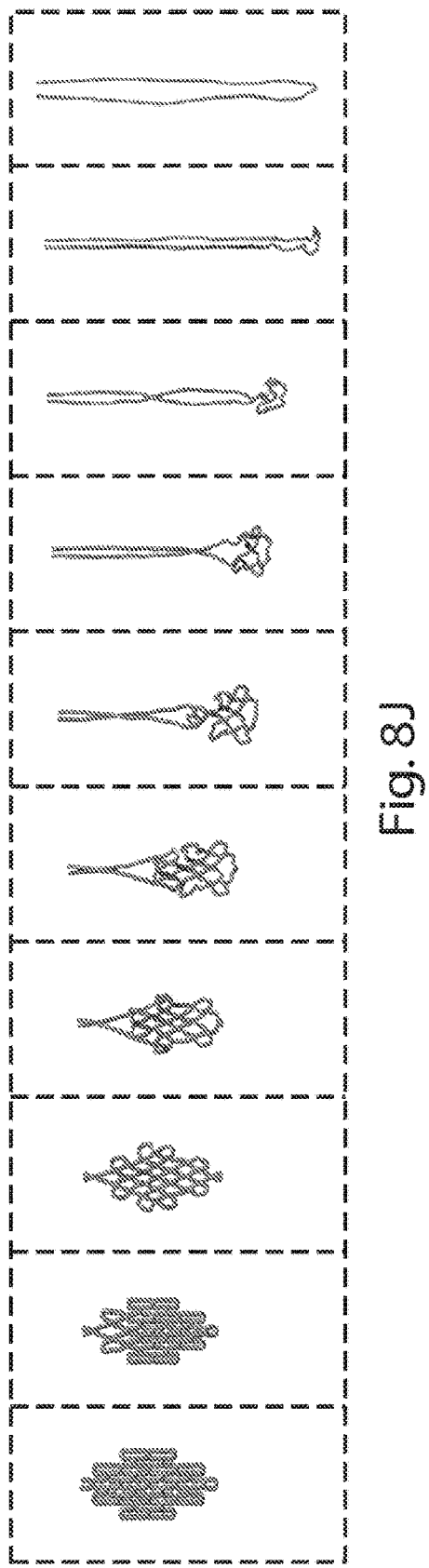

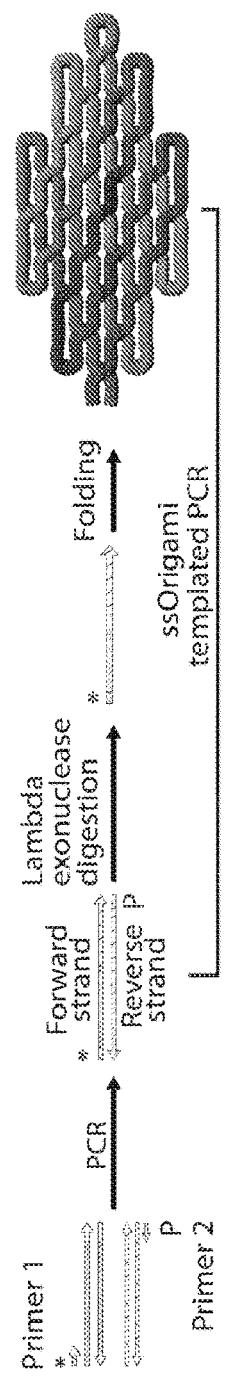

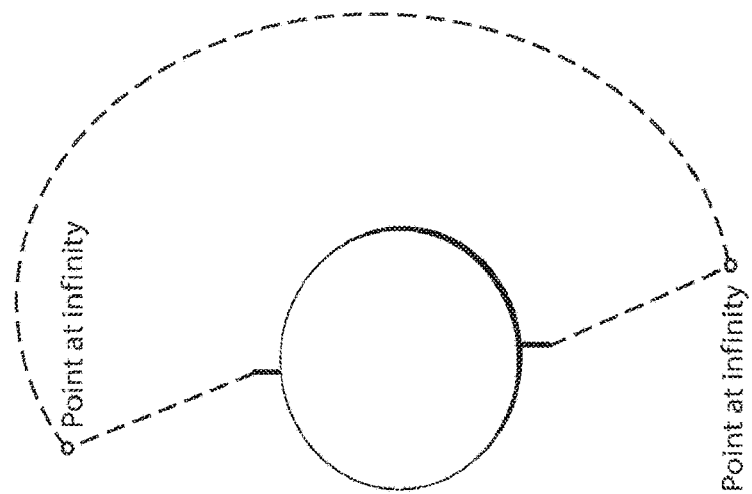
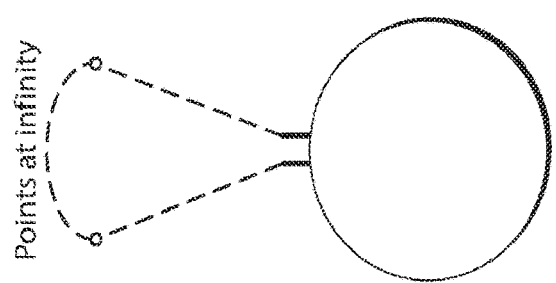
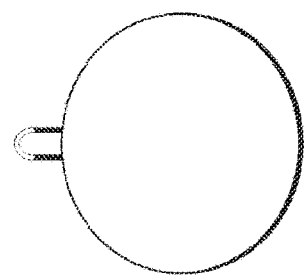
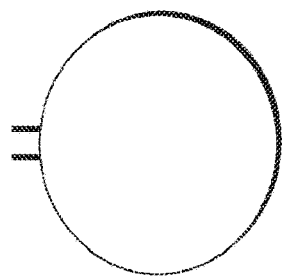
Fig. 17D
Fig. 17C
Fig. 17B
Fig. 17A

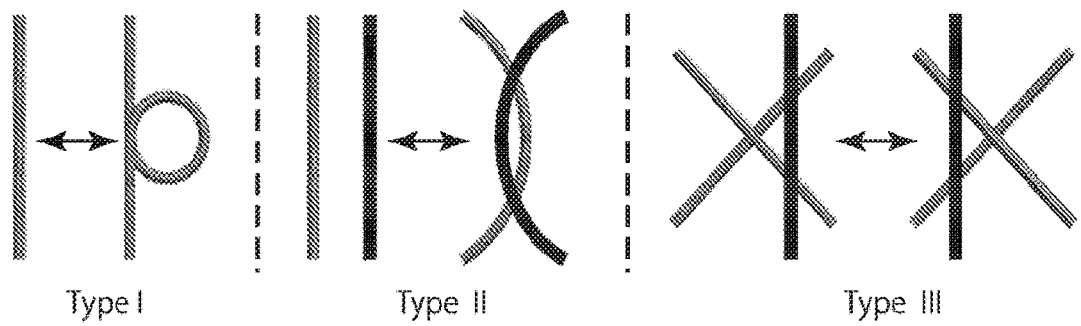
Type I  
Fig. 18A
Type II  
Fig. 18B
Type III  
Fig. 18C
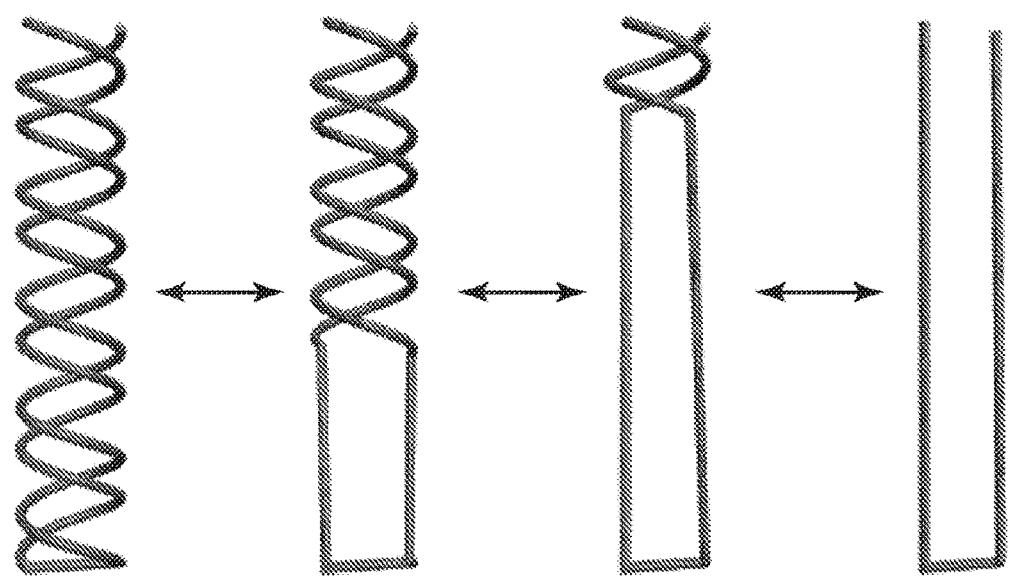
Fig. 18D Anti-parallel crossover Max-crossover design 16bp-crossover design ssOrigami crossover design

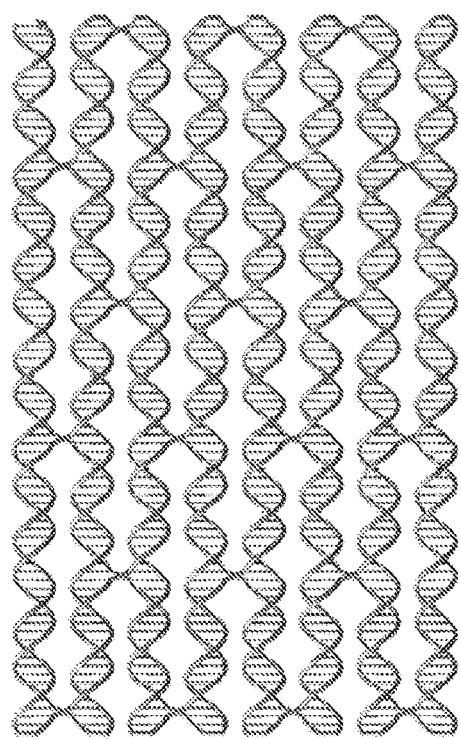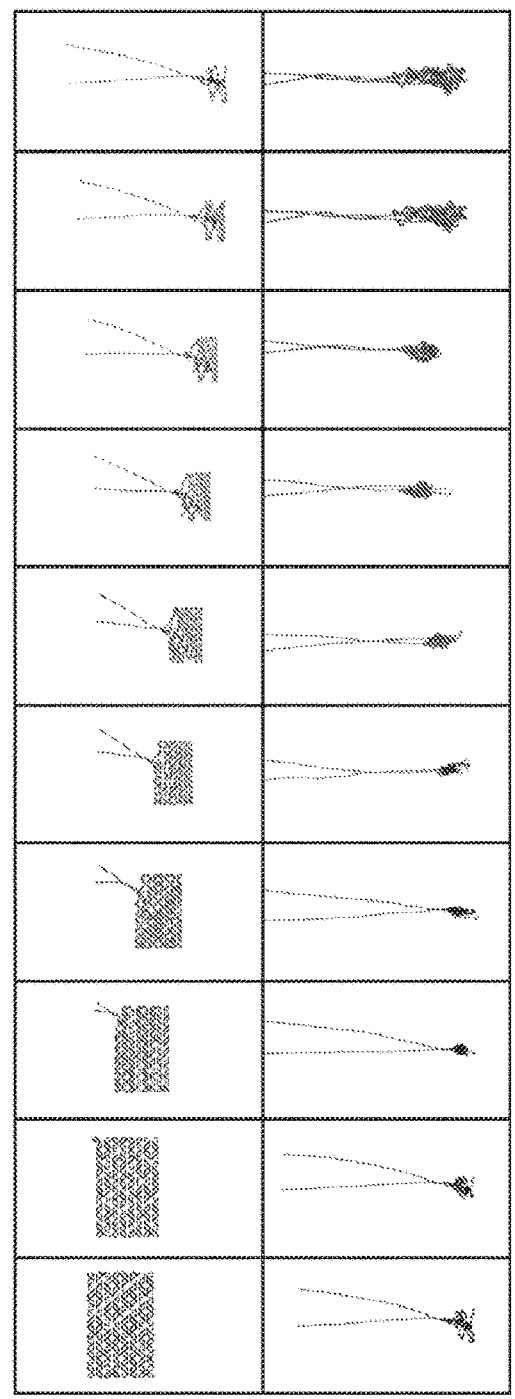
Fig. 30

SEQUENCE LISTING

<160> NUMBER OF SEQ ID NOS: 34

<210> SEQ ID NO 1
<211> LENGTH: 498
<212> TYPE: DNA
<213> ORGANISM: Artificial Sequence
<220> FEATURE:
<223> OTHER INFORMATION: Synthetic Polynucleotide

<400> SEQUENCE: 1
tacggcacgt aagccttgca ttgactagcc cggtacgtat ttcttacgca gccatgtctg    60
gcctcggacc tcagagggaa tgcgtcactt ttctttcttt ctttcttttc gaggcgtcca   120
atgattgctg tttagcaaag tggcgcacgt tgtcggcacc ctacgctttt tctttctttc   180
tttcttttcc gtctacttcc ggtaagggag acttccaagt gcgtgggttt gcgagtggcg   240
gacgctttct ttggtacgcc cgactcgcac gagatttgca acgccaatta tagcccctct   300
ccagctctgc ttttctttct ttctttcttt tgttgtcaag tttgagtaag ctggcaaact   360
ttgatggcgg acgggcaaat ccgaccgagt tttctttctt tctttctttt cgaataaaga   420
taccggtccg ggattctcga gagtcctcat gctaagaatg gcggaagcac agcgactaga   480
taatcgaccg cgtcccat                                                 498

<210> SEQ ID NO 2
<211> LENGTH: 498
<212> TYPE: DNA
<213> ORGANISM: Artificial Sequence
<220> FEATURE:
<223> OTHER INFORMATION: Synthetic Polynucleotide

```
<400> SEQUENCE: 2
acagcgacta gataatcgac cgcgtcccat gcttccgcca cagctggcat gaggacgccg      60
acgaatcccg gagttgaatc tttattcgtt ttctttcttt ctttcttttc tcggtcggaa     120
cttggcgtcc gccatagtcg tttgccagct tgccagaact tgacaacttt tctttctttc     180
tttcttttgc agagctggtg gagtgctata attgatcatt caaatctcgt tggttccggg     240
cgtaccttct ttagcgtccg ccgaaccaaa acccacgctt tgccaagtct cccttttcaac     300 aagtagacgg ttttctttct ttctttcttt tagcgtaggg ttctcgaaac gtgcgccacg     360
actctaaaca gcagcgttgg gacgcctcgt tttctttctt tctttctttt gtgacgcatt     420
actccagagg tccgagactc aacatggctg cgcagctgat acgtaccgat ccggcatcgc     480
gattcatctt cgcgaatc                                                   498

<210> SEQ ID NO 3
<211> LENGTH: 784
<212> TYPE: DNA
<213> ORGANISM: Artificial Sequence
<220> FEATURE:
<223> OTHER INFORMATION: Synthetic Polynucleotide

<400> SEQUENCE: 3
tacggcacgt aagccttgca ttgactagcc gtcgatcagt ggttatgggt ggctgcccgc      60
gggaagggat ggtaaacacg agcataacac agcgggtcgc tgtatttttct ttctttcttt    120 cttttgtttc tacaggctga gagcgtccgc cgaaccaaaa cccacgcttt gccaagtctc     180
cctttcaaca agtagacggt tttctttctt tctttctttt agcgtagggt tctcgaaacg     240
tgcgccacga ctctaaacag cagcgttggg acgcctcgat atctccctgc atactttttct    300 ttctttcttt cttttggtg ggtagttcat cgtgacgcat tactccagag gtccgagact     360
caacatggct gcgcagctga tacgtaccgt tctttgcttc cgccacagct ggcatgagga     420
cgccgacgaa tcccggagtt gaatctttat tcggccacg gaaggtgtgg tttctttctt     480
tctttctttt gaaccgcctc ccgcggctcg gtcggaactt ggcgtccgcc atagtcgttt     540
gccagcttgc cagaacttga caacttttct ttctttcttt cttttgcaga gctggtggag     600
tgctataatt gatcattcaa atctcgttgg ttccgggcgt acccggcctg gtgtatgtgt     660
tttctttctt tctttctttt tgagcacatt cgctgtaatc tcatcgccgc aatggctatg     720
ggagatatgc ataagttgcc ctaaatatag cattacagcg actagataat cgaccgcgtc     780
ccat                                                                  784

<210> SEQ ID NO 4
<211> LENGTH: 784
<212> TYPE: DNA
<213> ORGANISM: Artificial Sequence
<220> FEATURE:
<223> OTHER INFORMATION: Synthetic Polynucleotide

<400> SEQUENCE: 4
acagcgacta gataatcgac cgcgtcccat aatgctatat gatgaacaac ttatgcgtgg      60
gtcccatagc cactcagccg atgagattta ggataatgtg ctcatttct ttctttcttt     120 cttttcacat acacctgttt aggtacgccc gactcgcacg agatttgcaa cgccaattat     180
agcccctctc cagctctgct tttctttctt tctttctttt gttgtcaagt ttgagtaagc     240
tggcaaactt tgatggcgga cgggcaaatc cgaccgaggg ctcggaggcg ttcttttct     300 ttctttcttt cttttccacc cttccataac ccgaataaag ataccggtcc gggattctcg     360
```

```
agagtcctca tgctaagaat ggcggaagct tctttcggta cgtatttctt acgcagccat    420
gtctggcctc ggacctcaga gggaatgcgt cacttagggc tacccaccat tttctttctt    480
tctttctttt gtatgcaggg acccaccgag gcgtccaatg attgctgttt agcaaagtgg    540
cgcacgttgt cggcacccta cgcttttcct ttctttcttt cttttccgtc tacttccggt    600
aagggagact tccaagtgcg tgggtttgcg agtggcggac gctttgcggc tgtagaaact    660
tttctttctt tctttctttt tacagcgacc atcctagtta tgctcgaggc cgccatccct    720
tccgagccgc agccacccgt ggccactgat cgacatccgg catcgcgatt catcttcgcg    780
aatc                                                                 784
```

```
<210> SEQ ID NO 5
<211> LENGTH: 1134
<212> TYPE: DNA
<213> ORGANISM: Artificial Sequence
<220> FEATURE:
<223> OTHER INFORMATION: Synthetic Polynucleotide

<400> SEQUENCE: 5
tacggcacgt aagccttgca ttgactagcc ctcccccaca actgactgat tgctgaatct     60
tgcggtgtgt ggagttcatc tgcatcctgc ccaactccgg cggcggttgc acgatcaaca    120
ttttctttct ttctttcttt tatgaaaggc agttgggcca gtaggcggtc cacctatgag    180
caccaaagga tcctggtcgt cgggccagcc accacgtatt gctattacga ttttctttc     240 tttctttctt ttacgtatgc taactcattg ctcctaagac cagtataagt tccatggctg    300
gactccggca atgagcggga accgctgatt caacgaccag catttctttc ctttctttct    360
tttaccattc cgcgtcgagg gacgaattgg atctatctct gtgtcattct ggaccgtaag    420
cgcgcgtcag aatttgaaga ggacaatcga cgttttcttt tctttctttc ttttcgctct    480
tcaaacgagt cggttgcaat gttgcgcctc ggcgtgatcc tgcttactcg actgctctaa    540
tggacaaggc ttaaccgcgc ttcttctttt atctctcttg ttaagcagtc tgcgaaatcg    600
gggtagaacc aatgaatcct caagcactgc ccgggtagag atgagcaacc ttcttgtcct    660 tttctttct ttctttcttt ttctgaagca gactatctga cgcaggggtg gacgaaaccg    720
aggtgccgaa gacaagggct agatcggatt tctccggtcc ggatcacgcg tttttctttc    780
tttctttctt ttggacaatc agcaggatta agttcaacct tgaatcgact ccggcagcca    840
cagatctcta caggacgaac gacacctgaa ctacgctacc tcttttcttt ctttctttct    900
tttgaaagtg cttatctaga cgaaacatag cccgagccga agcgtatgtc gcgtgccccg    960
aacgcgccgt acaaccacag gttttggaaa atcttttctt tctttctttc ttttcctttc   1020
ctcaactcgt gtacgggtct aaaccatcag gacagtatga gtacaggaag ggctcgaagg   1080
catgttcagt cagtagcccc cgcaacagcg actagataat cgaccgcgtc ccat         1134
```

```
<210> SEQ ID NO 6
<211> LENGTH: 1134
<212> TYPE: DNA
<213> ORGANISM: Artificial Sequence
<220> FEATURE:
<223> OTHER INFORMATION: Synthetic Polynucleotide

<400> SEQUENCE: 6
acagcgacta gataatcgac cgcgtcccat tgcgggggct agtctttgaa catgcccaat     60
accccttcct gtgggtgtac tgtcctgatc ctctagaccc gtaccgtggg tgaggaaagg    120
ttttctttct ttctttcttt tgattttcca acgcaactgg ttgtacgaag tgctcggggc    180
```

```
acgactggta cgcttcggcg gtctttatgt ttcgtcaaga taagcacttt cttttctttc    240
tttctttctt ttgaggtagc gttttcctgg tgtcgttccc tttgtagaga tctggccaga    300
ccggagtcga cagaatgttg aacttacgca ttctgattgt ccttttcttt ctttctttct    360
tttacgcgtg atcagagcag gagaaatcca attctgccct tgtctgctca tcctcggttt    420
cagaatcccc tgcgtcattg ggcctgcttc agattttctt tctttctttc ttttaggaca    480
agaaacggct tcatctctac cccaacagtg cttgagcggt agttggttct acctcgactt    540
cgcagactca cgctcaagag agatttcttt gaaagcgcgg agcgtgcttg tccattcgga    600
ccgtcgagta agaatgcgca cgccgaggaa cctgattgca accgcccacg ttgaagagcg    660
ttttctttct ttctttcttt tacgtcgatt gtggttttca aattctggca cttgcttacg    720
gtcttcaagg acacagagaa gaattcaatt cgtcccccga tgcggaatgg tttttctttc    780
tttctttctt tttgctggtc gtctaccgag cggttccctc ggcatgccgg agtctctggc    840
tggaacttat cgacatctta ggagcaacac cctagcatac gttttctttt ctttctttct    900
tttatcgtaa tagttcgagg tggtggctga agacccgacc aggatgtcct ggtgctcata    960
ggattctcgc ctactggccg ggctgccttt cattttttctt tctttctttc ttttttgttga   1020 tcgtagccgt gccgccggag gatagtagga tgcagaagga aaccacacac cgctagattc   1080
agcaatcaaa gacttgtggg ggagatccgg catcgcgatt catcttcgcg aatc         1134

<210> SEQ ID NO 7
<211> LENGTH: 2000
<212> TYPE: DNA
<213> ORGANISM: Artificial Sequence
<220> FEATURE:
<223> OTHER INFORMATION: Synthetic Polynucleotide

<400> SEQUENCE: 7
tacggcacgt aagccttgca ttgactagcc ctttcgatcg tgttagcttt tatatcccca     60
ccactagcaa acgcgcgccg tgcggactac agaagctgag tacgagacct tgtatcctgc    120
tggtcttgca ggaggactcg tgtcatagcc gcttttttt ggccgtgact cataacttgt     180
aagaagagac tgtggtacag tgttacctac gtatgctgag tggctagttc acgccacctc    240
gggtacatgc gccccgccga gatgtagaca tctgcgtcac cgtcggcgtt agcacattct    300
accatttcac tcacaggcgc ctctcccggg tcctgtttcg tcaaggattc agggcccctt    360
cctcgtacga gagcgcaccc gcccaaccgt ggcgcgcacg gcgaagaagc ggcggcccct    420
agtcgtcatt gcaaactcta gctcgggttc tattatttcg tcatcagtag tctagtgacg    480
agtggtttgc ggcggttctc gacttgaaag ttaagattcc aacagctatt gacggtgtac    540
actctgggct gctcggctcc ccgcgagagg aaactcgttt tgtccaacgg gctgatcgct    600
cggatgcaag accgggtacc acttctgagt gtgttttaga ggtccacggc cggcgcgccg    660
gacataacgg cagtacaggc actagcgcag atgaggccct gctctacctt ggcacgcttt    720 cgtgggccg tgttaaacgg gaaaatggcc tgcgcaggtc cctgtccact atagcactcc     780
tacttacact taattttacg agatggcaag aacagatgcc aaggcttaga gtggcccgcc    840
caagggctct cgtactaggg agcggggagc agacccactc gccgctgtgc gtctgcaact    900
cagtgcgtag gatctagacc attgtccttt ggggtctacc aggggcagcc agagcggcga    960
atagaccgtt gatacgcttc tttgggacag tatcctcttg agaagtacag gcgcaatagg   1020
tcgagtggaa ccgaggtcta caaatctaat ggagaacttc tgcgcatccg gagagtgcta   1080
attgtagaca cctgatgtaa taggagggtt cgtacatcag cggctctcga cttcatacag   1140
```

```
cccaacactg ggaatcagtt ttcggaaggt ggtgaaataa ccaagcggcc acccactggc    1200
ccctaaccca agtcacggga gatgctattg caagtgtaga tgttctaccc agaccaggag    1260
cgagatggac taaaaggcgg tgttgtactt gacaatttga gcaaagcaca agttgctgct    1320
agagtacgag cgacgcttgc gcgctggaca cgacgaaaac caagcacgca ctacgacttc    1380
gccaaccgca gcagtagagg ctggcgtacg tcctacactc gcctgagagc caatcatgta    1440
ctcatggtag tcacatcaca ctattctgag cagtggccgt ttgtgacagg tgatcggcac    1500
ccctggtaca atgccagtca ccgcctggac ttggcatcga caccgggttt cacggttgcc    1560
gtataatact aacgctcgtt caggagaatc aagagtagtc tcctcggtca tcaggagggc    1620
ttgctctcca tgcaggtagc aacgctggca acaggtcccg aagtaatagc ctttggtctc    1680
aagcaggcca ggaaagatat cttgcagcag ctagcacgct tggtcctcgg gaagtgagtg    1740
tatgagtaag tacccgcaca aagctcgcga ctagtgtaat ctcttcccga tcagggaccc    1800
gggataggaa cgtctaagtg cacccggact cagtgcgtga ggacgcgtgg gcatccgtac    1860
gtttctcgct agggcttccc gctcaattaa cacccctgccg tttcggggat aattggtcta    1920
tcggcgtaag tgcctccggc agcgaccctg tatgcaaggg tacattgagc acagcgacta    1980
gataatcgac cgcgtcccat                                                2000

<210> SEQ ID NO 8
<211> LENGTH: 1970
<212> TYPE: DNA
<213> ORGANISM: Artificial Sequence
<220> FEATURE:
<223> OTHER INFORMATION: Synthetic Polynucleotide

<400> SEQUENCE: 8
acagcgacta gataatcgac cgcgtcccat tctactagat gcggcgaaac acgttcaatt      60
actatagaaa cggcaggtcc agcattgagc gggttcttct agcgagaaat aacacgatgc     120
ccacgcacga tcacgcagaa gctccgttgg gccgctgacg ttccccactt gggtccctga     180
cctgaaagag attacagtaa cggcgagctt tgaagcgtta cttactcaaa gggccacttc     240
gtgattagca tgacattgat ctgctgccca tcttcttttcc tggcaacagt gagaccaaat     300
agagttactt cgggattcac cgccagcgtt ggcgtttgca tggtgcgcta accgcctgct     360
atgacgagga cccgactctt gattctggcg cccgagcgtt agtgtgagac ggcaaccgcg     420
ctagccggtg tcgatagctt gtccagcaca aaatccttct tggcgcaggg gtgcgggcca     480
cctgtcacag gaactcactg ctcaggacta cgtgatgtga caatagtgag tacatgactc     540
gtactcaggt cagtacgcct ccgaaggttg cctctacgag aacggttggc gaacgccgag     600
tgcgtgctag cagctcgtcg tgtccgccgg gcaagcgtcg cccgcgctct agaactgtgg     660
gacccaagga acaaattgtg ctccccaaca ccgcccgcgg ttccatctcg cagtcgatct     720
gggtagactg gggacacttg caaagtcctc tcccgccaca gcccaggacc catcctgggt     780
gggtctgggg ttatttcagc ggggtccgaa aactgctggc cagtgttggg agtggtgaag     840
tcgagagccc ctgatgtacg aactacaggc catccgtatg tgtcttgagt tagcactctc     900
cgcaggagca gaagttcacc gtcagatttg tagcattgtg ttccactcga gtcactgcgc     960
ccgtcagtgg tcggtgctta ttgtcccagc gacccgtatc aacgagccac tcgccgctct    1020
ggcctaccct ggtagacccg ttaggacaat ggagaacttc ctacgcacac aattgcagac    1080
gcacaggggc gagtgggtct caagtacgct ccctagcgcg ggagcccttg gccgatcac     1140 tctaagccaa gctatctgtt cttgaagata cgtaaaatta gcccttagta ggagtgtccc    1200
```

| | |
|---|---|
| cgtggacacg aatctcgagg tacctagggc ccgttgctgg aggccccacg atgcggggcc | 1260 |
| aaggtagctg ttggcctcat ctgtgaaact gcctgtacta gttccatgtc cggcgcagcg | 1320 |
| cccgtggacc taccgcgcac actcagactg tatacccggt ctttcctgcg agcgatcagc | 1380 |
| cccaaggaca atgcgttacg atatgggaaa caagccgata ggcccagagt gtactccatt | 1440 |
| aatagctgtt gccagcttaa cttccatcct gggaaccgcc gcgctgctct cgtcactaaa | 1500 |
| tagttgatga cgaactcaca gaacccgagc ggctatttgc aatgaccgtt acgggccgcc | 1560 |
| gcaagcccgc cgtgactcta ggtccgctgc ttatgcgctc tgtgttaagg aaggggctcg | 1620 |
| ggatccttga cgaggtgaaa cccgggagac ctgaatgtga gtgaaactat tgaatgtgct | 1680 |
| aagtcgtacg gtgacgcccc cagctacatc tcgccacctc gcatgtacca caatgggcgt | 1740 |
| gaactgtcta ttcagcagga cgaggactgc cagagaacca gtctggtcgc acaagttatg | 1800 |
| acctatggcc aaaaaaccag acctatgaca cgtagcatcc tgcaagactt ctcggataca | 1860 |
| aggtttggct ctcagcttct gtcgggcgca cggcgcctac ctgctagtgg tgaagtggta | 1920 |
| aaagctaacg tcctcgaaag atccggcatc gcgattcatc ttcgcgaatc | 1970 |

<210> SEQ ID NO 9
<211> LENGTH: 1098
<212> TYPE: DNA
<213> ORGANISM: Artificial Sequence
<220> FEATURE:
<223> OTHER INFORMATION: Synthetic Polynucleotide

<400> SEQUENCE: 9

| | |
|---|---|
| tacggcacgt aagccttgca ttgactagcc aacgttttgt gccacggcgc tattgtgtcg | 60 |
| tcggtacact cgagacgtcg ccacctagag cttggaaggt atcttgtaca cagcgtaccg | 120 |
| ctgaaggcga tcgtaaggcc gaacagttat acggtgtatt cattatccga taacgagcgt | 180 |
| ttgaaccagg cagttgtaag ggttctcaat tgttacgtag cttcggcgtc cgttttttg | 240 |
| caaatagcga gctaccagtc gtagcaccga tagcgcgact ggggcagtgc tgacgcgaca | 300 |
| taaacacctt gcgctttcgt tacgttttct cggccatgtc tgacaactag gcggactaca | 360 |
| catggaattt agtaaatggc atcctgaagg cgaaataccg ccgtccagtg acgaccttga | 420 |
| tactaggtcg acctcatgag cttttttttca gttatctaga ctcaatcacc aaatattgag | 480 |
| acgaccctgc tctaatcttc ccgcggttgc atggatcgta ggttccatca cggttaatgt | 540 |
| aagggtaacc cttcgaaact gagtcggttt agttgcggct ccctcctact ctaaaccggc | 600 |
| gcctgcccca ttagcgtgat gccggcgtca ccagcatcta gtccctcgtc ttttttggg | 660 |
| tgggtcttag atgggcgcgt caattctgga acccaagcaa aatgcagcca gaactgttat | 720 |
| cgattgtcag catagttaga ctaggcaagt ttctccgtag ttaccatagg caaaataaag | 780 |
| gataatgtgg ccctccaagc tgttgggata atttcgcaca ttttaggctc aatttcgcgg | 840 |
| gtaattagag cagcttggct ttttttgcac agccgtacca ccacactccg tgcgtctgat | 900 |
| cccgcttggg tattagggcc gactgttttt gggctacaag ttatcctgat ttatcagagc | 960 |
| agaagtttat gagtcgcaag gttgtttccg aaagcgatta ccgctcgaac ccccgggacg | 1020 |
| gcattttgcg gtgtttacgc acccatgtct ttcgaagccc actgagaaac agcgactaga | 1080 |
| taatcgaccg cgtcccat | 1098 |

<210> SEQ ID NO 10
<211> LENGTH: 1098
<212> TYPE: DNA
<213> ORGANISM: Artificial Sequence
<220> FEATURE:
<223> OTHER INFORMATION: Synthetic Polynucleotide

<400> SEQUENCE: 10

| | | | | |
|---|---|---|---|---|
| acagcgacta | gataatcgac | cgcgtcccat | ttctcagtgg gcttcgaaag acatggagaa | 60 |
| ccaaacaccg | caggcgtacg | tcccgggag | agtagcggta atcgcaaata gaaacaacct | 120 |
| tgcgactcat | aaacttcttc | agtgataaat | catccgccct tgtagcccat gcaaagtcgg | 180 |
| ccctcatctt | caagcgggat | cagacgcacg | gagtgtcgtg gcacggctgt gctttttttg | 240 |
| ccaagctgct | cgacctaccc | gcgaatagga | gcctaaaatg tgcgaaatta tcccaaccgc | 300 |
| tgcgagggcc | acaggcggat | ttattttgcc | ctagttaact acggacggat atgcctagtc | 360 |
| taactatgct | gacaatctgc | tcgagttctg | gcttacgcct gcttgggtta tcggtttgac | 420 |
| gcgccagtat | tagacccacc | cttttttga | cgagggacaa tactctggtg acgccggcat | 480 |
| cacgctaatg | aacatggcgc | cggtttgttc | gaggagggag cctacaccaa accgactcta | 540 |
| tccggaaggg | ttaccttac | attaaccgtg | tgctagccta cgatccaaaa acccgcggga | 600 |
| agacgtctgc | agggtcgtct | cctaatttgg | tgattgagtc tagataactg ttttttttgct | 660 |
| catgaggtct | aattagtatc | aagaatagta | ctggacggca agatgtcgcc ttcaggatgc | 720 |
| catttactaa | actagcagtg | tagtccgcta | tggtgtcaga catcttattg aaaacgtaat | 780 |
| atttgcgcaa | ggtgtttatg | tcgcgtcagc | acatgttcag tcgcgctcca gaagctacga | 840 |
| ctggatacgc | gctatttgct | ttttttcgga | cgccgacgta tcgtaacaat tggtgcgtct | 900 |
| tacaactgcc | tggttcaaac | gctccgagca | ggataatgaa gcaactgtat aactgtaata | 960 |
| agttacgatc | gcctgctccg | gtacgctgtg | tacaagatac cttcgcagcg ctaggtggcg | 1020 |
| attagacgag | tgtaccacta | ttacaatagc | gcggtggtac aaaacgttat ccggcatcgc | 1080 |
| gattcatctt | cgcgaatc | | | 1098 |

<210> SEQ ID NO 11
<211> LENGTH: 957
<212> TYPE: DNA
<213> ORGANISM: Artificial Sequence
<220> FEATURE:
<223> OTHER INFORMATION: Synthetic Polynucleotide

<400> SEQUENCE: 11

| | | | | |
|---|---|---|---|---|
| tacggcacgt | aagccttgca | ttgactagcc | agtagtgtaa cccgtaatga cccagcctat | 60 |
| tatcgtctca | gtctgctggg | aggtcaacct | ctgcgctcta tagagtggta aaatggctcc | 120 |
| ggacagtgga | gtcagctttt | tttcaaaacc | tgcctgtccg cctactctca agttcgaatg | 180 |
| cagggattat | aggatcgttg | agataggggg | gtggaggcta tctcagtgtg ctctacgaca | 240 |
| tcagttattt | tttttttccat | aaaccagacg | ggaaggagcg tatcagaagt gggacctcct | 300 |
| tactatgcaa | cgcgctggtc | caaaattaga | ctatcagtaa cccaagaatt tgtactccaa | 360 |
| acttttttg | aatctccacc | aaattccatg | ccatgcgaga tcaatcttaa cgcagagcca | 420 |
| ctcggctgag | tgtgaacgtg | acttgcctag | actgtatcgc tttccggttt tagactttt | 480 |
| ttaggctaaa | gccgatcatc | ctccggggag | atagcacgtg gctgattaca attagtaacg | 540 |
| tcttatctag | agcactgcga | catatgaagc | gagcagatac ttgagacgtt ttttgggtg | 600 |
| aatctatctg | ccgcgctgtt | atgtatgtat | cgccggtgac cagagcgtag aagattggcc | 660 |
| gaatgcatat | aatagaaaag | taagtccata | cttatataat attttttttt gccttgctac | 720 |
| ttaccaggaa | taactaggca | aatgttaggt | acctaatcgt tctagctata atgccagtac | 780 |

| | |
|---|---|
| tactgattcg gttagagtgt agggcctcca agcttttttt ttccggtctt accctacagc | 840 |
| gctggacctg ctcacccgac cccataagaa agccttttgt ggacatgcca cccggttctg | 900 |
| atggcggcgc ctgctccctc agccatgaca gcgactagat aatcgaccgc gtcccat | 957 |

<210> SEQ ID NO 12
<211> LENGTH: 957
<212> TYPE: DNA
<213> ORGANISM: Artificial Sequence
<220> FEATURE:
<223> OTHER INFORMATION: Synthetic Polynucleotide

<400> SEQUENCE: 12

| | |
|---|---|
| acagcgacta gataatcgac cgcgtcccat catggctgag ggagcaggcg ccgccactta | 60 |
| aaccgggtgg cagccaatca aaaggcttta aaaggggggtc gggtatctcg gtccagcgct | 120 |
| ctattttaag accggatttt tttagcttgg aggaaataga ctctaaccgt accactagta | 180 |
| ctggctaaat agctagaacg attaggtacc taacattaat ttcgttattc ctgtgatcga | 240 |
| gcaaggcaat ttttttttatt atataagtcg taacttactt tttaatcgta tgcattcgtg | 300 |
| tccacttcta cgctagaccc accggcgata catacataac agcgcggggc ggagattcac | 360 |
| ccttttttttc gtctcaagtc cgccctcgct tcatatgata gagtgctcta gcttttacgt | 420 |
| tactaatcag cagcagccac gtgcccgacc cccggaggag taagtgcttt agccttttttt | 480 |
| ttgtctaaaa ccgaaaagcg atacagtcga aattagtcac gttccctatc agccgagtgg | 540 |
| ctaggcgtta agattggagc agcatggcat ggcagcacgt ggagattctt ttttttgtttg | 600 |
| gagtagtgct gctgggtta ctgtcgctct aattttgggg tctcgcgttg catagtaagg | 660 |
| aggtcccact ttaagtacgc tcctttacgg gtggtttatg gtttttttttaa taactgatgt | 720 |
| atgggagcac actggtcggg cctccacccc acactctcaa cgatcctatt taccctgcat | 780 |
| tcgaacttga gagtaggctg agaagcaggt tttgtttttt tgctgactcc attctcagga | 840 |
| gccatttaat cagtctatag agcgcctagg ttgacctcct gtaatactga gacgacgatt | 900 |
| agctgggtca tcccgtctta cactactatc cggcatcgcg attcatcttc gcgaatc | 957 |

<210> SEQ ID NO 13
<211> LENGTH: 1771
<212> TYPE: DNA
<213> ORGANISM: Artificial Sequence
<220> FEATURE:
<223> OTHER INFORMATION: Synthetic Polynucleotide

<400> SEQUENCE: 13

| | |
|---|---|
| tacggcacgt aagccttgca ttgactagcc aaagtggacg gtctttaggt tcacaacttg | 60 |
| ttggccgata ggccacacag atgttctagg cacaaggac gcaaagcgga attgggtgta | 120 |
| agccggtcgg ttcgacttta tttattttac agctttaccg gcttgatacg gccggagctc | 180 |
| cagtgctcct acttacaatg catagtcgga ttttcttaac ggagtgtttt tagaaggaaa | 240 |
| gacattagag tcgagctagt taaataggac gcaatcaccg agggcatagg ttatcgccta | 300 |
| ctttcgtgcc gagatggtcg catgaaagtg cctgctgaac tgattcagat ggtctgggtt | 360 |
| ttatttattt ccgaggctgg agcgtgaaca gcgtaaactg gttgatacct cttcgactat | 420 |
| actaacctta gaaatttcca ctccgccctc gcttttgcca tctgtagcct taggctttta | 480 |
| tttatttgca taacttgtac agaaaccatt actgctgtag ttttcatggg acgcttaggt | 540 |
| ctggcagtcg ggcgccctga gctatcacat tacgagacac gctgatggca tcctttattt | 600 |
| atttcctcat ctatccacaa gtcaacgcca ctgaatgaaa cttcaccatg gataaaatgg | 660 |

```
atgtaggcga tccgcaagta cagccccgg ccctgcgac gtgtttttg tttatttatt      720 ttcgaaaatt tgtcgcatcc ccgcgagatg tgttaaatct agcggtcggg agcttatatg    780
tcaaactagc aatctaccag ttcagttttt gttgtgggaa gggattctaa gtctgtgcct    840
cgatcatatt tagcagatag ataagtccgc cgagcaagct gacagtttag caactatgag    900
cggactcgtg ggtataggat cggacaagaa ttctttattt atttgagtgt atctagagtc    960
tcggtccggc agctccttct atgtcgtcta ccagctcacg ctggtataaa ccatggatta   1020
tctggcaatt cgcgcgccaa ggcaactcgg tttatttatt tgaacgctcg cttggcgcac   1080
ctcccgctca aatctgaccc gcgggaagat ttaccggccc tctaggtggt gatctagagc   1140
gataaaaacc ggactcttcc tgaagagttt atttattttc tatatctacg atttgaatct   1200
gagcctactc tgtaacgtga tgatgactcg agcctggctc ggaatgtgta aatttgaca    1260 gatgattctg tgacaagtta cgggtttatt tattttagca tcgcggtcac agcaccgtcc   1320
ctgacatctc attatttcca gtgagaggaa gaacgtctag aacttgcaag gagctactcc   1380
ccctcaaatc gctgggagtc ctgtaatcga tagttgacca ggattaaacg agataaaggc   1440
cctgtgccca cccctagggc gagtagaaca acgtcgagca tactcactaa tatgggcggc   1500
agtgaagttt atttatttta ctggaaatta gaggccaca atgcacactc atgaacccga   1560
gggggtcctt tttggtctgt ggtagttatg tatctcgtca actcaaataa cttaagtacg   1620
gaaatttatt tatttcactc tgagataagt ttccggcttg atccgctata tttaaccaac   1680
ttaggggctg aaagaggaat acccaatgtt ccttattcga ttgatctctt attgttcgag   1740
aacagcgact agataatcga ccgcgtccca t                                  1771
```

<210> SEQ ID NO 14
<211> LENGTH: 1804
<212> TYPE: DNA
<213> ORGANISM: Artificial Sequence
<220> FEATURE:
<223> OTHER INFORMATION: Synthetic Polynucleotide

<400> SEQUENCE: 14

```
acagcgacta gataatcgac cgcgtccat tctcgaacaa tgtgccatca atcgaaatgc      60
tcacattggc tattcctctt tcagccccta agtaggttaa atatgcatta tcaagccgga    120
taaacgtctc agagtgttta tttatttttt ccgtactcgt ttaatttgag ttgttcccat    180
acataactac cacagaccaa aaagggtgtg gtcgggttca tatataggca ttgtggcggc    240
acaatttcca gtatttattt atttcttcac tgccgcccat attagtgagt taaggagacg    300
ttgttcatcc gaccctaggg gtgagggtag ggcctttatg ggaattaatc ctggtcaact    360
atcgattaca tttatttatt tggactccca gcgcccagag ggggagtcag aagttgcaag    420
ttcgctaaat tcttcctctt cttccaaata atgagatgtc agggacggtg cacgtaccgc    480
gatgctattt atttatttcc cgtaacttgt acgtgaatca tctgcaccaa tatacacatt    540
gttcctcagg ctcgagggta gatcacgtta cagagtaggc tcagattctg ggcgtagata    600
tagatttatt tatttctctt caggaatctc acggttttta tgagtccaga tcaccaccta    660
gagggccggt aaacactggc gcgggtcagt tggtggcggg aggtgacagt cgcgagcgtt    720
ctttatttat ttccgagttg ccgactgtcg cgaattgcaa attaatccat ggtttatacc    780
agcgtgagct tcatcacgac atagaacttc tggccggacc gatgagatag atacactctt    840
tatttatttg aattcttgtc cgatcctata cccaccgctc tgctcatagt ttagacgctg    900
tcagcttagg aaccggactt atctaatttc taaatatgat cgaggcacag acttatttat    960
```

```
ttatttgaat cccttccctc tgcaaaaact gatcttcaag attgctagcc atctatataa    1020
gctcagcgtc gctagattta acacatctcg cggggagaaa caaaattttc gatttattta    1080
tttcaaaaaa cactgtttcg gggccgggga gggtgcttgc ggatccccac gatccatttt    1140
aagtcgagtg aagtttcatt cagtggcgtt gaccagagga tagatgaggt ttatttattt    1200
ggatgccatc gcgatttctc gtaatgaggc acctcagggc gcccgactgc cagacctacc    1260
gaccccatga aaccaccct agtaatggtt tgttctcaag ttatgcttta tttatttagc     1320
ctaaggcaga acatggcaaa agcacgtccg gagtggaaat ttctaaggtt agtattccat    1380
gagaggtatc atgaagatta cgctgttaat cgcccagcct cggtttattt atttacccag    1440
accatctgaa tcagttcagc tgatagtttc atgcgatttg accggcacga aacgtgggga    1500
taacctatgg acgtggtgat tgcgtcctat ttaactagct tttatttatt tcgactctaa    1560
tttttcgcct tctaaaacta tatcgttaag aaatactcgc tatgcattgt aagttggagc    1620
actggagctc cggccgtatc accccgataa agctgtattt atttatttgt cgaaccgatc    1680
ggggtacacc caattaatgc ttgcgtcctt accctctaga acatctaccc ccctatcgg     1740 ccaacaagtt gtgaacctcg aaaacgtcca ctttatccgg catcgcgatt catcttcgcg    1800
aatc                                                                 1804

<210> SEQ ID NO 15
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 15
cggtcgtcac caatatcgta attgagccaa cctcaacgcg ggtccgatgc ggcatgaggc     60
tgacacgcca tggcaggcat cgattggg                                        88

<210> SEQ ID NO 16
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 16
cccaatcgac tgaagccatg gcgtgccata ctcatgccgc aatctatccg cgttgagtta     60
gcatcaatta cgatgaaact gacgaccg                                        88

<210> SEQ ID NO 17
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 17
aaacagatcg cactcagcgg tctcgtagat cgagtgtctc tacctgagac aaggatctgt     60
ttcacaaggc cttgtgactt ccgctagtc                                       89

<210> SEQ ID NO 18
<211> LENGTH: 88
<212> TYPE: DNA
<213> ORGANISM: Artificial Sequence
<220> FEATURE:
<223> OTHER INFORMATION: Synthetic Polynucleotide
```

<400> SEQUENCE: 18
cctcgaagtg attgatctag cgtaggctct accgttcggc tcgccctctg caacatgaag    60
atcggtcgcc aagcaccgat gtcggtcc    88

<210> SEQ ID NO 19
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 19
ggaccgacag gttgtcttgg cgacctcgtc ccatgttgca gagtgtgagc cgaacggaaa    60
taactacgct agactcagga cttcgagg    88

<210> SEQ ID NO 20
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 20
gactagcgga aatggcaagg ccttgtattg gagatccttg ttcaatctag agacactcgc    60
gccacgagac cgcagagcac gatctgttt    89

<210> SEQ ID NO 21
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 21
ccggctgtgg gcgcgaggtg ccgtggcgtc tgcaagacac agcgctctgt tgatatcgcc    60
caggtctacg acagttgagt gttgggcg    88

<210> SEQ ID NO 22
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 22
cgcccaacac tgggttgtcg tagacaaaat cgatatcaac aataaggtgt gtcttgccca    60
gtacacggca cctcgatctc acagccgg    88

<210> SEQ ID NO 23
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 23
tcatagtaaa gacgtcagga tagaatactg ggaagatgcc attatttccc atatgtttgc    60
taatcgtgga ctccacgtca tggcagcc    88

<210> SEQ ID NO 24
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 24
caggatctag tgctctatgg gattaggtct aggaccttcc ggcgggtcgg tttgtgcata    60
ccagatgtta acgtgaccgg cagtcaagt                                      89

<210> SEQ ID NO 25
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 25
acttgactga ggcacacgtt aacattcgca ttgcacaaac ccacacaccg gaaggtcacg    60
tctctaatcc cattgagtgc tagatcctg                                      89

<210> SEQ ID NO 26
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 26
ggctgccatg agaccgagtc cacgagttgg caacatatgg gtagagctgg catcttcaga    60
cgcttctatc ctgctagact tactatga                                       88

<210> SEQ ID NO 27
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 27
cagatcatct gtgtgtggcc ggatgcctta tcgggtctcg tcacactcgg gcacagaata    60
gatctctaag agacacgtgc ccaaagcg                                       88

<210> SEQ ID NO 28
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 28
cgctttgggc cacgctctct tagagtcgga ctctgtgccc gagggcgacg agacccggag    60
cgccatccgg ccagacccgg atgatctg                                       88

<210> SEQ ID NO 29
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 29
gggacgtgca tgcgacccac gtcgtgattt tgttccactt gggacgaatg tcgaagtgta    60
tggtgcatta cccgtaggct acatctgg    88

<210> SEQ ID NO 30
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 30
ccagatgtaa gttttgggta atgcatcagc cacttcgaca tgatcttcaa gtggaacctg    60
ggcacgacgt gggctggtag cacgtccc    88

<210> SEQ ID NO 31
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 31
ctgataggcc catttctaat ttcgcggtct cttacacggg tgcgtggtct tcctctgaaa    60
actggagcca cagggaggga cactcgctt    89

<210> SEQ ID NO 32
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 32
aagcgagtgt cggcatctgt ggctccgcct accagaggaa gacacgtgac ccgtgtaaga    60
cgtggcgaaa ttagaagtca gcctatcag    89

<210> SEQ ID NO 33
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 33
caggctcgtg tgccttggag atggaaccca gctggagcga gacaaccaga tgggatcctt    60
cagcccatga caaatgccgc acaggcagc    89

<210> SEQ ID NO 34
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 34
gctgcctgtg ccctccttgt catgggtgcc tggatcccat cttcggtgct cgctccagct    60
caactccatc tccaccggtc acgagcctg    89

SINGLE-STRANDED DNA NANOSTRUCTURES

RELATED APPLICATIONS

This application is a national stage filing under 35 U.S.C. § 371 of international application number PCT/US2016/020893 filed Mar. 4, 2016, which claims the benefit under 35 U.S.C. § 119(e) of U.S. provisional application No. 62/129,821 filed Mar. 7, 2015 and U.S. provisional application No. 62/241,821 filed Oct. 15, 2015, each of which is incorporated by reference herein in its entirety.

FEDERALLY SPONSORED RESEARCH

This invention was made with government support under N00014-11-1-0914 and N00014-13-1-0593 awarded by the U.S. Department of Defense. The government has certain rights in this invention.

BACKGROUND OF INVENTION

Deoxyribonucleic acid (DNA) has been used to create a variety of complex nanoscale-sized structures since the conception of DNA nanotechnology in 1982. The process of producing nucleic acid nanostructures typically involves folding of a long single strand of viral DNA aided by multiple smaller "staple" strands. These shorter staple strands bind the longer strand in various locations, resulting in the formation of an arbitrary two-dimensional or three-dimensional nanostructure.

SUMMARY OF INVENTION

Well-defined biological structures typically form in nature from a single polymer of a macromolecule, such as messenger ribonucleic acid (mRNA) and protein. The production of such well-defined structures from a single polymer of DNA, however, does not occur in nature and is particularly challenging. Existing technologies for producing DNA nanostructures, such as "DNA origami," relies on the use of multiple (e.g., hundreds) of DNA "staple" strands to direct the folding of and to hold the shape of a long single-stranded scaffold strand. Such staple strands are artificially synthesized (e.g., using a computerized synthesizer), and as a result, are expensive (e.g., ~$6,000/g before purification and ~$400K/g after purification) and prone to synthesizing error in their sequences. Approximately 90% of nanostructures formed using staple strands contain "gaps" in their structure as a result of missing staple strands and/or are contaminated with nucleotide sequences containing errors that were not intended for inclusion in the final nanostructure. Such impurities can be particularly problematic for therapeutic applications, where the purity of the nanostructure is critical.

Provided herein are methods that enable robust assembly and replication of two- and three-dimensional nucleic acid nanostructures using a single strand (one molecule) of nucleic acid, without the use of contaminating staple strands. Generally, a single strand of nucleic acid is rationally designed to fold into an arbitrary user-defined shape using only simple base pairing rules through intrinsic self-complementarity, which guides the nucleic acid folding process, negating the need for multiple shorter strands. More specifically, using this unimolecular folding process, a single strand of nucleic acid of the present disclosure is rationally designed to assemble into a "chain" that includes a hairpin loop as well as paired regions (e.g., "helical domains") and unpaired regions (e.g., "locking domains"), which direct the nucleic acid chain to further assemble into the final nanostructure. The methods provided herein result in nanostructures having high structural complexity while maintaining knotting simplicity (unknotted), component simplicity and homogeneity (one single strand of DNA). These features enable, for example, high purity and large-scale synthesis of DNA nanostructures for diverse applications in fields, such as photonics, materials and therapeutics.

Thus, aspects of the present disclosure provided nanostructures formed from nucleic acid consisting of a single strand of DNA rationally designed to self-assemble into a hairpin loop, helical domains, and locking domains. That is, the nucleic acid component of the nanostructure is a single strand of DNA that is designed to fold into a nanostructure, which is held together solely by intrinsic complementarity-unpaired regions of the DNA strand bind ("hybridize") to other unpaired regions of the same strand to form complementary paired regions. Additional nucleic acids strands are not required, and are not used, to produce a nanostructure from a single strand of DNA, as provided herein.

Also provided herein is a single strand of DNA rationally-designed to self-assemble into a nanostructure containing a hairpin loop, helical domains, and locking domains.

While DNA-based nanostructures are described throughout the present disclosure, the invention is not limited to DNA. A single strand of RNA may also be used to form a nanostructure of the present disclosure. Thus, the present disclosure contemplates a single strand of RNA rationally designed to self-assemble into a hairpin loop, helical domains, and locking domains. The present disclosure also contemplates nanostructures formed from a nucleic acid consisting of a single strand of RNA rationally-designed to self-assemble into a hairpin loop, helical domains, and locking domains.

A single strand of DNA of the present disclosure is rationally designed to fold back on itself to form a partially paired "chain" containing a hairpin loop. This partially paired chain further assembles to form a nanostructure containing helical domains and locking domains. FIG. 1 illustrates an example of a self-assembly process of the present disclosure—schematics of a chain are shown at the bottom of the figure. A "paired" region of a chain is formed by one region of the single strand of DNA binding to another, complementary, region of the DNA (FIG. 2A(i).

A "helical domain," as used herein, refers to a paired region of a single strand of DNA, or more specifically, a paired region of a DNA chain. An example of a helical domain is illustrated in FIG. 2A(i). A helical domain forms at least one 10.5 nucleotide helical turn. Helical domains are discussed in more detail below.

A "locking domain," as used herein refers to an unpaired region of a single strand of DNA, or more specifically, an unpaired region of the DNA chain. An example of a locking domain is illustrated in FIG. 2A(ii). The unpaired region refers to the relationship between the regions of the single strand of DNA that lie in the same layer/plane (e.g., FIG. 2A(ii), dark gray strands). Single-strand regions of locking domains of one layer pair with single-strand regions of locking domains of another layer to "lock" the layers together. Locking domains are discussed in more detail below.

In some embodiments, a nanostructure comprises a first layer containing helical domains and locking domains, wherein at least two helical domains of the first layer are separated from each other by a locking domain, and a second layer comprising helical domains and locking domains, wherein at least two helical domains of the second layer are separated from each other by a locking domain, wherein a locking domain of the first layer is hybridized to a locking domain of the second layer.

In some embodiments, a single strand of DNA has a length of 500 nucleotides to 10,000 nucleotides. For example, the a strand of DNA may have a length of 2,000 nucleotides to 5,000 nucleotides. In some embodiments, a single strand of DNA has a length of 4000 nucleotides In some embodiments, helical domains have a length of 10 to 50 nucleotides. For example, helical domains may have a length of 10 to 30 nucleotides. In some embodiments, helical domains have a length of 10 nucleotides.

In some embodiments, the locking domains have a length of 4 to 20 nucleotides. For example, the locking domains may have a length of 5 to 10 nucleotides.

In some embodiments, the locking domains have a length of 6 nucleotides.

In some embodiments, a nanostructure further comprises loop domains that connect one helical domain to another helical domain and are located along the periphery of the nanostructure. In some embodiments, the loop domains have a length of 10 to 100 nucleotides. For example, the loop domains may have a length of 10 to 50 nucleotides. In some embodiments, the loop domains have a length of 20 nucleotides.

In some embodiments, the crossing number of the nanostructure is zero and the nanostructure is unknotted.

In some embodiments, the nanostructure contains only parallel crossovers.

In some embodiments, the nanostructure contains continuous π-π stacking along greater than 50% (e.g., greater than 60%, greater than 70%, greater than 80%, greater than 85%, greater than 90%, greater than 95%, or greater than 98%) of the helical domains of the nanostructure.

Some aspects of the present disclosure provide compositions comprising nanostructures, as provided herein.

Other aspects of the present disclosure provide methods of producing nano structure, as provided herein. In some embodiments, the methods comprise incubating a single strand of DNA of the present disclosure under conditions that result in the formation of a nanostructure.

In some embodiments, methods of producing a nanostructure comprise (a) combining in a single reaction mixture (i) a first DNA template and a second DNA template, wherein the templates comprise end sequences that overlap with each other, (ii) a first primer having a phosphorothioate modification, wherein the first primer binds to the end of the first DNA template that is opposite to the overlapping end sequences, (iii) a second primer having a phosphate modification, wherein the second primer binds to the end of the second DNA template that is opposite to the overlapping end sequences, and (iv) polymerase, (b) performing on the single reaction mixture a nucleic acid amplification reaction, thereby producing amplified DNA, (c) exposing the amplified DNA to exonuclease (e.g., lambda exonuclease) digestion, thereby producing a single strand of DNA, and (d) heating the single strand of DNA to a temperature of 85° C. to 95° C., and then progressively cooling the single strand of DNA to a temperature of 20° C. to 37° C., thereby producing the nanostructure.

Also provided herein are methods of producing a single strand of DNA of the present disclosure. In some embodiments, the methods comprise (a) combining in a single reaction mixture (i) a first DNA template and a second DNA template, wherein the templates comprise end sequences that overlap with each other, (ii) a first primer having a phosphorothioate modification, wherein the first primer binds to the end of the first DNA template that is opposite to the overlapping end sequences, (iii) a second primer having a phosphate modification, wherein the second primer binds to the end of the second DNA template that is opposite to the overlapping end sequences, and (iv) polymerase, (b) performing on the single reaction mixture a nucleic acid amplification reaction, thereby producing amplified DNA, and (c) exposing the amplified DNA to exonuclease (e.g., lambda exonuclease) digestion, thereby producing a single strand of DNA.

In some embodiments, the single strand of DNA is heated for 1 min to 15 min, and then cooled for 90 min to 180 min. For example, the single strand of DNA may be heated for 10 min, and then cooled for 120 min.

BRIEF DESCRIPTION OF DRAWINGS

FIG. 2A, bottom panel, is a simplified cartoon model of an example of a ssDNA nanostructure of the present disclosure.

FIGS. 3A-3E, depict different geometries of a ssDNA of the present disclosure. FIG. 3A shows a strip shape ssDNA of the present disclosure (2,166 nt). FIG. 3B shows a rectangle shape ssDNA of the present disclosure (1,884 nt). FIG. 3C shows a triangle shape ssDNA of the present disclosure (3,439 nt). FIG. 3D shows a rhomboid shape ssDNA of the present disclosure (3,940 nt). The top panels of FIGS. 3A-3D show pipeline style models of ssDNA nanostructures, highlighting the folding track of the putative partially-paired intermediate. The middle panels of FIGS. 3A-3D present 3D perspectives of the pipeline style models of the corresponding designs of the ssDNA nanostructures above. The bottom panels of FIGS. 3A-3D show atomic force microscopy (AFM) images, zoomed-in (top) and zoomed-out (bottom). FIG. 3E is a dynamic relaxation model showing the relaxation process of a triangle-shaped ssDNA nanostructure (FIG. 3C) under gravity with both of its ends fixed.

FIG. 4A shows a 3×3 ssDNA nanostructure containing 966 nt. FIG. 4B shows a 4×4 ssDNA nanostructure containing 1,538 nt. FIG. 4C shows a 5×5 ssDNA nanostructure containing 2,238 nt. Pipeline style models are shown in the top row. Zoomed-in and zoomed-out AFM images are shown in the middle and the bottom rows, respectively.

FIGS. 6A-6F show examples of three-dimensional ssDNA nanostructures containing different therapeutic stimulatory agonist antibodies and therapeutic inhibitory antibodies (e.g., ipilimumab/nivolumab).

FIGS. 8A-8J show design principles for ssDNA nanostructures of the present disclosure. FIGS. 8A and 8B are schematics of the anti-parallel crossover designs (FIG. 8A) and the parallel crossover designs (FIG. 8B), illustrating their local topology. The dashed lines denote the plane containing all DNA helical axes. FIGS. 8C-8E show models of a typical putative double-stranded intermediate for ssDNA nanostructures. FIGS. 8F-8H depict models of a fully formed ssDNA nanostructure. FIGS. 8C and 8F show double helical models with cylinders depicting the unperturbed base pairs. FIGS. 8D and 8G are carton models highlighting the 10-bp helical domains (rectangles) corresponding to the white cylinders in FIGS. 8C and 8F, and 6-bp locking domains (crosses) corresponding to the gray cylinders in FIG. 8F. Bottom-layer strand sections and rectangles are colored in gray and the top-layer ones are colored in black, while the lines denote the connection between the two layers in FIGS. 8C, 8D, 8F, and 8G. FIGS. 8E and 8H show pipeline style models representing the folding track of the double-stranded intermediate. FIG. 8I is a schematic depicting the formation of a locking domain. FIG. 8J is a dynamic relaxation model showing a time lapse snapshots of the relaxation process of an ssDNA nanostructure pipeline model (FIG. 8H) under simulated gravity with both of its ends fixed.

FIGS. 9A-9E show schematics of a process for synthesizing a ssDNA nanostructure of the present disclosure by in vitro PCR (FIGS. 9A-9D). FIG. 9A shows a one-step PCR reaction using two double-stranded GBLOCK® templates (double-stranded, sequence-verified genomic blocks) containing 30 bp sequence overlap and two modified primers (phosphorothioate modification on one primer and phosphorylation modification on the other primer). FIG. 9B shows a double-stranded PCR product with modified 5' ends. FIG. 9C depicts a ssDNA product after Lambda exonuclease digestion. Phosphorothioate modification protects the forward strand from being digested. FIG. 9D shows an example of a folded ssDNA nanostructure. Note that the folded ssDNA nanostructure can be directly used as a template for its replication. FIG. 9E shows an AFM image of 5×5 ssDNA nanostructures produced by an in vitro PCR method (second cycle). Scale bar in FIG. 9E: 200 nm. Zoomed-in image size: 100 nm×100 nm.

FIG. 14A shows an example of a typical one touch drawing shape. FIGS. 14B-14D show an example of a shape that cannot be drawn with one touch drawing unless extra bridging (nucleic acid) segments are introduced (FIG. 14D).

FIGS. 17A-17D show the conversion of the knot diagram of an open-ended biological macromolecule into a closed loop. FIG. 17A shows a linear macromolecule with exposed ends that are close to each other. FIG. 17B shows that the direct connection of the open ends in FIG. 17A without intersecting with the remaining part of the knot diagram results in a closed loop. In FIGS. 17C-17D, if each of the two ends of an open-chain molecule can be connected to a point at infinite distance via a straight line segment that does not intersect the remaining part of the 2D diagram, the two points can then be connected at infinite distance and the open-chain molecule can be converted into a closed loop while preserving its knotting complexity.

FIGS. 18A-18D show Reidemeister moves (FIGS. 18A-18C) and an example of Reidemeister moves operation over a DNA hairpin (FIG. 18D). FIG. 18A shows a Type I Reidemeister move: twist and untwist in either direction. FIG. 18B depicts a Type II Reidemeister move: move one strand completely over another. FIG. 18C shows a Type III Reidemeister move: move a strand completely over or under a crossing. FIG. 18D shows a DNA hairpin structure being converted through continuous Type I Reidemeister moves to an unknotted open loop.

FIG. 26D can be viewed as a top-down projection of the molecule on to this horizontal plane. Side view (FIG. 26G) and top view (FIG. 26F) of 16S rRNA with a different falling direction. Considering the top-down projection of the molecule on the horizontal planes contains closed loops surrounding the red spheres (indicated by red circles), such falling direction is not permitted.

FIG. 29A shows a maximum crossover design in which parallel crossovers are created in all possible positions. Black strands are always on top of the gray strands at crossover positions. This design contains sets of 5, 4, and 1 unperturbed base pairs; there are no helical domains present in this structure. FIG. 29B shows a 16 bp-crossover design which contains only 16 unperturbed base pairs between adjacent parallel crossovers. The light gray strands do not travel between adjacent helices. FIG. 29C shows the final ssDNA nanostructure crossover design, in which local interlocks occur only between strands with the same color (at the helical domain positions). Top: 3D double helical model. Bottom: double helical model with wrapped cylinder showing the unperturbed base pairs.

FIG. 30 provides selected screenshots of a dynamic knot relaxation process of a parallel ssDNA nanostructure with a 16 bp crossover distance.

DETAILED DESCRIPTION OF INVENTION

Figure 1:
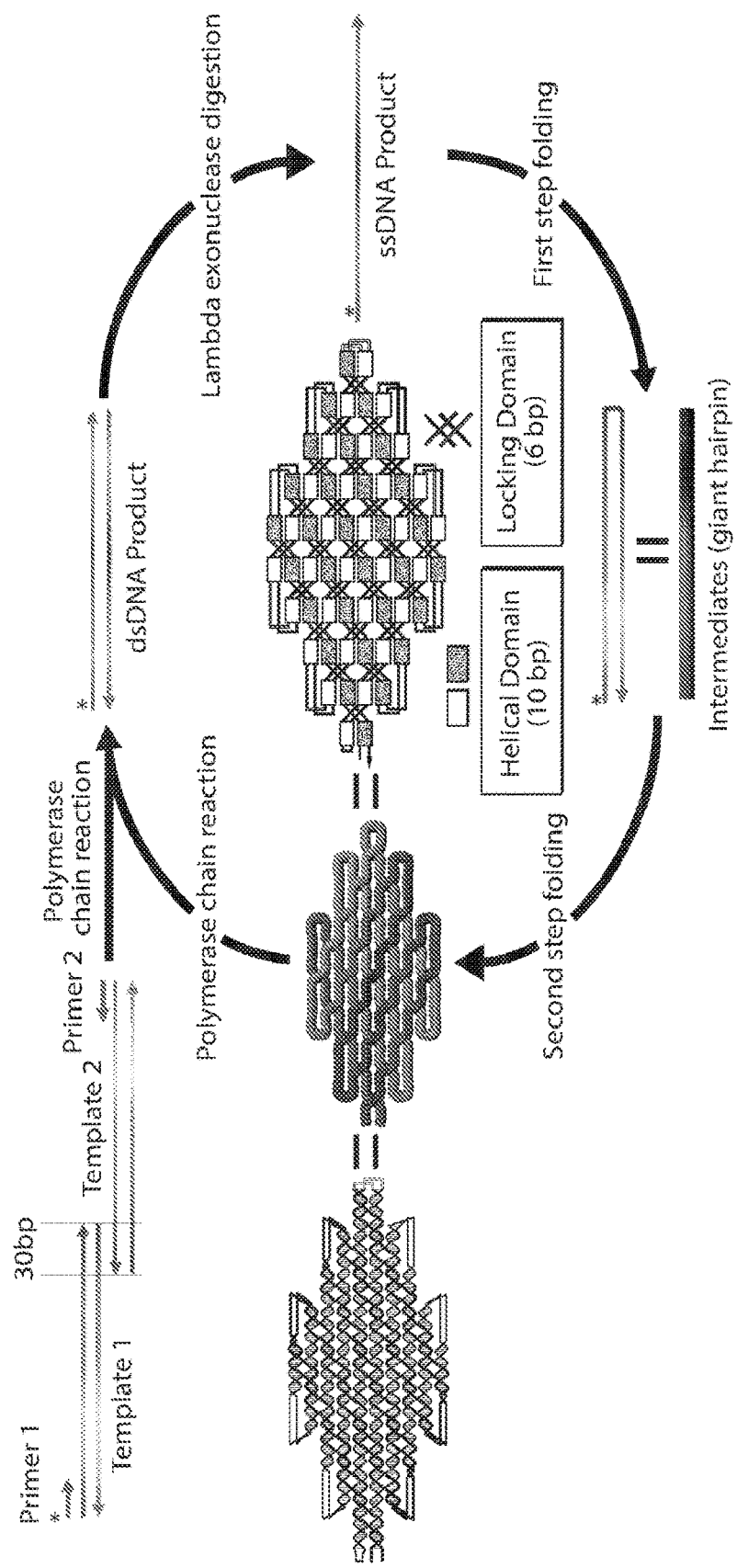
FIG. 1 is a schematic showing an example of a method for synthesis, self-assembly and replication of a single-stranded DNA (ssDNA) nanostructure of the present disclosure.

Provided herein is a design and synthesis framework for folding single-stranded (ss) nucleic acid (e.g., multi-kilobase ssDNA) into a user-prescribed shape. The methods of the present disclosure, in some embodiments, employ partially complementary double-stranded nucleic acid (e.g., DNA) configurations and parallel crossovers (see, e.g., Seeman et al. *Current Opinion in Structural Biology*, 6(4), 519-526, 1996; and Han et al. *Angewandte Chemie International Edition*, 52(34), 9031-9034, 2013) to construct nanostructures having high structural complexity, folded from a single strand of nucleic acid (e.g., DNA). The single-stranded nucleic acid nanostructures are particularly advantageous for use in biomedical applications, for example. Unlike existing multi-strand nucleic acid nanostructures, which contain hundreds of distinct components with undesirable defects and heterogeneity, the nanostructures of the present disclosure are homogenous 'pure' structures (having only one nucleic acid component as the base structure—a single strand of DNA), which is important for meeting quality control standards set by regulatory agencies, such as the U.S. Food and Drug Administration (FDA). Further, the cost of producing the nucleic nanostructures in accordance with the present disclosure is much less than that of existing technologies, particularly because the nanostructures provided herein are self-assembled from a single molecule of DNA, rather than from hundreds of different synthetic DNA strands.

Many biological macromolecules, such as mRNAs and proteins, fold from covalently linked polymers into well-defined structures, yet forming DNA nanostructures via unimolecular folding is challenging, in part, due to intrinsic topological or kinetic traps present in the final structure. The present disclosure provides a platform for the self-assembly of a single strand of DNA into a two- or three-dimensional nanostructure.

It should be understood that while the nanostructures themselves (the base structure) typically consist of a single strand of DNA folded into a desired shape, the nanostructures may comprise agents or other molecules that are added to or attached to the folded nanostructure, as described elsewhere herein. For example, in some embodiments, ssDNA nanostructures of the present disclosure are decorated with therapeutic moieties (e.g., antibodies) or other molecules, such as fluorophores, which may be attached to the nanostructures through single-stranded "handles" and "antihandles" (short, e.g., 5 to 50 nt single-stranded nucleic acids: a handle is at least partially complementary, and may be wholly complementary, to an antihandle). Other means of attaching molecules to the nanostructures are contemplated herein. Such handles and antihandles, and other attachment moieties, are not required to maintain the structural integrity of the ssDNA nanostructure.

Nanostructures of the present disclosure form from a single strand of DNA rationally-designed to "self-assemble" into a hairpin loop, helical domains, and locking domains. Thus, nanostructures of the present disclosure may be referred to as "single-stranded DNA (ssDNA) nanostructures." "Self-assembly," as used herein, refers to the ability of a single-strand of nucleic acid to anneal to itself, in a sequence-specific manner, in a predicted manner, and without external physical control. The fundamental principle for designing a self-assembled ssDNA nanostructure, as provided herein, is that sequence complementarity in the DNA strand is encoded such that, by pairing up complementary regions (referred to herein as "self-complementarity"), the DNA strand self-organizes into a predefined nanostructure under appropriate physical conditions (e.g., temperature, time, buffer). In some embodiments, this annealing process involves placing the single strand of DNA at an elevated temperature (e.g., 80 to 95° C.) and then reducing the temperature gradually (e.g., to a temperature of 20 to 37° C.) in order to favor sequence-specific binding. It should be understood that a ssDNA nanostructure of the present disclosure self-assembles from a single strand of DNA, without the help of other nucleic acids, such as shorter nucleic acid "staple" strands. The nucleic acid used to form a nanostructure, as provided herein, consists solely of a single contiguous strand of DNA.

Figure 2A:
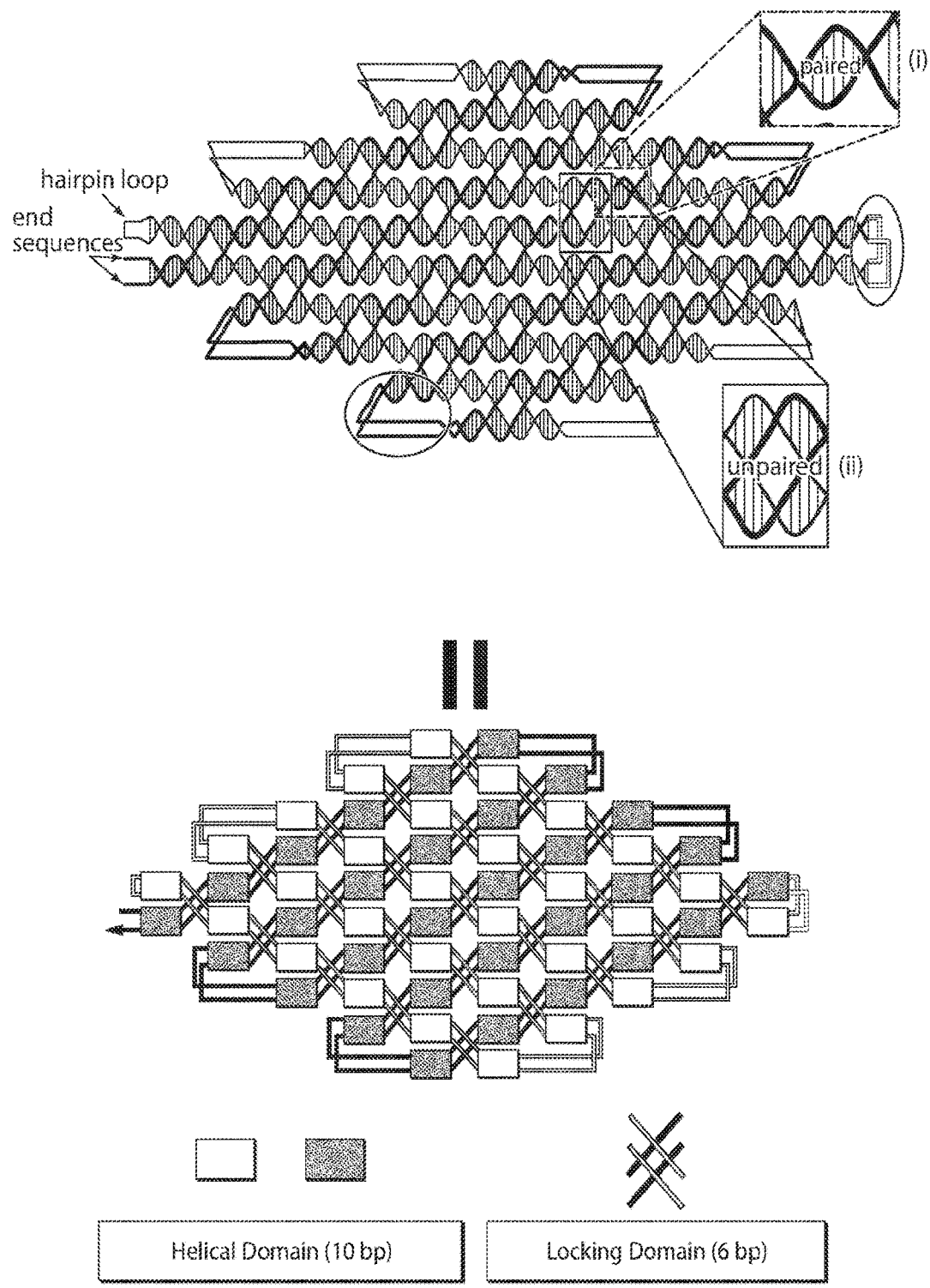
FIG. 2A, top panel, is a schematic of a double-helical model of an example of a ssDNA nanostructure of the present disclosure.

A single strand of DNA of the present disclosure is designed to assemble into a double-stranded chain, which resembles a large hairpin structure (see, e.g., FIG. 1, bottom schematics). That hairpin structure then assembles to form a two-layer structure containing paired helical domains and unpaired locking domains. A "layer" of a ssDNA nanostructure, as used herein, refers to a planar arrangement of a portion of the ssDNA or the DNA chain. FIG. 2A schematizes a ssDNA nanostructure having a first layer (light gray domains) positioned above a second layer (dark gray domains). It should be understood that while the nanostructures described herein contain two layers, more than two layers are contemplated. For example, a ssDNA nanostructure may contain 3, 4, 5, 6, 7, 8, 9, 10, or more layers, depending on the desired shape of the nanostructure.

An example of a nanostructure design of the present disclosure is shown in FIGS. 1 and 2A. In this example, a single strand of DNA is folded into a double-stranded DNA chain, which includes paired regions (referred to as "helical domains") (FIG. 2A(i)) and unpaired regions (referred to as "locking domains") (FIG. 2A(ii)). The locking domains direct the double-stranded DNA chain to further assemble into the final structure. To understand the topology design exemplified in FIG. 2A, the DNA strand is shaded dark gray for the bottom layer and light gray for the top layer. The two layers are connected by an unpaired region (outlined by the solid circle). Locking domains within the bottom layer are designed to base pair with their corresponding locking domains within the top layer, but without traversing through each other. In this example, helical domain contain 10 nucleotides base pairs (bp) and they are connected by 6 bp locking domains in the middle and single-stranded loops having a length of ~20 nucleotides on the periphery/edges of the shape. The 5' and 3' ends of this ssDNA are indicated on the left side of the schematic.

A "helical domain," as described above, refers to a paired region of a single strand of DNA, or more specifically, a paired region of a DNA chain that forms a helix. The single strand regions that contribute to a paired helical domain are typically located in the same layer. An example of a helical domain is illustrated in FIG. 2A(i). The length of a helical domain may vary. A helical domain will typically have a length that is h×k, where h represents the number of nucleotides required to make a full helical turn and k represents any integer of 1 or greater. As an example, for B form DNA there are typically 10.5 nucleotides per helical turn. Thus, for helical domains that contain B form DNA, the length can be represented as 10.5*k (rounding off to the nearest integer) where k represents an integer of 1 or greater (e.g., 2, 3, 4, 5, 6, 7, 8, 9 or 10), and where * denotes a multiplication sign.

In some embodiments, helical domains have a length of 10 to 100 nucleotides. For example, a helical domain may have a length of 10 to 90, 10 to 80, 10 to 70, 10 to 60, 10 to 50, 10 to 40, 10 to 30, 10 to 20, or 10 to 15. In some embodiments, helical domains may have a length of 10±2 nucleotides, 21±2 nucleotides, 31±2 nucleotides, 42±2 nucleotides, 52±2 nucleotides, 63±2 nucleotides, 73±2 nucleotides, 83±2 nucleotides, 94±2 nucleotides, or 104±2 nucleotides.

All of the helical domains in a nanostructure, or in a single layer of a nanostructure, need not be the same length relative to one another, although in some embodiments, they are. The number and relative lengths of the helical domains may depend on the desired shape (e.g., any arbitrary shape) of the nanostructure.

A "locking domain," as used herein refers to an unpaired region of a single strand of DNA, or more specifically, an unpaired region of the DNA chain. The single strand regions that contribute to an unpaired locking domain are typically located in the same layer. An example of a locking domain is illustrated in FIG. 2A(ii). The unpaired region refers to the relationship between regions of the single strand of DNA that lie in the same layer (e.g., FIG. 2A(ii), dark gray strands). It should be understood, however, that single-strand regions of locking domains of one layer pair with single strand regions of locking domains of another layer to "lock" the layers together, as illustrated in the example configuration shown in FIG. 2A(ii).

The length of a locking domain may vary. A locking domain will typically have a length of 4 to 10 nucleotides. In some embodiments, a locking domain has a length of 4, 5, 6, 7, 8, 9 or 10 nucleotides. In some embodiments, a locking domain has a length of 5 to 7 nucleotides. In some embodiments, a locking domain has a length of 6 nucleotides.

All of the locking domains in a nanostructure, or in a single layer of a nano structure, need not be the same length relative to one another, although in some embodiments, they are. The number and relative lengths of the locking domains may depend on the desired shape (e.g., any arbitrary shape) of the nanostructure.

Design of Single-Stranded DNA Nanostructures

To design an ssDNA structure, the first step is to create a continuous line of DNA that can fold into a designed shape by correct base-pairing. When a DNA nanostructure is designed, a target shape is usually created first and then DNA double helices are generated to fill the shape. Note that these DNA strands are not generated for single-stranded design purposes, so these strands need to be carefully broken and reconnected so that they can be merged into a single-stranded structure (see below: "One touch drawing of ssDNA").

However, simply breaking and reconnecting strands does not necessarily solve a key challenge in designing ssDNA, which is to create an ssDNA structure with minimal knotting complexity to avoid being kinetically trapped during the folding process. For example, if the process starts from a typical scaffolded DNA origami structure to create an ssDNA by connecting all strands into one piece, the knottedness of the resultant structure could prevent the single strand DNA from properly folding into the target shape (details are shown below: "Knot theory and crossing number of ssDNA structures" and "Dynamic relaxation model for knot simplification").

In order to precisely quantify the knotting complexity of different ssDNA models to facilitate the design process, an open-chain linear DNA strand is converted into a closed loop by connecting its 5' and 3' ends, and then characterize the topological complexity of this closed loop, which can be treated as mathematical knots. To avoid changing the knotting complexity of the ssDNA origami through the connection, attention is restricted to the following class of open chain structures: consider a certain 2D projection of the open chain diagram, if each of its two ends can be connected to a point at an infinite distance using a straight line segment that does not intersect the remaining part of the 2D projection, these two points will be further connected at infinite distance and thus the open chain will be converted into a closed loop without changing its knotting complexity (see FIG. 15A-15D for details). A "DNA knot" refers to the closed loop mathematical knot derived from an open-chain linear DNA in the above fashion. Note that all the ssDNA designs provided herein can be converted to such knots.

Figure 19:
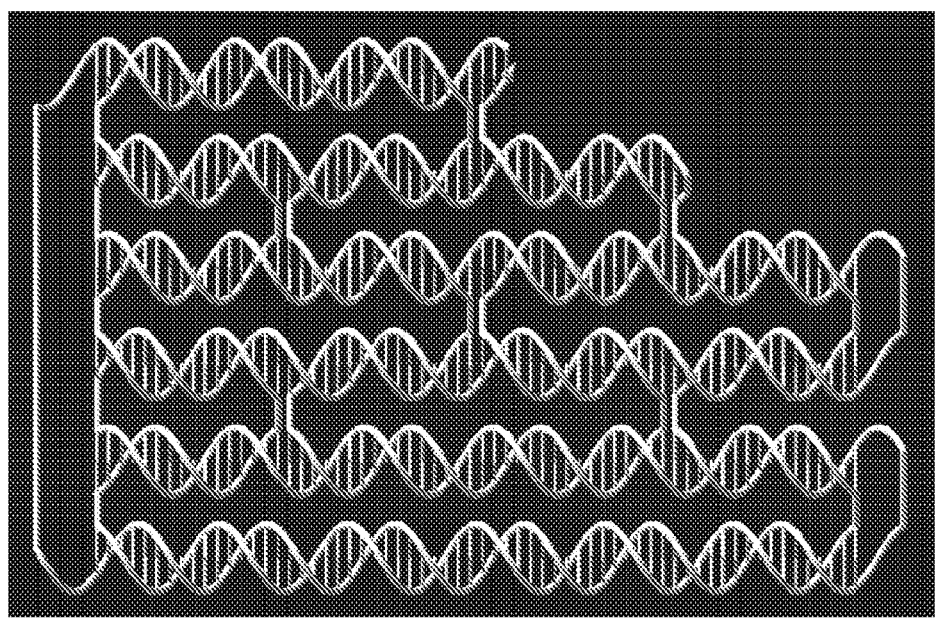
FIG. 19 is an example of a 2D projection of an antiparallel ssDNA nanostructure.

Two DNA knots are homotopic if they can be transformed into each other through a continuous deformation, which means strands cannot be cut during any operation (FIG. 18A-18D) (Alexander, J. W., & Briggs, G. B. On types of knotted curves. Annals of Mathematics, 562-586 (1926)). Such rules also apply to ssDNA since the DNA backbone cannot be cut or intersected during the folding process. The knotting complexity of ssDNA designs can be approximately described by the "crossing number," a knot invariant defined as the smallest number of crossings found in any diagram of the knot (Alexander, J. W. Topological invariants of knots and links. Transactions of the American Mathematical Society, 30(2), 275-306 (1928); and Murasugi, K. Knot theory and its applications. Springer Science & Business Media (2007)). A knot invariant is a "quantity" that is mathematically the same for equivalent knots. In other words, if the invariant is computed from a knot diagram, it should give the same value for two knot diagrams representing equivalent knots. If a knot has a crossing number of zero, then it is topologically equivalent to an unknotted circle (also referred as an unknot). In nature, most of the RNA and protein structures have crossing number of 0 and only in rare cases some proteins may have very small crossing number. On the contrary, as shown in FIG. 19, ssDNA designs derived from traditional DNA origami structures tend to result in complex knots with high crossing numbers, which will likely hinder proper folding.

To address this challenge, several different design strategies were explored (see below: "Design of DNA with crossing number of zero"), and one having a crossing number of zero and being structurally stable was identified.

In conventional scaffolded DNA origami structures, adjacent double helices are connected by crossover linkages. One of the first considerations in ssDNA design is the choice between antiparallel and parallel crossovers for inter-helical cohesion.

Figure 20A:
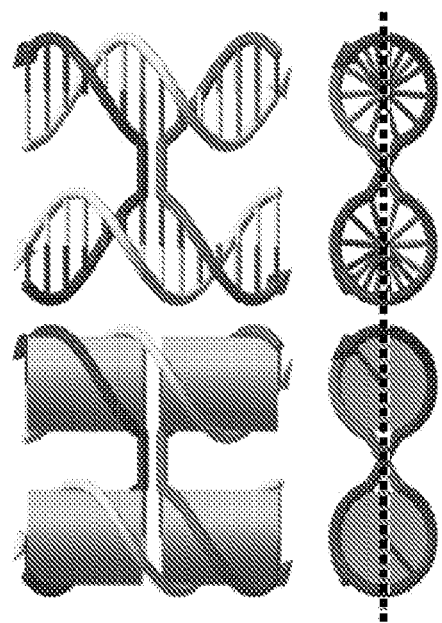
FIGS. 20A-20B show an anti-parallel crossover model (FIG. 20A) and an anti-parallel ssDNA nanostructure having an inserted gray semitransparent central plane (FIG. 20B), which contains all DNA helical axes. The DNA strand travels through this plane 126 times in this design pattern, which makes the folding of such a structure difficult.
Figure 20B:
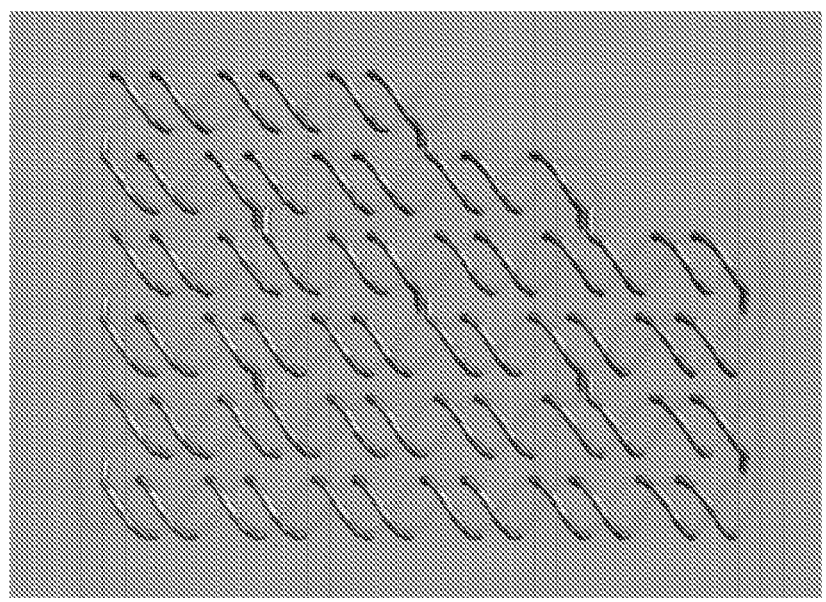

As shown in FIG. 8A, at every anti-parallel crossover position, DNA strands run through the central plane that contains all the parallel DNA helical axes (dashed lines in the model), like threading a needle through a piece of fabric (see also FIGS. 20A-20B). On the contrary, as shown in FIG. 8B, at parallel crossover positions, DNA strands do not go through this plane, which could reduce the knotting complexity of the structure. For this reason, parallel crossovers are used for inter-helical cohesion in ssDNA nanostructures as provided herein.

Figure 29A:
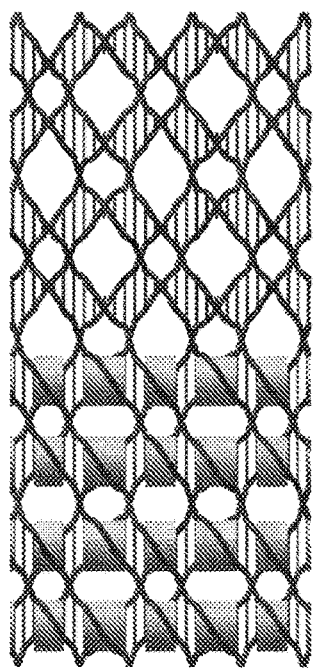
FIGS. 29A-29C show examples of design principles for parallel helices in ssDNA nanostructures of the present disclosure.

Nonetheless, adopting parallel crossovers does not solve all the knotting problems of ssDNA because the nature of B-type DNA requires helical geometry throughout the whole structure. In other words, even if the DNA strands do not go through the central plane at the crossover positions, they still need to go through this plane somewhere in order to form the continuous pi-pi stacking inherent in a rigid DNA nanostructure, which will usually make the design knotted (e.g., as in FIG. 21B and FIG. 30). One exception is shown in FIG. 29A, where crossovers are created at all possible positions and thus the ssDNA does not go through the central plane at all. However, this design appears to be structurally unstable as many of its unperturbed base pairing sections are very short (1 base pair), and failed to produce the folded target shape in preliminary experiments (data not shown).

Figure 8C:
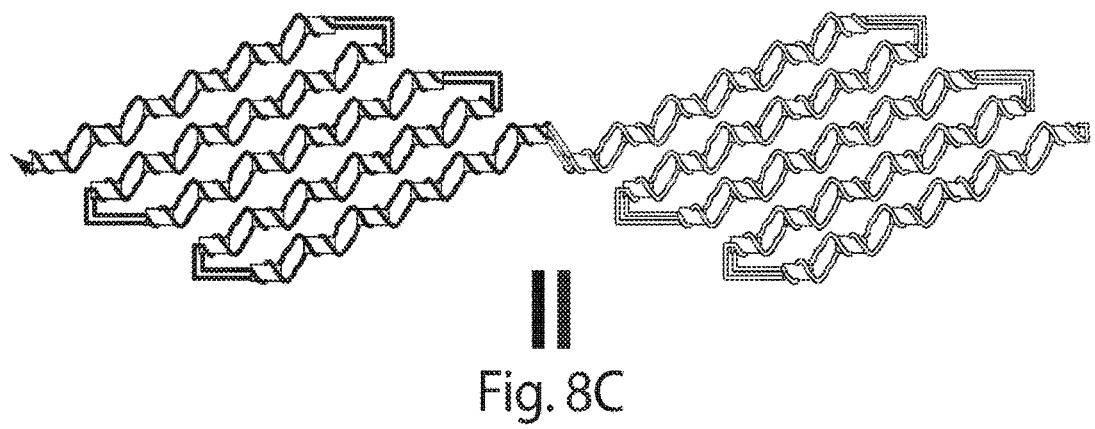
Figure 8D:
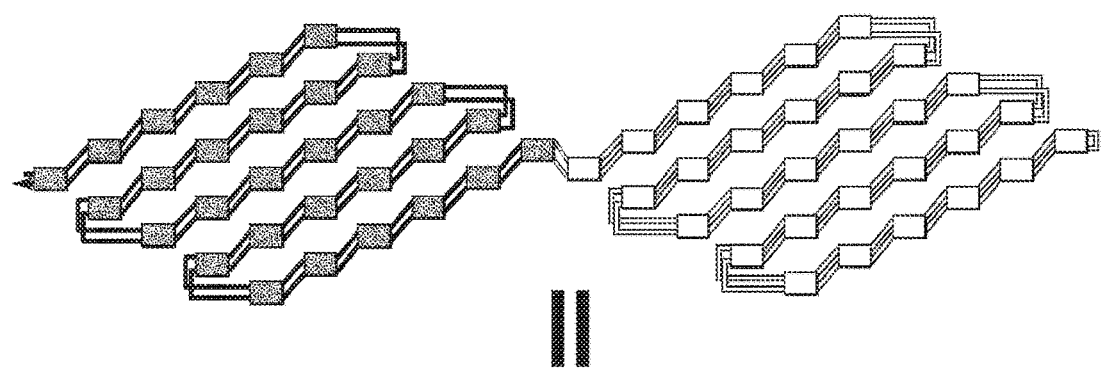
Figure 8E:
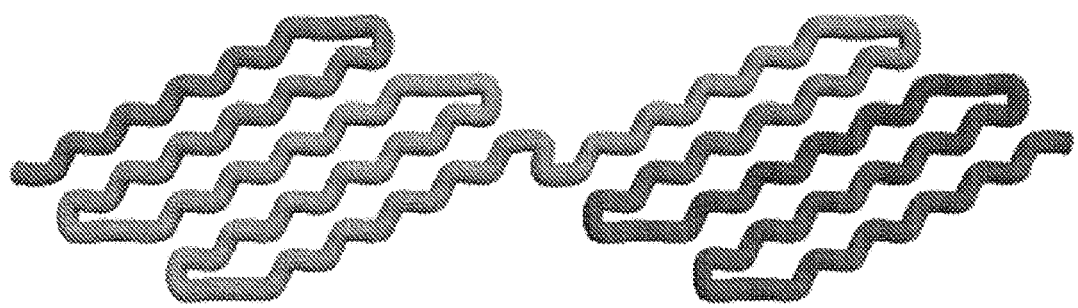
Figure 8F:
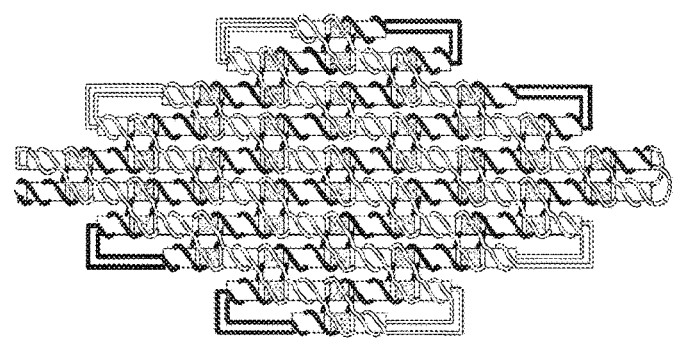
Figure 8G:
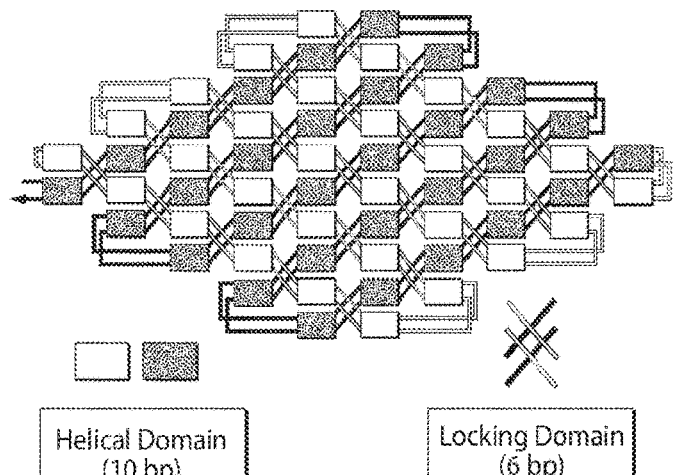
Figure 8H:
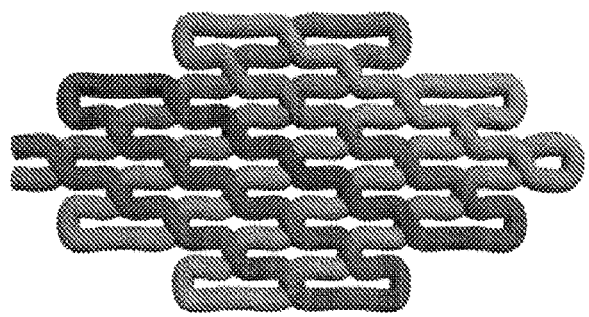
Figure 8I:
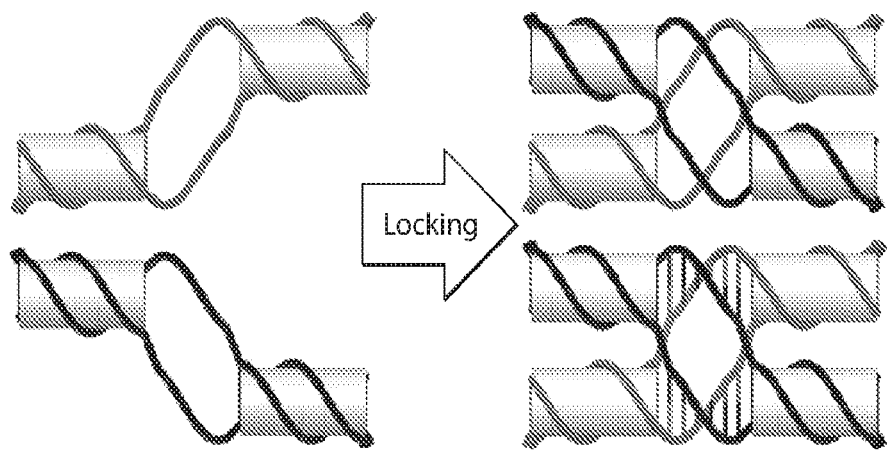
Figure 21A:
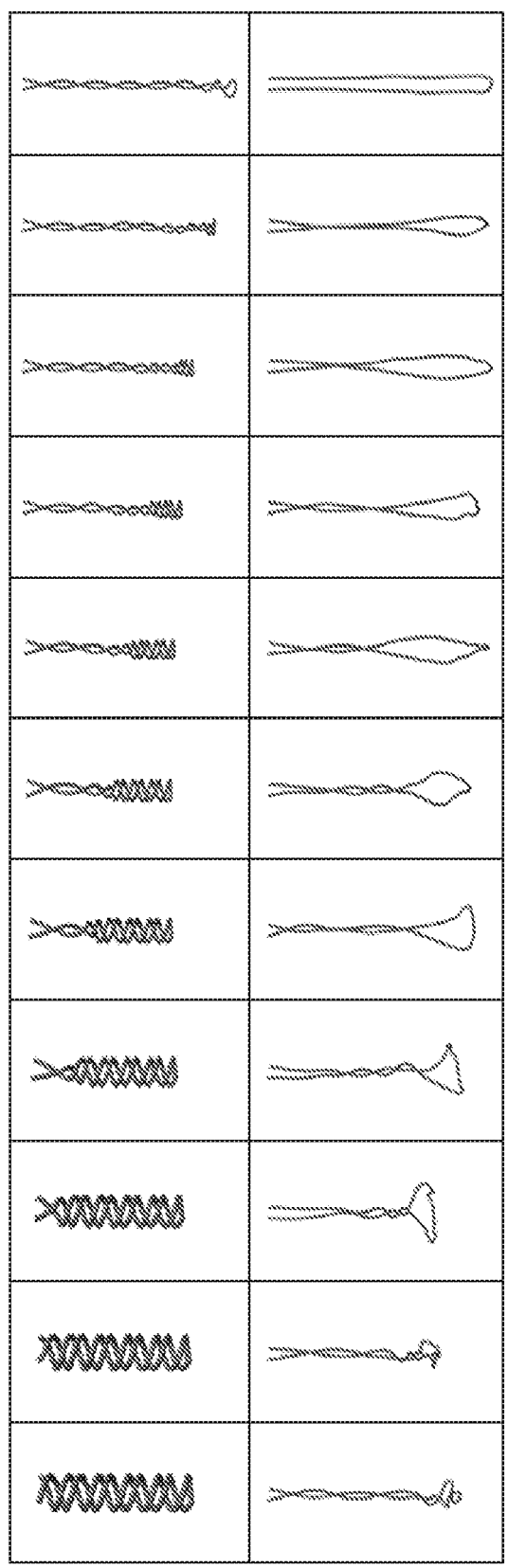
FIGS. 21A-21B show dynamic animation to demonstrate the knot relaxation process of a simple DNA hairpin (FIG. 21A) and a double helical DNA with antiparallel crossovers analogue (FIG. 21B).
Figure 21B:
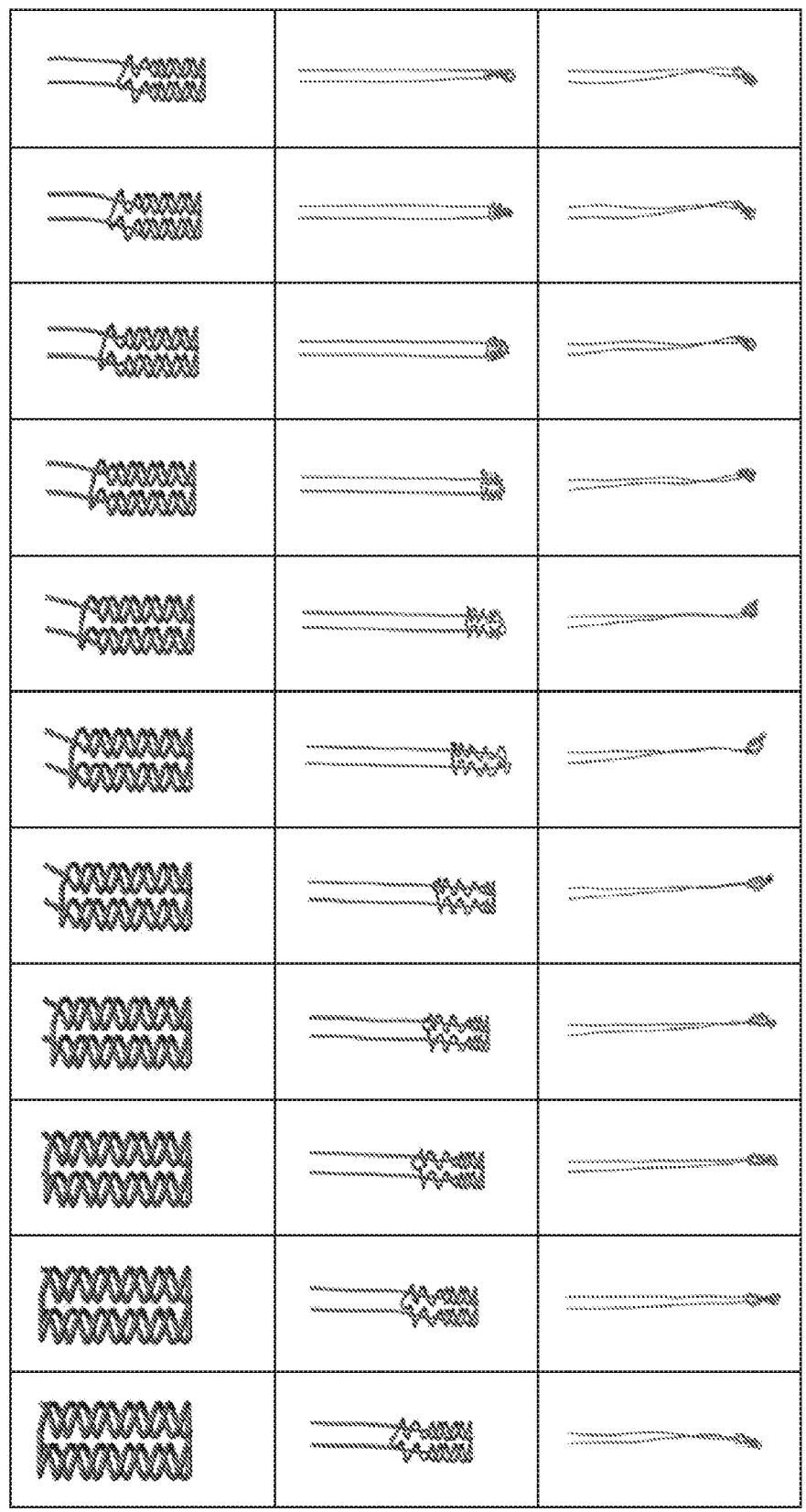
Figure 22:
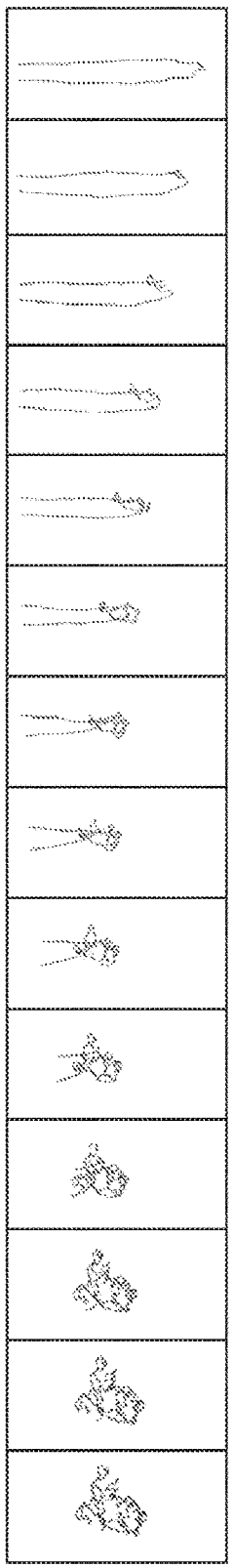
FIG. 22 provides selected screenshots of a dynamic knot relaxation process of RNAse (PDB: 1GQV).
Figure 23:
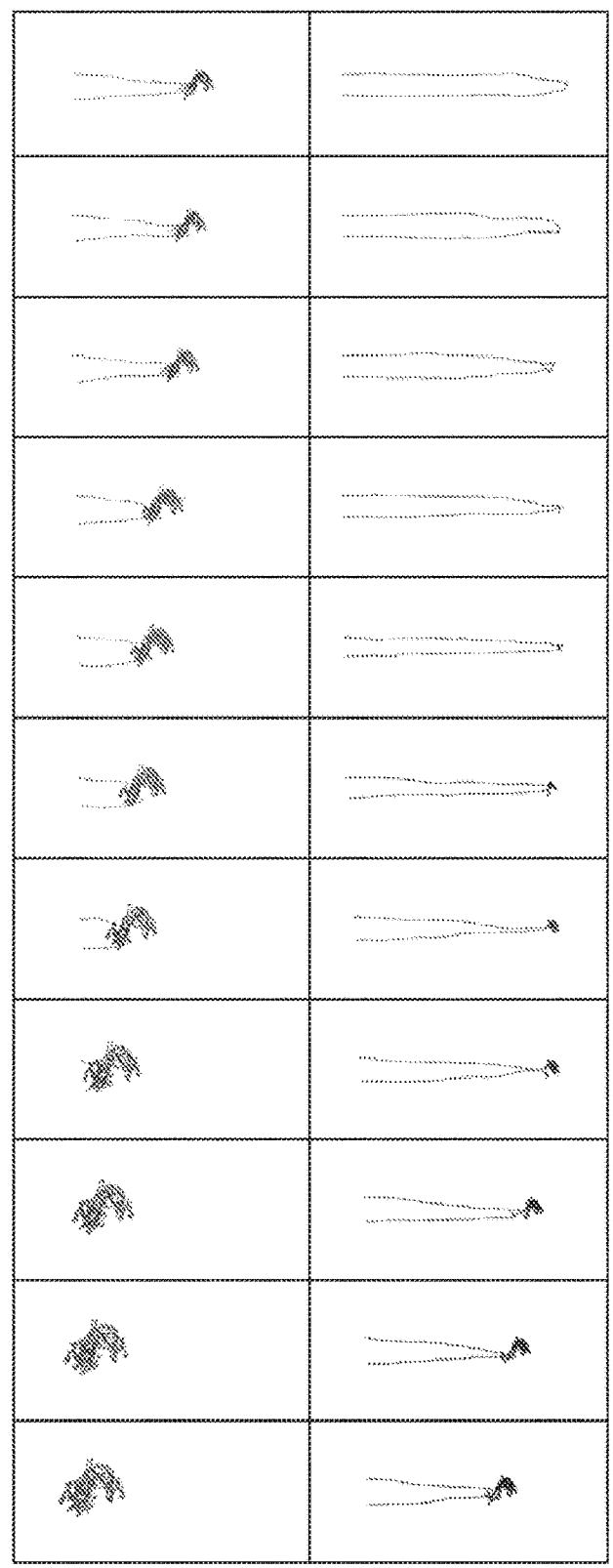
FIG. 23 provides selected screenshots of a dynamic knot relaxation process of telomerase (PDB: 3KYL).
Figure 24:
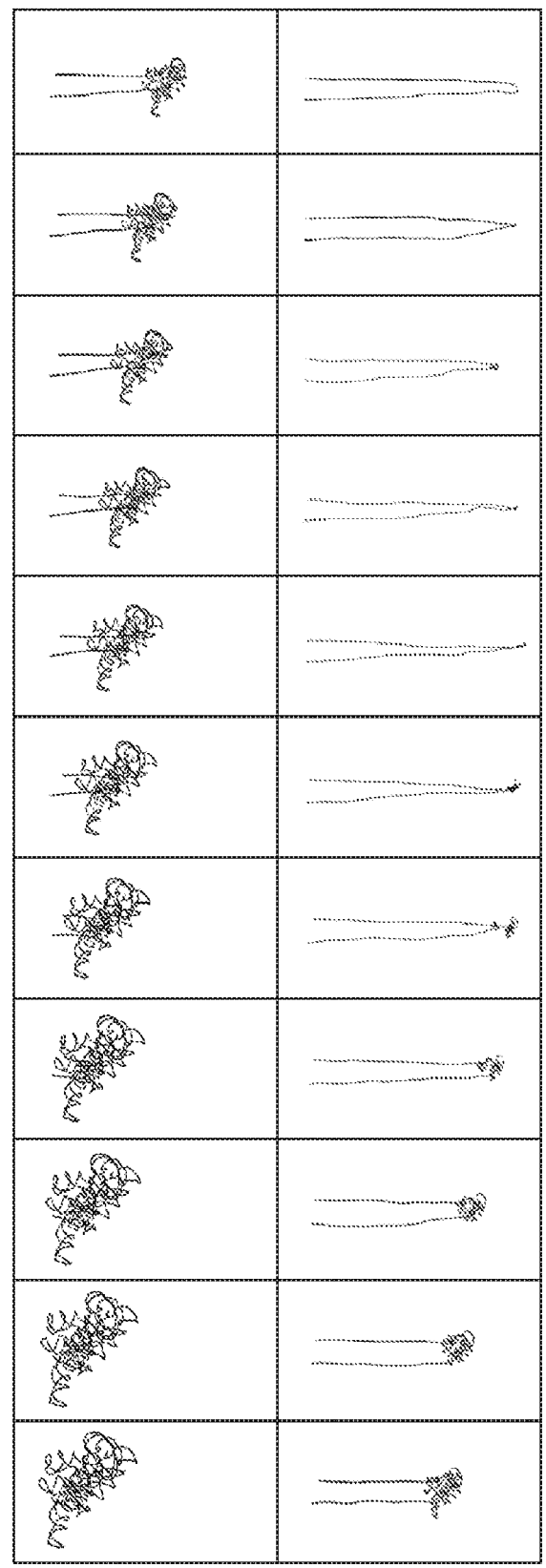
FIG. 24 provides selected screenshots of a dynamic knot relaxation process of Group II Intron (PDB: 3EOH).
Figure 25:
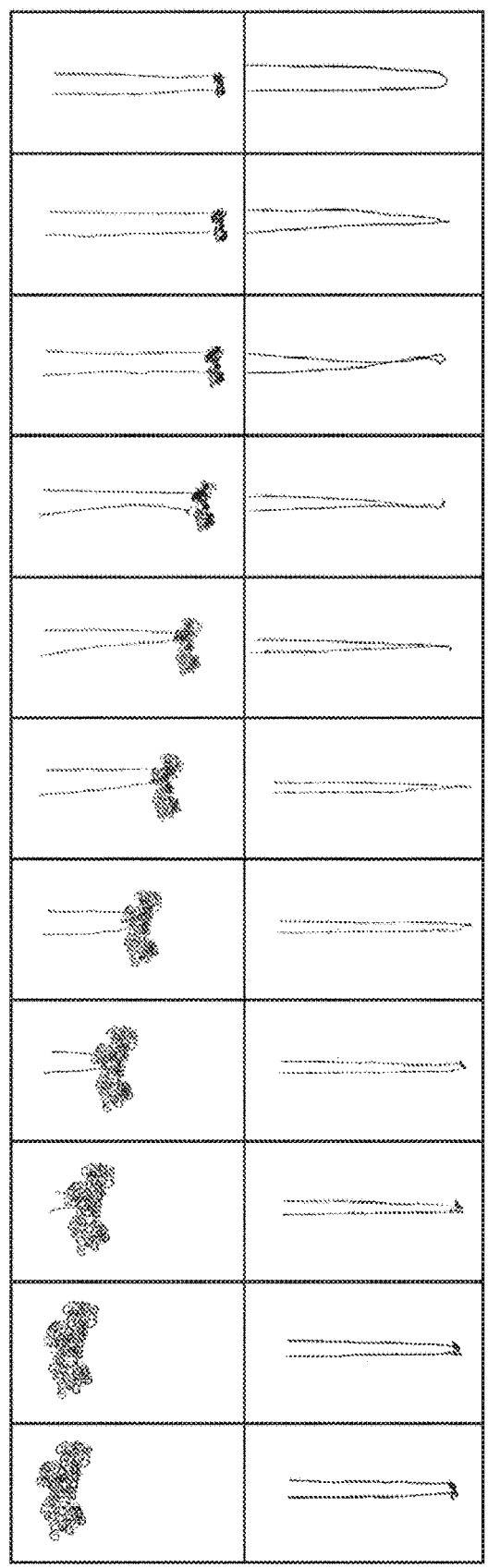
FIG. 25 provides selected screenshots of a dynamic knot relaxation process of 16S rRNA (PDB: 1L94).

A solution for this dilemma is shown in FIG. 8C-8H, where a putative partially paired double strand intermediate was created (FIG. 8C-8E) and this double strand was further folded into designed shapes (FIG. 8F-8H). This design has longer unperturbed base pairing sections and is thus expected to be structurally stable. Also, this design has a crossing number of 0 (see below: "Design of ssDNA with crossing number of zero"). In this ssDNA model, only parallel crossovers are present. This design has continuous $\pi$-$\pi$ stacking along all the helices to maintain the rigidity of the structure. The white and gray cylinders in the models (FIGS. 8C and 8F) are used to denote unperturbed base pairs and different domains; whenever there is a nick point in the helices, the cylinder breaks. By separating these cylinders into two groups, it can be seen that the majority of the ssDNA (FIGS. 8C and 8F) contains two distinct domains: the 10 bp helical domains (white cylinders) and the 6 bp locking domains (gray cylinders), which are also depicted as rectangles and crosses in FIGS. 8D and 8G. Each locking domain is between two adjacent parallel crossovers and all blue strands are on top of red strands at crossover points in this design. One of the key features in this design is that that all the domains in the top-layer are covalently linked in a raster-filling pattern and then connected to the domains in the bottom layer which have symmetrical geometry. In FIGS. 8E and 8H, to help visualize the folding track of the covalently linked putative intermediate structure, a pipeline style model was created. When all the locking domains are further formed through base pair recognition (FIG. 8I), the putative intermediate becomes a fully folded ssDNA structure. Although the DNA strand needs to go through the central plane many times in the design, such plane-crossings all happen on the helical domains but not locking domains. To illustrate that this ssDNA design is not knotted, a dynamic relaxation system was created in which the ssDNA pipeline model is relaxed under simulated gravity while fixing both of its ends (see below: "Dynamic relaxation model for knot simplification"). Under this relaxation, the ssDNA becomes an unknotted rope (double-stranded), revealing that it has a crossing number of 0 (shown in FIG. 8J). Such a double-stranded pipeline can be further relaxed under simulated gravity into a single-stranded open loop with its 3' and 5' ends fixed, which also has a crossing number of 0 (FIGS. 18D and 21A).

Figure 4C:
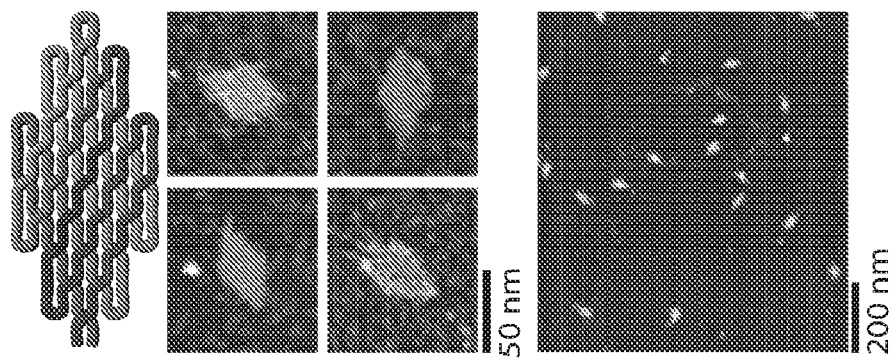
FIGS. 4A-4C are images of examples of ssDNA diamond-shape nanostructures, each having a different size.
Figure 4B:
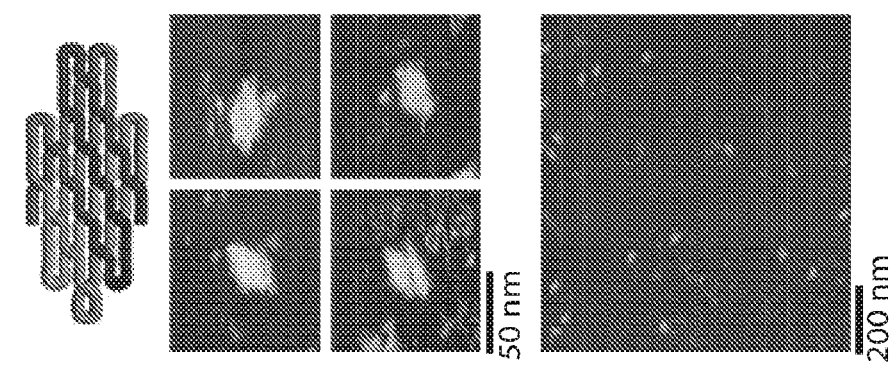
Figure 4A:
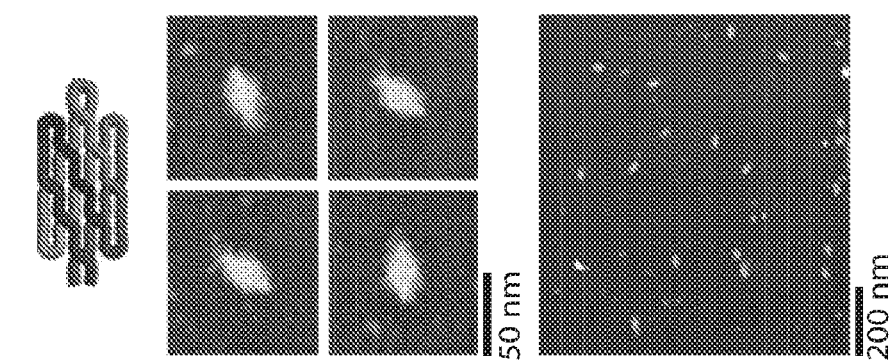

This two-layer design strategy can be applied to diamond-shaped ssDNA structures with variable sizes. Based on the number of pipeline sections in the two layers, m×n ssDNA structures (m denotes the number of diagonally oriented, partially-paired helices in the top layer and n denotes number of partially-paired helices in the bottom layer) were successfully created, such as the 3×3, 4×4 and 5×5 ssDNA structures which are shown in FIGS. 4A-4C. For example, the 3×3 ssDNA (FIG. 4A) contains 9 locking domains in the design and the 5×5 ssDNA (FIG. 4C) contains 25 locking domains. When all the locking domains are correctly paired in the folding process, a well-folded ssDNA structure will be produced. FIGS. 4A-4C (top panels) shows the pipeline-style models of these structures and the corresponding AFM images. These ssDNA structures were folded in 12.5 mM Mg2+ buffer (see Materials and methods section) using a 2 hour annealing ramp from 85° C. to 25° C.

One Touch Drawing of ssDNA

Figure 14A:
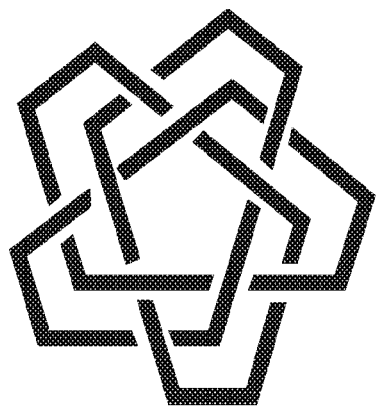
FIGS. 14A-14D demonstrate the concept of one touch drawing.
Figure 14B:
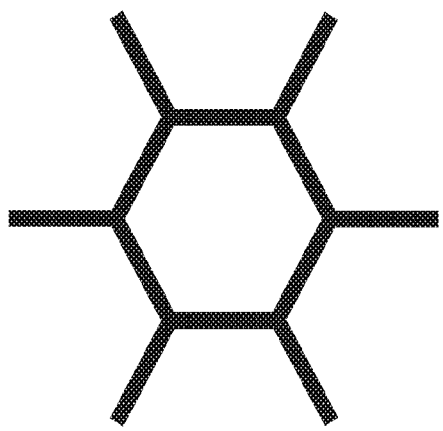
Figure 14C:
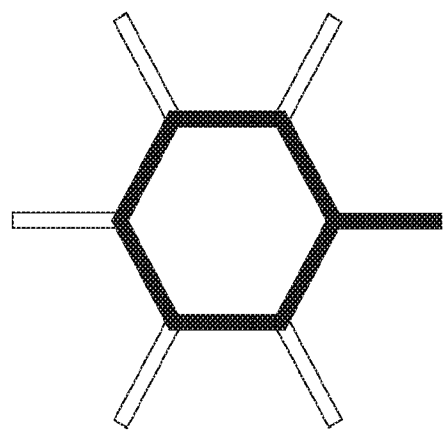
Figure 14D:
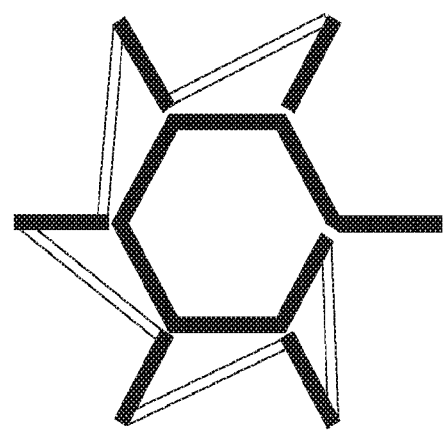

The methods of the present disclosure are designed to result in the folding of ssDNA into complex shapes similarly to those produced in one touch drawing artwork (FIG. 14A). For some patterns, such as the one shown in FIG. 14B, one touch drawing cannot be achieved directly. FIG. 14C shows an attempt to draw the shape with one continuous line (the dark gray segments) with several light gray sections left undrawn. If additional "bridging" segments are added, such as the light gray sections in FIG. 14D, the pattern can be achieved using one touch drawing. In a ssDNA nanostructure design of the present disclosure, these extra bridging segments are replaced with ssDNA loops connecting distant 5' and 3' ends.

Figure 15A:
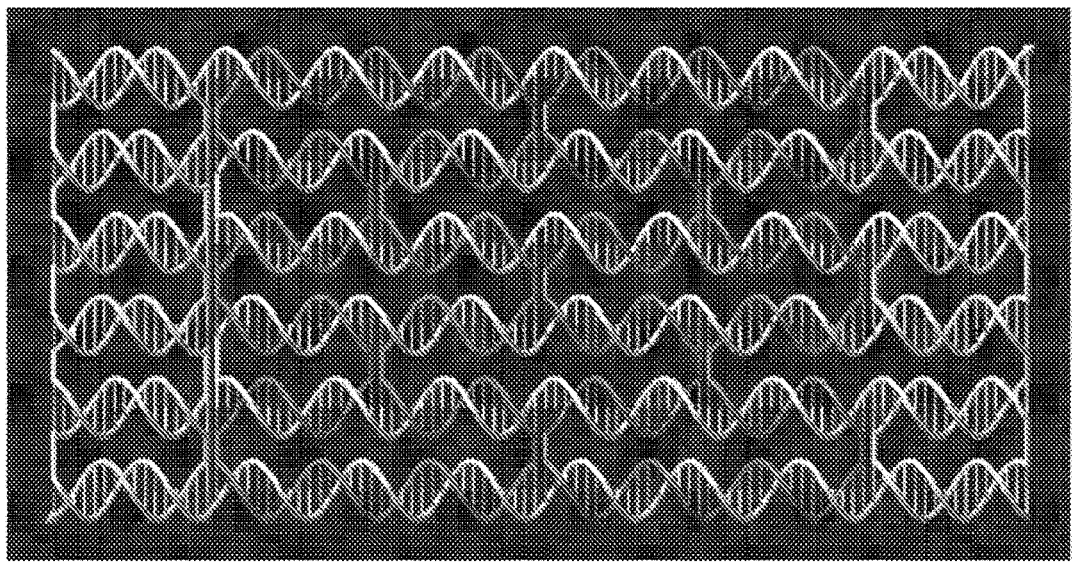
FIGS. 15A-15D show an example of how to disconnect strands of a conventional multi-strand scaffold DNA nanostructure and reconnect the strands in a way that forms a single-stranded DNA nanostructure of the present disclosure.
Figure 15B:
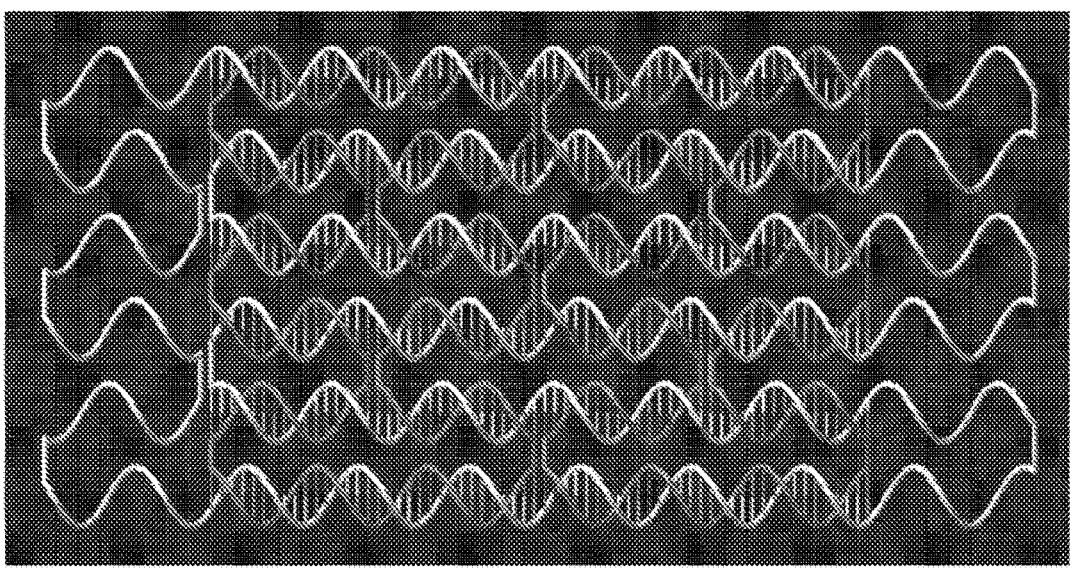
Figure 15C:
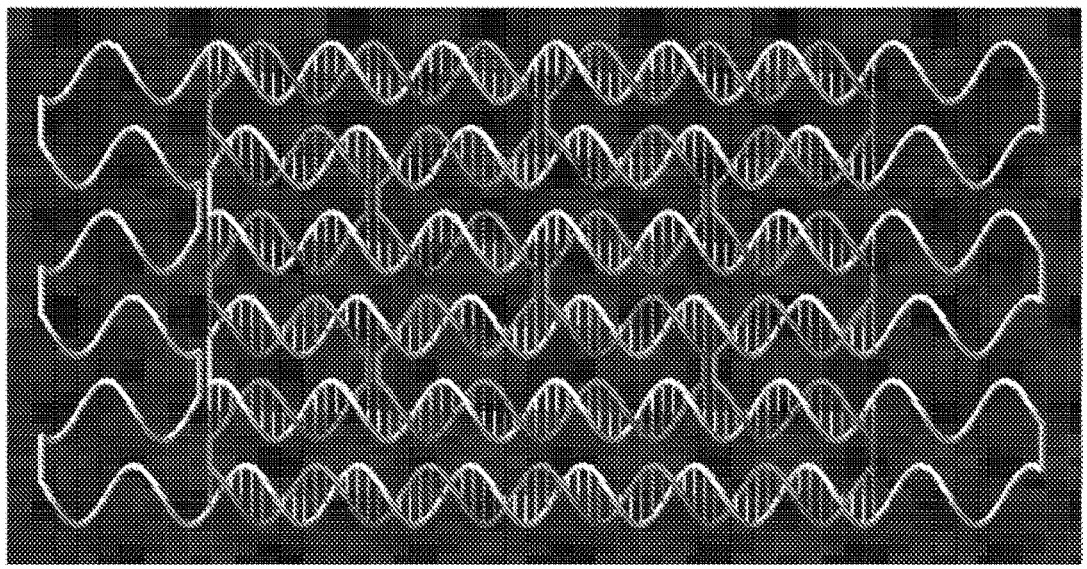
Figure 15D:
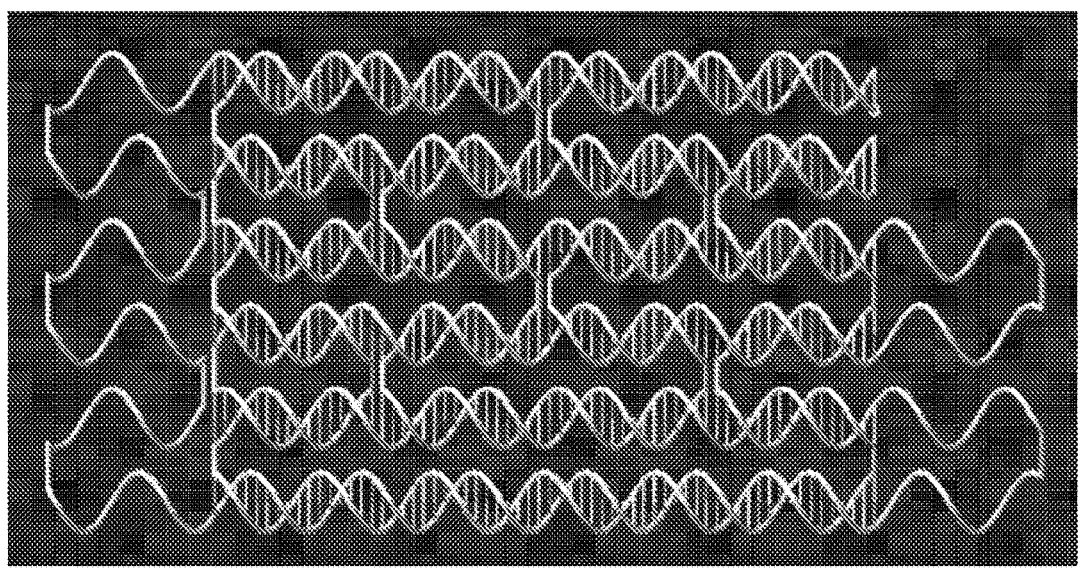

One non-limiting method of creating a ssDNA nanostructure of the present disclosure is to break and reconnect strands in a conventional multi-strand scaffold DNA nanostructure so that all the staple and scaffold strands are merged into a single contiguous DNA strand. A "conventional multi-strand scaffold DNA nanostructure" refers to a DNA nanostructure assembled from a long single-stranded DNA (scaffold) and multiple, shorter DNA strands (staples). As shown in FIGS. 15A-15D, in a first step, an antiparallel multi-strand scaffold DNA nanostructure in which staple strands are not cut into short pieces is used as a starting template (FIG. 15A). This design template in FIG. 15A contains one long scaffold strand (white) and four staple strands (from left to right: white, dark grey, light grey and white). Because the two white staple strands are not cyclized, and their 5' and 3' ends cannot be easily connected with the remaining part of the design, they can be deleted to simplify the design into the structure shown in FIG. 15B. Here, there are three strands remaining. By breaking and reconnecting the crossover in the mid-bottom of the design, two staple strands (dark grey and light gray) can be merged into one longer strand (FIG. 15C). This longer staple can be further merged with the scaffold strand at the top-right corner of the structure to become one continuous strand (FIG. 15D). Based on the principles shown in the above example process, in some embodiments, a conventional multi-strand scaffold DNA nanostructure can be converted into a ssDNA nanostructure of the present disclosure without creating long unpaired loop regions.

Knot Theory and Crossing Number of ssDNA Structures

As indicated above, the methods provided herein result in the production of nucleic acid nanostructures having high structural complexity while maintaining knotting simplicity (unknotted), component simplicity and homogeneity (one single strand of DNA). In the field of DNA topology, DNA "knotting" refers to DNA that is intertwined many times and tied into knots (see, e.g., Buck D, *Proceedings of Symposia in Applied Mathematics* 2009; 66: 1-33; Rybenkov V V et al. *Proc Natl Acad Sci USA*. 1993; 90(11): 5307-5311, each of which is incorporated herein by reference). Provided herein, in some embodiments, is a method of producing a ssDNA nano structure with minimal knotting complexity to avoid the nucleic acid from being kinetically trapped during the folding process, which can prevent proper folding of the nucleic acid into a user-defined target shape.

While unimolecular folding is commonly observed in proteins, it is not straightforward to achieve similar bottom-up folding complexity using synthetic DNA. Although complex 2D and 3D shapes can be constructed with scaffolded DNA origami or DNA tile/brick strategies, converting them into single-stranded DNA nanostructures can be difficult due to potential knotting problems, which is discussed below.

Figure 16:
FIG. 16 is a 2D projection of an example of an anti-parallel ssDNA nanostructure that exhibits improper folding, having ~800 nucleotides (nt) and a crossing number greater than zero.

Knot theory in topology can be used to distinguish different DNA knots to help guide the design process of a ssDNA as provided herein. As a first step, a 2D projection of a 3D ssDNA model can be treated as a knot diagram, which also contains information about over-strand and under-strand at all intersection points. FIG. 16 shows a 2D projection of an example of ssDNA model, a simplified version of FIG. 15D. The 5' and 3' ends of this ssDNA are shown on the upright corner of the design. The sticks illustrating the base pairing are not treated as part of the knot diagram. A "knot," as used herein, is mathematical term referring to a simple closed curve in three-dimensional space. An "unknot" is a type of mathematical knot: a simple open loop, drawn with no crossings. A ssDNA nanostructure herein is considered "unknotted" if the structure is topologically equal to an open loop when its two ends are connected to each other according to the following rules. When a 2D projection of an ssDNA model, for example, is treated as a knot diagram, it is assumed the two ends of this ssDNA model are connected in a way that retains its knotting properties. For ssDNA designs provided here, as their 5' and 3' ends are usually close to each other (see, e.g., the ssDNA of in FIG. 16, with its ends at the upright corner), direct connection of both ends will result in a closed loop (FIG. 17A-17B). In general, for any 2D projection of a biological macromolecule with exposed ends, if there is a way to connect each of its two ends to a point at infinite distance using a straight line segment that does not intersect the remaining part of the projection, these two points can be further connected at infinite distance to convert the projection into a closed loop (FIG. 17C-17D). In this way, a ssDNA be converted into a closed loop while preserving its knotting complexity.

According to knot theory, two knots are topologically equivalent if they can be related by a sequence of three kinds of moves on their diagrams. These operations, called the Reidemeister moves, are shown in FIGS. 17A-17C. The Reidemeister moves ensure that no intersections are allowed in the operation of a mathematical knot. This restriction also applies to the operation of ssDNA models. For example, by applying Type I Reidemeister moves (or by twisting), DNA hairpin structures can be converted into an unknotted open loop (FIG. 17D). If all Type I Reidemeister moves are applied to the diagram shown in FIG. 15, the ssDNA model can be further simplified into a reduced diagram (containing no reducible crossings) shown in FIG. 19.

The next step for designing a ssDNA is to determine the knotting complexity of a DNA knot diagram so that the likelihood of it folding correctly can be estimated. One factor used to approximate the knotting complexity of ssDNA is the crossing number. Note that the reduced diagram shown in FIG. 19 is also an alternating diagram (Lickorish, W. R. (2012). An introduction to knot theory (Vol. 175). Springer Science & Business Media), in which the crossings alternate under and over each time the strand intersects itself. If the track of the ssDNA is followed from the 5' end to the 3' end, it passes alternately over and under crossings. According to Tait conjectures, any reduced diagram of an alternating knot has the fewest possible crossings. Here, the crossing number of the design of FIG. 19 is 63.

For anti-parallel crossovers, as shown in FIG. 20A-20B, the local strand arrangement is alternating. At the same time, double helical DNA is alternating because its two strands are always intertwined along its helices. As a result, if a ssDNA is designed from anti-parallel crossovers and double helices, such a design will be an alternating diagram because all its components are alternating after simplification on the edges (similar to FIG. 19). If a central plane containing all DNA helical axes is placed (dashed lines in FIG. 20A and gray semitransparent central plane in FIG. 20B), it can be sees that there is a need to thread a needle through that central plane 126 times to weave the shape for the design with a crossing number of 63.

Dynamic Relaxation Model for Knot Simplification

To study the knotting complexity of a structure, a novel dynamic relaxation model to simplify the knot structure without changing its knotting complexity is presented. In this model, both the 3' and 5' ends of a 3D ssDNA model of the present disclosure are fixed while the remaining part of the strand falls under simulated gravity. The falling process will relax the unknotted crossings, and thus simplify the diagram. For example, if a structurally "complex" 3D knot model is actually an unknot (crossing number 0), the relaxation will simplify the model into an untied loop (unfolding), e.g., as in the DNA hairpin shown in FIG. 21A. On the other hand, if a 3D knot model is knotted, the crossings will be kept during the falling process, e.g., as in the double helical DNA structure shown in FIG. 21B.

The dynamic relaxation model is implemented using Autodesk 3ds Max software. Linear models of target shapes are first created according to the target shape such as the first snapshot in FIGS. 21A-21B. Such a line/spline object is then treated as a reactor rope and added to a rope collection. The relaxation is performed with 0.5 Friction and 0.5 Air Resistance with both ends of the rope fixed. The Rope Type of the object is set to be Constraint and Avoid Self-Intersections. This dynamic relaxation model can also be applied to RNA or protein structures, such as those shown in FIGS. 22-25. In these cases, the Protein Data Bank (PDB) data of an RNA or protein structure is first converted to a line/spline object in the software, and then treated as a rope for relaxation.

Figure 26A:
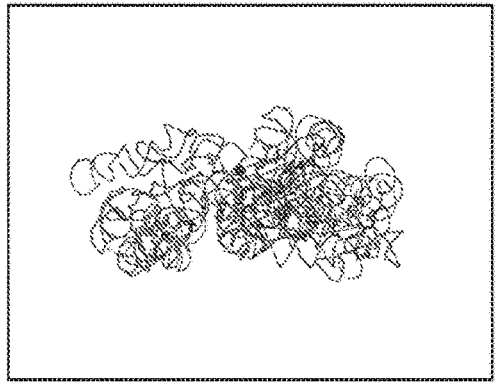
FIGS. 26A-26F show a selection of the falling direction of a molecule during the relaxation. Side view (FIG. 26A) and top view (FIG. 26B) of 16S rRNA (PDB: 1L94). Both ends of the molecule are highlighted with spheres. Side view (FIG. 26C) and top view (FIG. 26D) of 16S rRNA with a horizontal plane placed at the height of the two spheres.
Figure 26B:
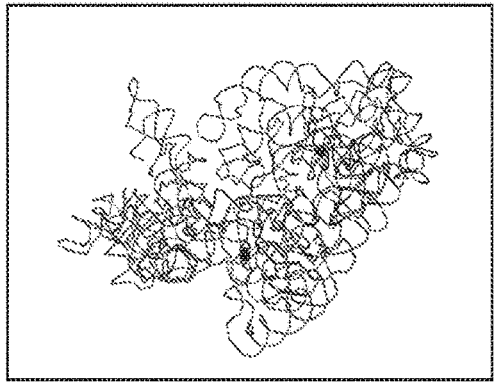
Figure 26C:
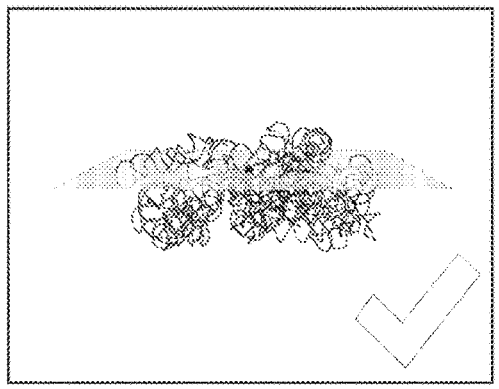
Figure 26D:
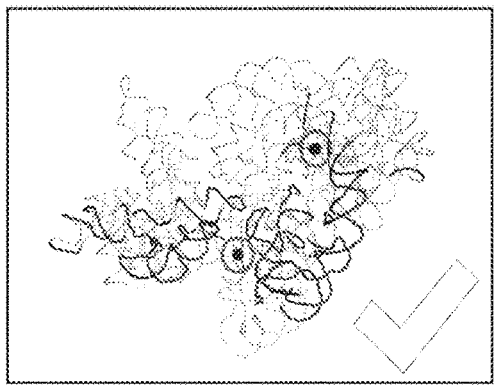
Figure 26E:
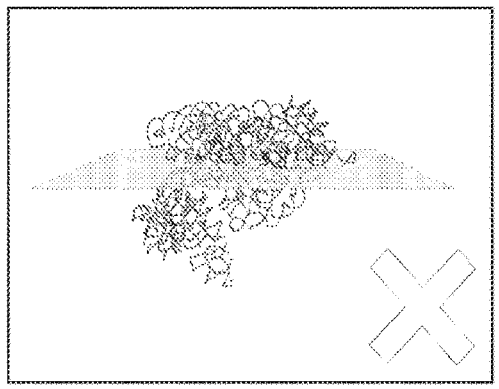
Figure 26F:
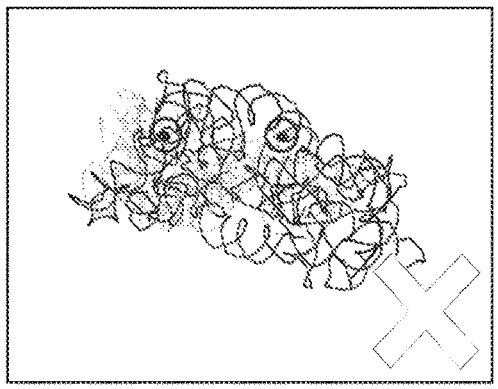

In the dynamic relaxation, the falling direction is chosen in a way that the falling process does not change the knotting complexity of the model. For simple examples, such as those shown in FIGS. 21A-21B, both ends of the structure can be easily fixed at the top, and falling of the rest of the structure will not change the knotting complexity. More generally, for complex natural biomolecules such as the 16S rRNA shown in FIGS. 26A-26F where its two end points (highlighted with spheres) are not exposed, the falling direction is chosen according to the following procedure: 1, the molecule is positioned properly so that both of its ends (spheres) are at the same height; 2, a horizontal plane is arranged at the height of the spheres (FIGS. 26C, 26E); 3, the portion of the molecule above the horizontal plane is projected onto this plane (FIGS. 26D, 26F); 4, if neither sphere is surrounded by a closed loop (FIG. 26D), the falling direction is legitimate; 5, if either one of the spheres is surrounded by a closed loop (FIG. 26F), the falling direction needs to be changed because the end point may go through that closed loop during falling process, potentially changing the knotting complexity of the structure. The above procedure ensures that the knotting complexity will not be artificially changed during the relaxation process.

As demonstrated in FIGS. 22-25, RNAse (PDB: 1GQV, length: 135 amino acids), Telomerase (PDB: 3KYL, length: 596 amino acids), Group II Intron (PDB: 3EOH, length: 412 nucleotides) and 16S rRNA (PDB: 1L94, length: 1514 nucleotides) can all be relaxed into unknotted open loops via the dynamic relaxation system, which reveals that they all have a crossing number of 0.

Figure 27:
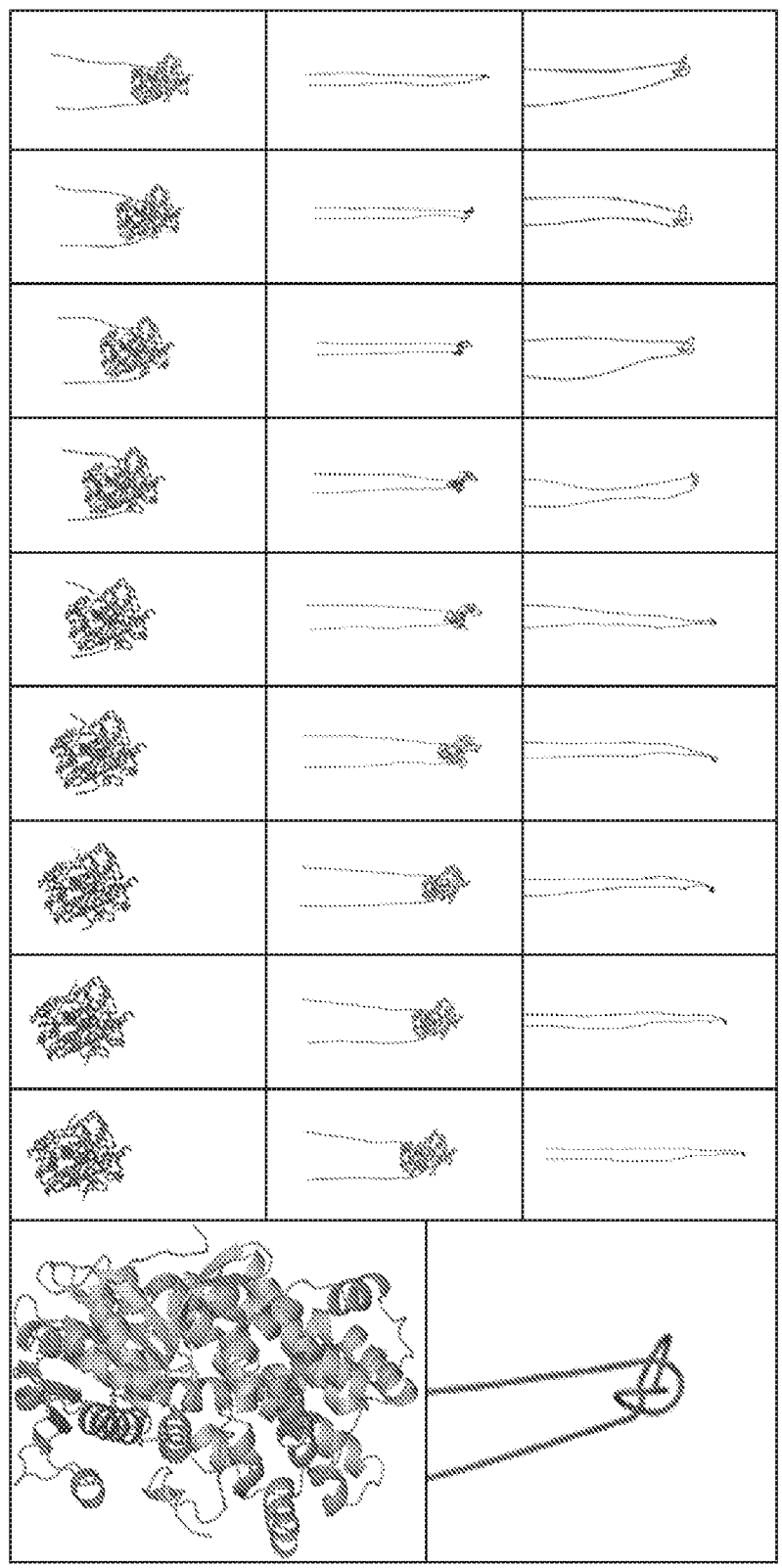
FIG. 27 provides selected screenshots of a dynamic knot relaxation process of acetohydroxy acid isomeroreductase (PDB: 1YVE-L). Top left: cartoon model of acetohydroxy acid isomeroreductase (1YVE-L). Bottom left: final state of dynamic relaxation.

If this dynamic relaxation is applied to a knotted protein (which is rarely observed) such as the carboxy-terminal domain of acetohydroxy acid isomeroreductase (PDB: 1YVE-L)[42] shown in FIG. 27, the rope will become a simple knot. The crossing number of this knot is 3, which is the simplest knot[41].

Figure 28:
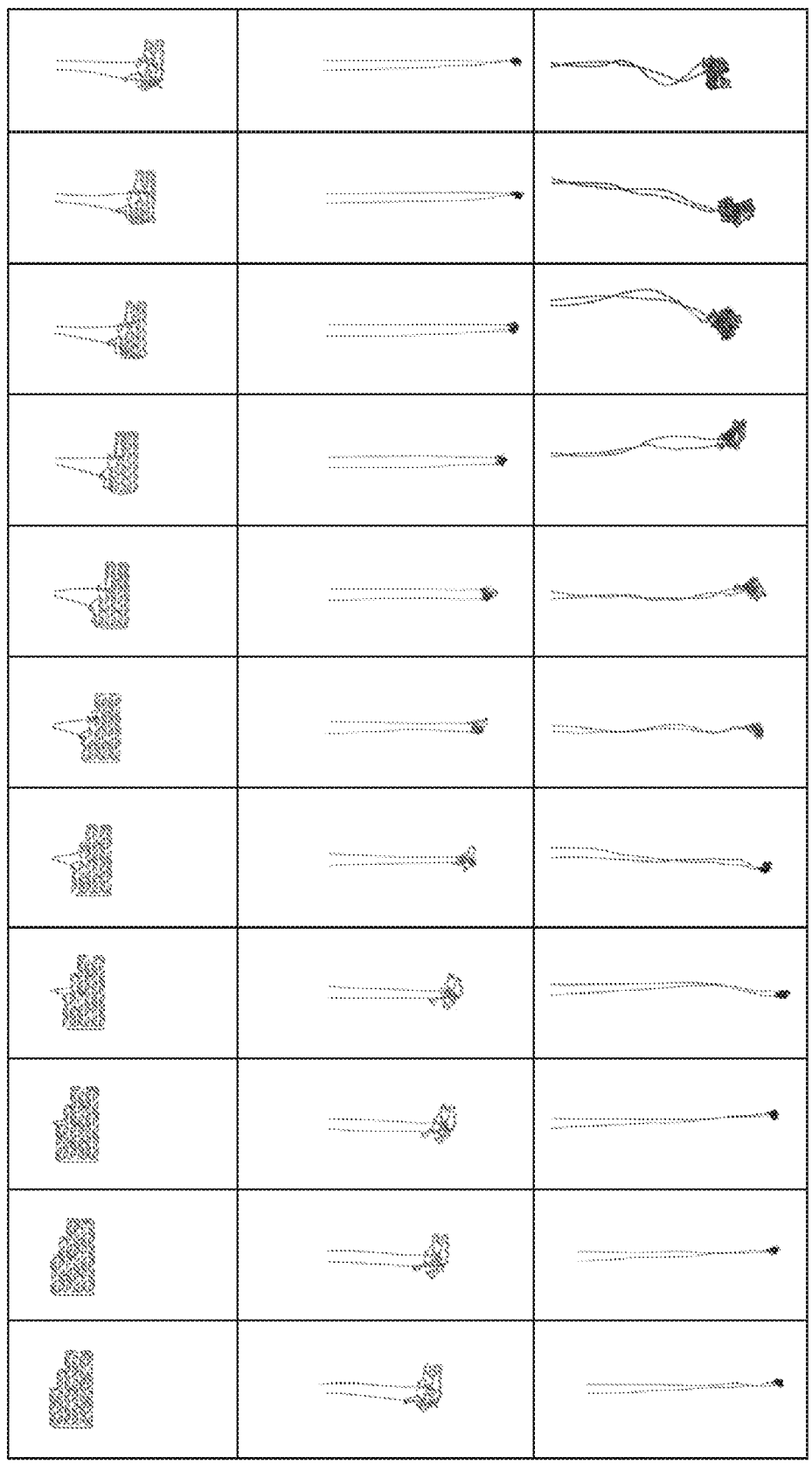
FIG. 28 provides selected screenshots of a dynamic knot relaxation process of an anti-parallel ssDNA nanostructure of the present disclosure.

This dynamic relaxation can be applied to an anti-parallel ssDNA nanostructure design (FIG. 19) with a crossing number of 63. The snapshot of the relaxation process is shown in FIG. 28. Different from all previous examples, such a high crossing number design will not be relaxed into a simple final shape, but instead a knotted ball. Folding of such a high crossing number pattern could be challenging.

Design of DNA with Crossing Number of Zero

As discussed herein, anti-parallel-crossover-based ssDNA nanostructure designs have high crossing numbers. At parallel crossover positions, DNA strands do not need to go through the central structure. Based on this assumption, if a ssDNA nanostructure design of the present disclosure contains only locking domains but not helical domains, DNA strands in this structure does not need to thread through the central plane. To achieve this goal, a folding pattern as shown in FIG. 29A was created, which has the maximum crossover points so that DNA strands never intertwine more than 180° on to the double helices before jumping to adjacent double helices. However, such simple folding pattern could also reduce the stability of the ssDNA nanostructure, as it contains a large number of unperturbed 5, 4 or even 1 base pair (bp) sections. In FIG. 29A, the wider cylinders contain 5 bp, the thinner cylinders contain 4 bp and the sections without a cylinder contain only 1 unperturbed continuous base paring. In experiments, one ssDNA nanostructure design was created with this pattern. This structure did not form and only linear unfolded DNA was observed under AFM imaging (data not shown).

Figure 29B:
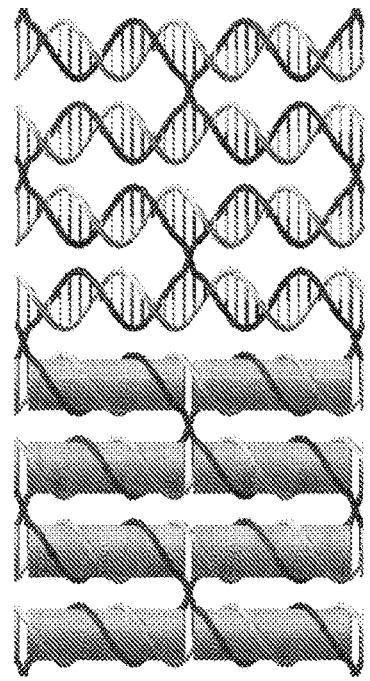

To remove 1 base pair sections, some of the crossover points were deleted. In FIG. 29B, a parallel ssDNA nanostructure design with 16-bp between adjacent crossovers was created, a similar crossover density to a conventional 2D multi-strand scaffold DNA nanostructure. This design strategy should be sufficiently stable since it contains only 16 bp unperturbed sections; however, it also results in a large crossing number despite that it uses only parallel crossovers. In this design, the light gray strand runs horizontally to tangle with both black and gray strands. Such entanglement cannot be eliminated by the aforementioned Reidemeister moves. To further examine its folding complexity, a ssDNA nanostructure design of the present disclosure based on this strategy was created (FIG. 30, top) and dynamic relaxation animation was applied to the structure. From the screenshots, the structure appears severely knotted.

Figure 29C:
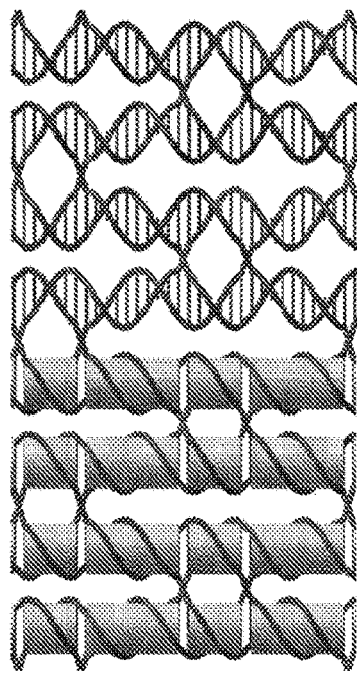
Figure 31:
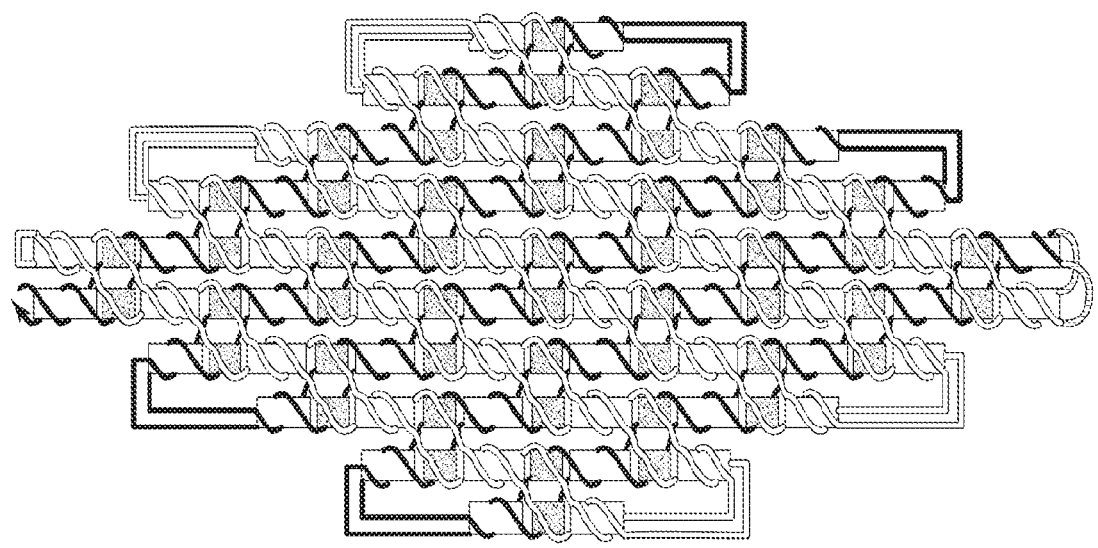
FIG. 31 shows a 5×5 ssDNA nanostructure of the present disclosure.

The final design adopts the design pattern shown in FIG. 29C, in which a putative, partially paired double-stranded intermediate is first formed and then folds into the final structure (FIG. 8C, 31).

Figure 32:
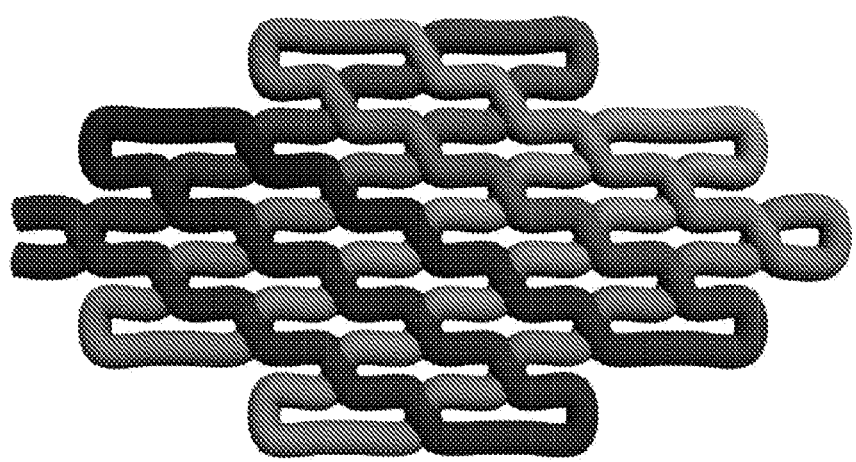
FIG. 32 shows a pipeline style model of a 5×5 ssDNA nanostructure of the present disclosure.

As shown in FIG. 21A, a helical double-stranded DNA has a crossing number of 0. The putative, partially paired double-stranded intermediate is similar to such a double-stranded DNA and can be treated as an unknotted structural unit (similar to FIG. 21A) for further folding. As such, the 5×5 plane containing all DNA helical axes, which could reduce the folding complexity of the ssDNA nanostructure design model can be illustrated with the simplified pipeline style model shown in FIG. 32. It is apparent that such a ssDNA nanostructure design is not knotted since the pipeline model never threads through any hole within the structure.

Figure 10:
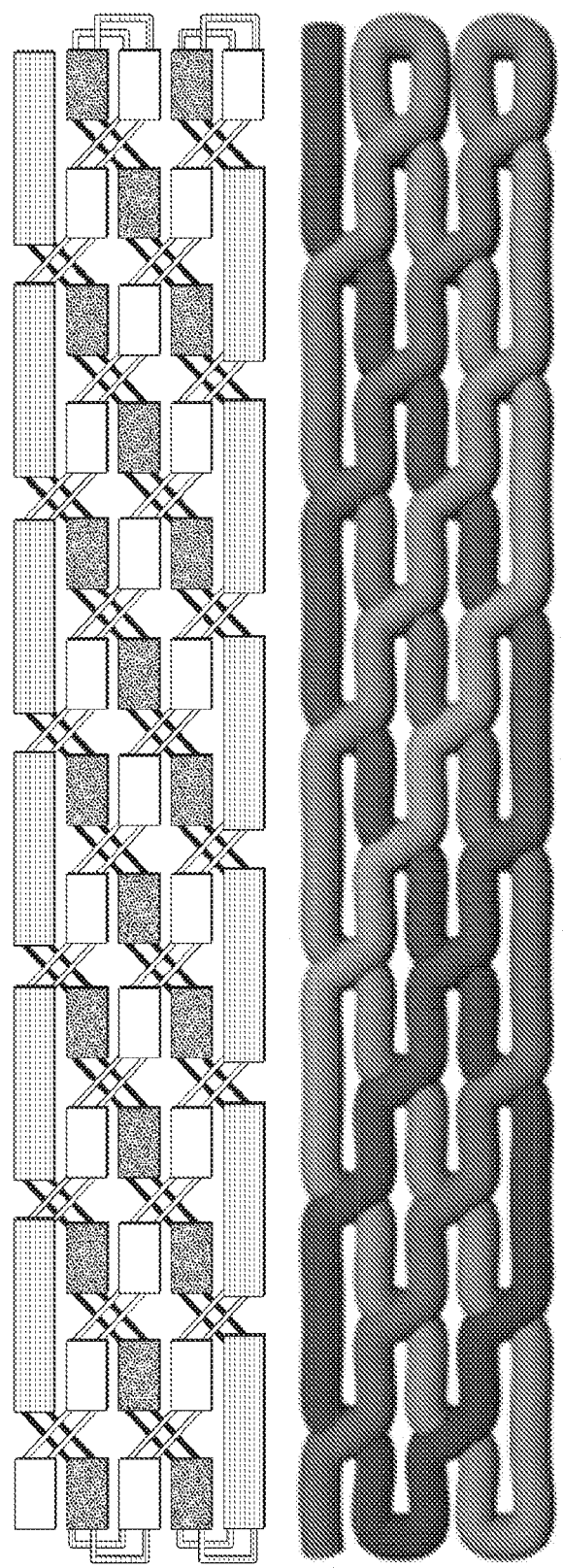
FIG. 10 shows cartoon (top) and pipeline style (bottom) models of a strip-shape ssDNA nanostructure. The long rectangles in the cartoon model represent 26 base pair (bp) helical domains.
Figure 11:
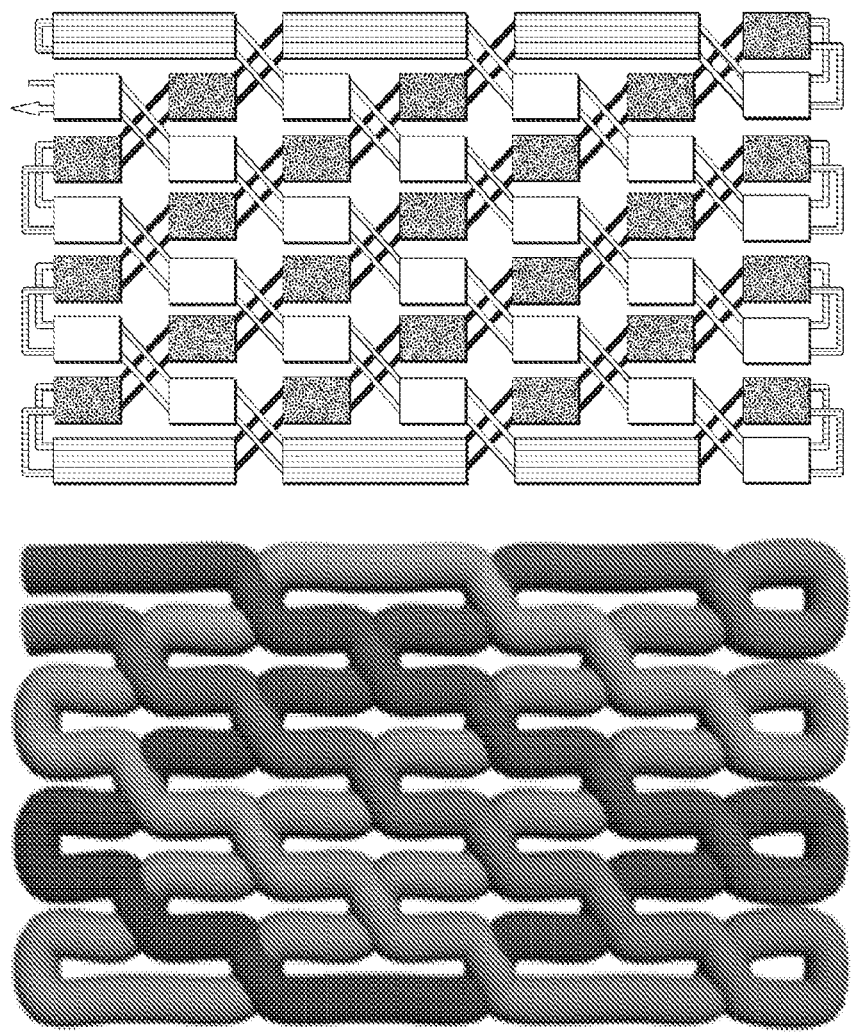
FIG. 11 shows cartoon (top) and pipeline style (bottom) models of a rectangle-shape ssDNA nanostructure. The long rectangles in the cartoon model represent 26 bp helical domains.
Figure 33:
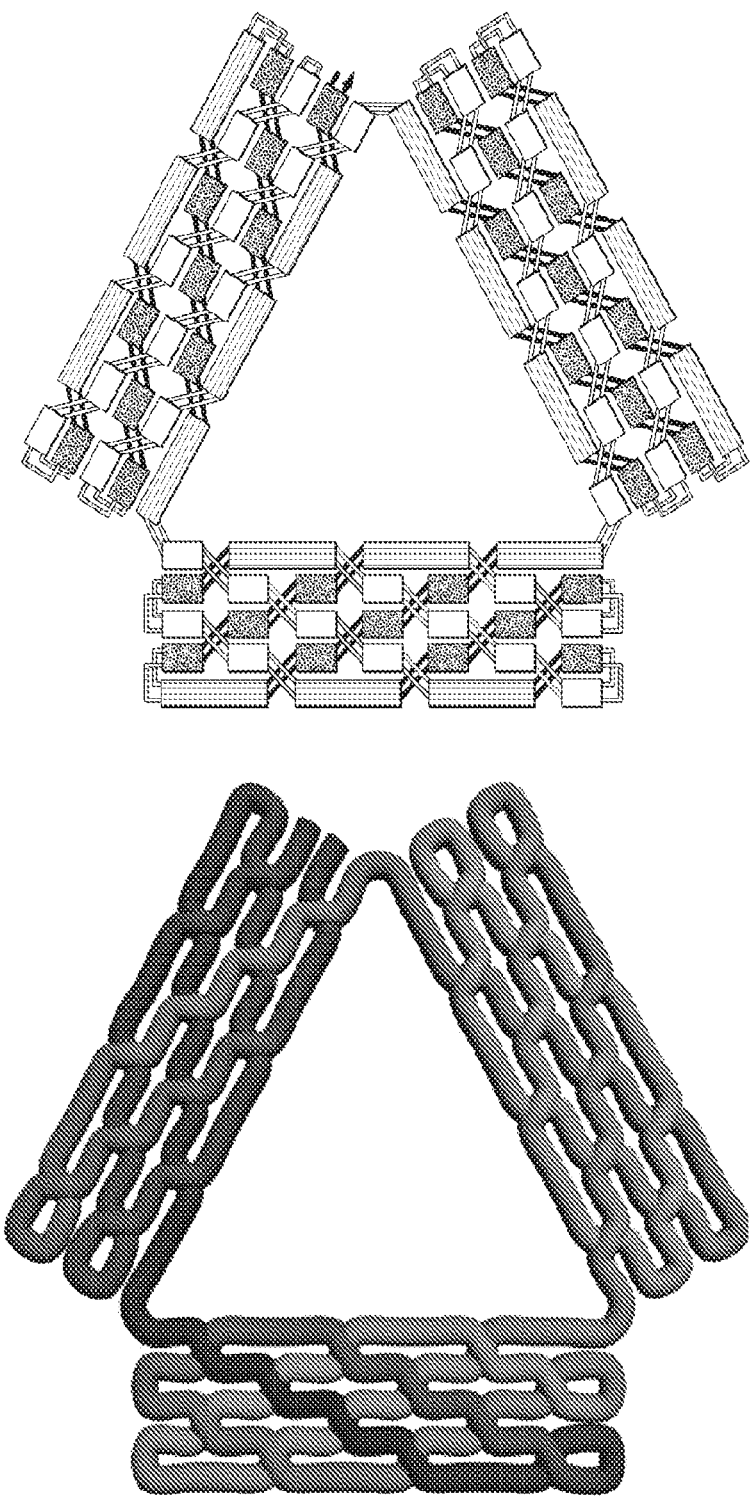
FIG. 33 shows cartoon (top) and pipeline style (bottom) model of a triangle-shape ssDNA nanostructure. The long rectangles in the cartoon model represent 26 bps helical domains.

Complex ssDNA nanostructures of the present disclosure are also achieved with similar helical and locking domain arrangements, such as those shown in FIGS. 10, 11, and 33. These designs contain 26 bps helical domains, indicated by the long rectangles in the cartoon model (top). As that synthesis of a DNA strand with many 26 bps complementary section is difficult, the synthesis DNA template was cut into two halves so that within each half of the strand there is no strong self-complementarity. As a result, such a DNA template becomes accessible via commercial synthesis.

Two single-stranded nucleic acids, or two regions of a single-stranded nucleic acid, are considered to be "parallel" relative to each other if they align parallel to each other in the same direction. By contrast, two single-stranded nucleic acids, or two regions of a single-stranded nucleic acid, are considered to be "anti-parallel" relative to each other if they align parallel to each other in the opposite direction. Thus, two complementary strands of a DNA double helix, for example, are antiparallel because they run in opposite directions to one another.

A "crossover position" herein refers to a position in a nucleic acid nanostructure at which two regions of a single-stranded nucleic acid intersect.

A "parallel crossover" herein refers to a crossover where the two unperturbed regions of a nucleic acid strand run parallel with each other.

An "anti-parallel crossover" herein refers to a crossover where the two unperturbed regions of a nucleic acid strand run anti-parallel with each other.

A ssDNA nanostructure is considered to contain "continuous π-π stacking along all helical domains" of the nanostructure if all nucleotide bases are fully paired with each other continuously without any nick points (breaking points).

Single-stranded DNA nanostructures produced in accordance with the present disclosure are typically nanometer-scale structures (e.g., having length scale of 1 to 1000 nanometers), although, in some instances, the term "nanostructure" herein may refer to micrometer-scale structures (e.g., assembled from more than one nanometer-scale or micrometer-scale structure). In some embodiments, a ssDNA nanostructure has a length scale of 1 to 1000 nm, 1 to 900 nm, 1 to 800 nm, 1 to 700 nm, 1 to 600 nm, 1 to 500 nm, 1 to 400 nm, 1 to 300 nm, 1 to 200 nm, 1 to 100 nm or 1 to 50 nm. In some embodiments, a ssDNA nanostructure has a length scale of greater than 1000 nm. In some embodiments, a ssDNA nanostructure has a length scale of 1 micrometer to 2 micrometers.

A single strand of DNA used for assembling a nanostructure in accordance with the present disclosure may vary in length. In some embodiments, a single strand of DNA has a length of 500 nucleotides to 10,000 nucleotides, or more. For example, a single strand of DNA may have a length of 500 to 9000 nucleotides, 500 to 8000 nucleotides, 500 to 7000 nucleotides, 500 to 6000 nucleotides, 500 to 5000 nucleotides, 500 to 4000 nucleotides, 500 to 3000 nucleotides, 500 to 2000 nucleotides, 500 to 1000 nucleotides, 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides. In some embodiments, a single strand of DNA may have a length of at least 2000 nucleotides, at least 3000 nucleotides, at least 4000 nucleotides, or at least 5000 nucleotides. In some embodiments, a single strand of DNA may have a length of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3100, 3200, 3300, 3400, 3500, 3600, 3700, 3800, 3900, 4100, 4200, 4300, 4400, 4500, 4600, 4700, 4800, 4900, 5100, 5200, 5300, 5400, 5500, 5600, 5700, 5800, 5900, 6600, 6200, 6300, 6400, 6500, 6600, 6700, 6800, 6900, 7100, 7200, 7300, 7400, 7500, 7600, 7700, 7800, 7900, 8100, 8200, 8300, 8400, 8500, 8600, 8700, 8800, 8900, 9100, 9200, 9300, 9400, 9500, 9600, 9700, 9800, 9900, or 10000 nucleotides. In some embodiments, a single strand of DNA assembled into a nanostructure, as provided herein, may have a length of 600 nucleotides to 4000 nucleotides. In some embodiments, a single strand of DNA assembled into a nanostructure, as provided herein, may have a length of 4000 nucleotides. A nanostructure assembled from a single strand of DNA having a length of approximately (e.g., ±10%) 4000 nucleotides has a molecular weight that is larger than 99.99% of all proteins in the human proteome.

Nanostructures of the present disclosure may further comprise loop domains that connect one helical domain to another helical domain and are located along the periphery of the nanostructure, as shown, for example, in FIG. 2A (outlined by a dotted the circled). Loop domains contain two unpaired single-strand regions of a DNA chain of the present disclosure.

The length of a loop domain may vary. In some embodiments, loop domains have a length of 10 to 100 nucleotides. For example, a loop domain may have a length of 10 to 50 nucleotides. In some embodiments, loop domains have a length of 10, 15, 20, 25, 30, 35, 40, 45, 50, 55, 60, 65, 70, 75, 80, 85, 90, 95 or 100 nucleotides. In some embodiments, loop domains have a length of 20 nucleotides.

Helical domains and locking domains are typically, but not necessarily, arranged in an alternating pattern. As an example, FIG. 2A depicts a two-layer nanostructure, each layer having helical domains separated by locking domains (internally) or helical domains separated by loop domains (peripherally). Thus, at least two helical domains of a ssDNA nanostructure are separated from each other by a (or at least one) locking domain. In some embodiments, 10%, 20%, 30%, 40%, 50%, 60%, 70%, 80%, 90%, 95%, 98%, or 100% of helical domains of a ssDNA nanostructure are separated from each other by a (or at least one) locking domain.

Nucleic acids of the present disclosure include DNA such as D-form DNA and L-form DNA and RNA, as well as various modifications thereof. Nucleic acid modifications include base modifications, sugar modifications, and backbone modifications.

Examples of modified DNA nucleic acids (e.g., DNA variants) that may be used in accordance with the present disclosure include, without limitation, L-DNA (the backbone enantiomer of DNA, known in the literature), peptide nucleic acids (PNA) bisPNA clamp, a pseudocomplementary PNA, locked nucleic acid (LNA), and co-nucleic acids of the above such as DNA-LNA co-nucleic acids. Thus, the present disclosure contemplates nanostructures that comprise DNA, RNA, LNA, PNA or combinations thereof. It is to be understood that the nucleic acids used in methods and compositions of the present disclosure may be homogeneous or heterogeneous in nature. As an example, nucleic acids may be completely DNA in nature or they may be comprised of DNA and non-DNA (e.g., LNA) monomers or sequences, as long as the nucleic acid used for the formation of a nanostructure is a single-stranded molecule. Thus, any combination of nucleic acid elements may be used. The nucleic acid modification may render the nucleic acid more stable and/or less susceptible to degradation under certain conditions. For example, in some embodiments, nucleic acids are nuclease-resistant.

Nucleic acids of the present disclosure, in some embodiments, have a homogenous backbone (e.g., entirely phosphodiester or entirely phosphorothioate) or a heterogeneous (or chimeric) backbone. Phosphorothioate backbone modifications may render an oligonucleotide less susceptible to nucleases and thus more stable (as compared to a native phosphodiester backbone nucleic acid) under certain conditions. Other linkages that may provide more stability to a nucleic acid of the present disclosure include, without limitation, phosphorodithioate linkages, methylphosphonate linkages, methylphosphorothioate linkages, boranophosphonate linkages, peptide linkages, alkyl linkages and dephospho-type linkages. Thus, in some embodiments, nucleic acids have non-naturally occurring backbones.

In some embodiments, a single strand of DNA of the present disclosure does not encode a product (e.g., a protein). In some embodiments, a single strand of DNA of the present disclosure does encode a product (e.g., a protein).

Synthesis of Single-Stranded DNA

Also provided herein are methods of producing a single strand of DNA, for example, for use in producing a ssDNA nanostructure. Unlike previous multi-stranded DNA nanostructures, which typically contain dozens or hundreds of distinct (nucleic acid) components and often undesirable defects such as missing or incorrect component strands, the system provided herein is a homogenous system, because it has only one component strand that can be synthesized with high purity. Unimolecular folding of ssDNA eliminates stoichiometry issues and waste staple strands that are present in traditional multi-strand systems. Additionally, the intramolecular folding yield of one piece of DNA is independent of the reactant concentration; this differs from the concentration-dependent intermolecular self-assembly of traditional multi-strand systems. Similarly, the folding of a ssDNA of the present disclosure has concentration-independent, robust folding kinetics. Furthermore, a ssDNA, being one single strand, can be amplified by polymerase in a single pass. As shown in the Examples, a folded ssDNA nanostructure can be melted and used as a template for amplification in vitro by polymerases.

Figure 2B:
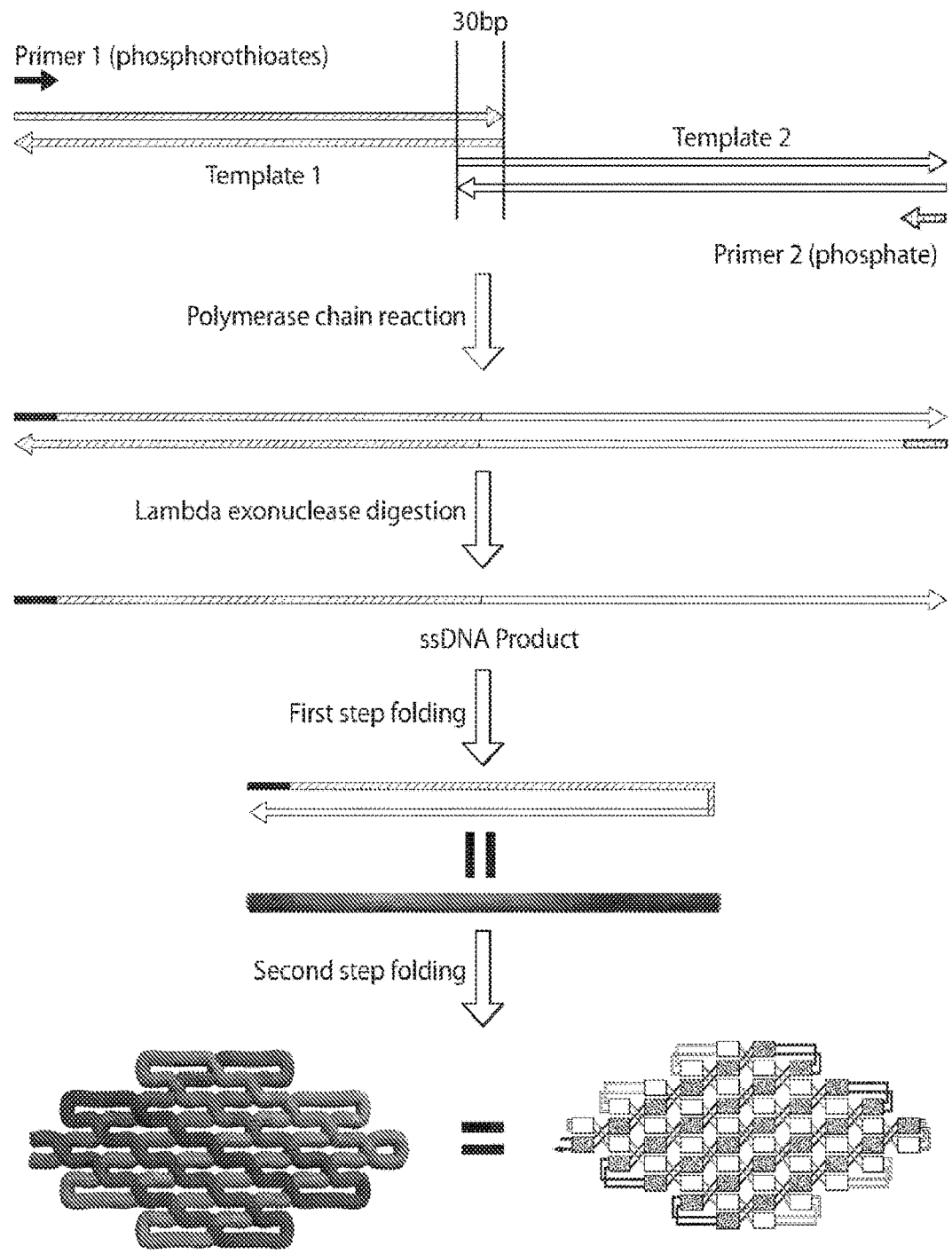
FIG. 2B schematizes an example of a method of synthesis of a single strand of ssDNA and subsequent assembly into a nanostructure, in accordance with the present disclosure.

For example, two chemically modified nucleic acid primers (phosphorothioate for primer 1 and phosphate for primer 2) may be used for amplification of a single strand of DNA, as depicted in FIG. 2B. Considering the large fraction of self-complementary within a single strand of DNA of the present disclosure, which dramatically increases the difficulty in DNA synthesis, the present disclosure contemplates the initial separation of the single stranded DNA is separated into two halves with a 10 to 50 (e.g., 10, 15, 20, 25, 30, 35, 40, 45 or 50) base pair sequence overlap in the middle (as shown in FIG. 2B). A polymerase chain reaction, for example, connects the two halves into one piece of double-stranded DNA during the amplification process (FIG. 2B). Because the phosphorothioate modification on primer 1 renders the internucleotide linkage resistant to nuclease degradation, while phosphorylation on primer 2 makes the reverse strand a substrate for DNA ligase, only the second strand of the double helix will be digested by lambda exonuclease, leaving the protected single strand of DNA for further folding (FIG. 2B). The self-assembly of the single strand of DNA is design to occur in two steps in a typical annealing process. In the first step (at higher temperature), ssDNA will fold back onto itself because of its self-complement helical domains (FIG. 2B). This intermediate is demonstrated with a shaded gradient in which the 5' and 3' ends are shown to the left and the turning point of the ssDNA is shown to the right. In the second step (at lower temperature), unpaired single strand regions in locking domains self-assemble with their counterparts, and finally leads to a well-formed nanostructure.

An annealing reaction for producing a well-formed ssDNA nanostructure in accordance with the present disclosure may occur in a single vessel such as, but not limited to, a tube, a well or a vial. In some embodiments, the ssDNA is placed in a solution. The solution may be buffered, although the annealing reaction can also occur in the absence of buffer. The solution may further comprise divalent cations such as, but not limited, to $Mg^{2+}$. The cation or salt concentration may vary. The solution may also comprise EDTA or other nuclease inhibitors in order to prevent degradation of the single strand of DNA.

An annealing reaction is carried out, in some embodiments, by heating the solution containing the single strand of DNA and then allowing the solution to slowly cool down (e.g., heated and then placed in a room temperature environment). The temperature of the reaction should be sufficiently high to melt any undesirable secondary structure such as hairpin structures and to ensure that the single strand of DNA is not folded incorrectly. The temperature, therefore, may be initially raised to any temperature below or equal to 100° C. For example, the temperature may be initially raised to 100° C., 95° C., 90° C., 85° C., 80° C., 75° C., 70° C., 65° C. or 60° C. The temperature may be raised by placing the vessel in a hot water bath, heating block or a device capable of temperature control, such as a thermal cycler (e.g., polymerase chain reaction (PCR) machine). The vessel may be kept in that environment for seconds or minutes. In some embodiments, an incubation time of about 1-10 minutes is sufficient.

Once nucleic acid incubation at an elevated temperature is complete, the temperature may be dropped in a number of ways. The temperature may be dropped, for example, in an automated manner using a computer algorithm that drops the temperature by a certain amount and maintains that temperature for a certain period of time before dropping the temperature again. Such automated methods may involve dropping the temperature by a degree in each step or by a number of degrees at each step. The vessel may thus be heated and cooled in the same device. As another example, the heated solution may be placed at room temperature to cool.

In some embodiments, a single strand of DNA is heated to a temperature of 85° C. to 95° C., and then progressively cooled to a temperature of 20° C. to 37° C., thereby producing the nanostructure. In some embodiments, methods of the present disclosure comprise heating a single strand of DNA to a temperature of 80° C., 85° C., 90° C., or 95° C. In some embodiments, methods of the present disclosure comprise cooling a single strand of DNA to a temperature of 20° C., 25° C., 30° C. or 35° C.

In some embodiments, methods comprise heating a single strand of DNA for 1 minute to 15 minutes (min), and then cooling the DNA for 90 min to 180 min. For example, a single strand of DNA may be heated for 1 min, 2 min, 3 min, 4 min, 5 min, 6 min, 7 min, 8 min, 9 min, 10 min, 11 min, 12 min, 13 min, 14 min, 15 min or more. In some embodiments, a single strand of DNA is heated for 1 to 30 min. In some embodiments, a single strand of DNA is then cooled (e.g., progressively cooled) for 30 min to 180 min. For example, a single strand of DNA may be cooled for 30 min, 40 min, 50 min, 60 min, 70 min, 80 min, 90 min, 100 min, 110 min, 120 min, 130 min, 140 min, 150 min, 160 min, 170 min or 180 min. In some embodiments, a single strand of DNA is heated for 10 min, and then cooled for 120 min.

Figure 7A:
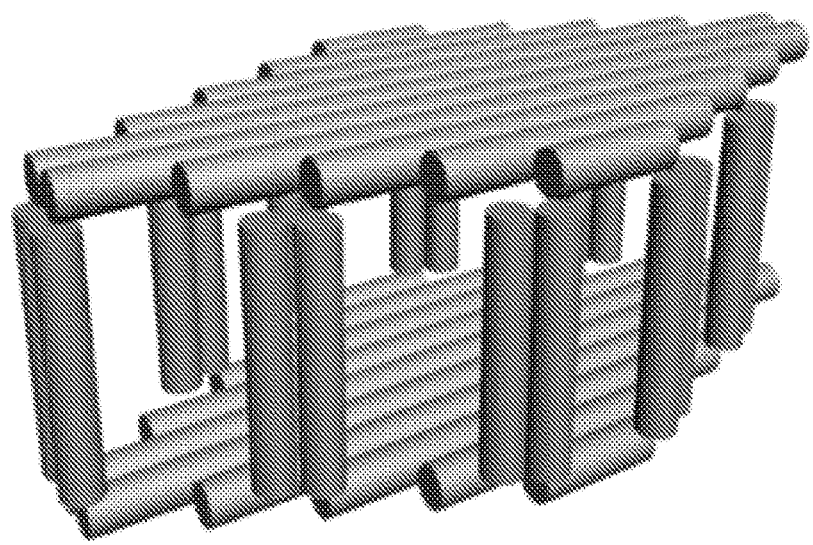
FIGS. 7A and 7B show a three-dimensional cartoon model (FIG. 7A) and a double helical model (FIG. 7B) for drug encapsulation.
Figure 7B:
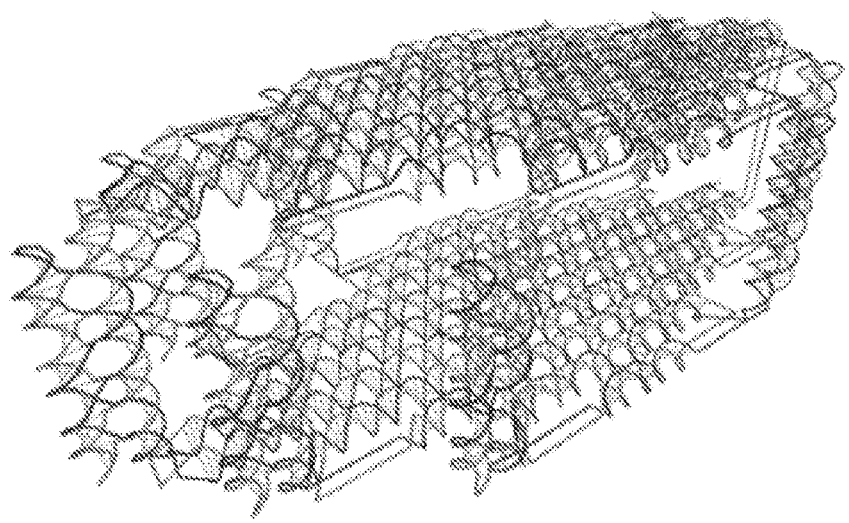
Figure 7C:
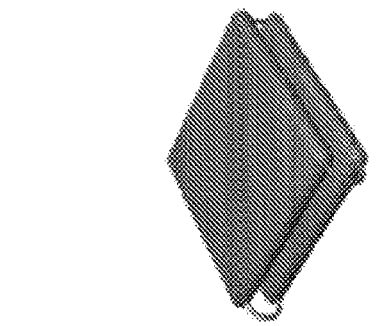
FIGS. 7C-7J show schematics of "AND" logic (FIGS. 7C-7F) and "OR" logic (FIGS. 7G-7J) ssDNA "containers" with two different peptide clasps (scissors) and their corresponding target proteases (light gray: e.g., MMP-2; dark gray: e.g., MMP-9).
Figure 7D:
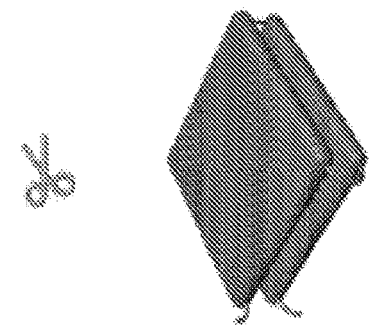
Figure 7E:
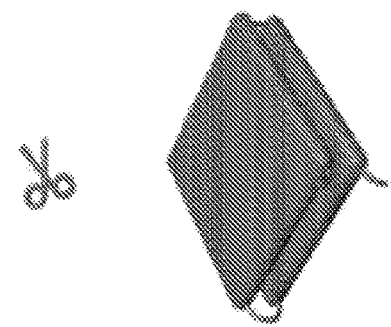
Figure 7F:
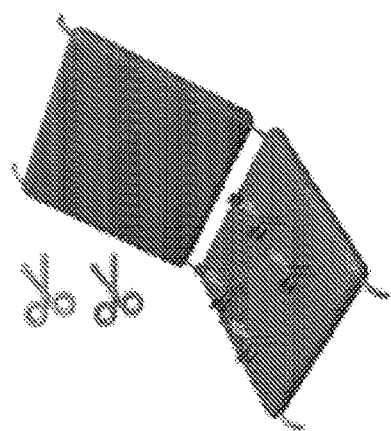
Figure 7G:
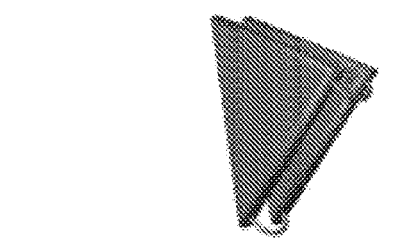
Figure 7H:
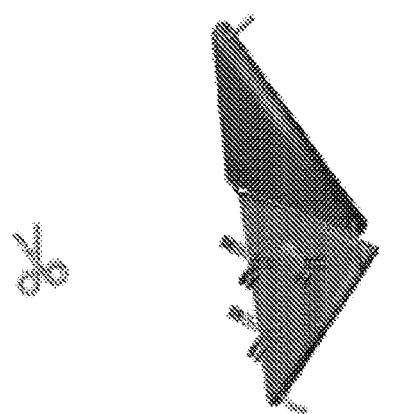
Figure 7I:
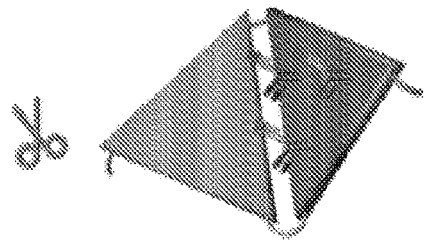
Figure 7J:
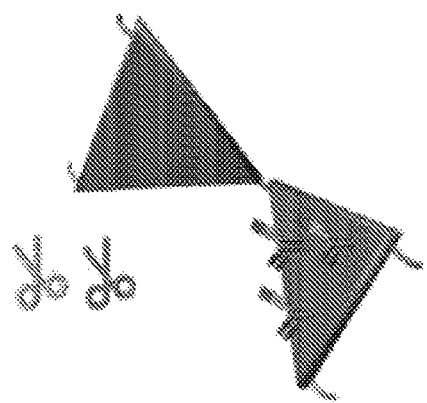

Applications ssDNA nanostructures of the present disclosure may be used as therapeutics, or therapeutic delivery vehicles, for a multitude of biomedical applications, including cancer therapy and immunotherapy. Single-stranded DNA (ssDNA) nanostructures can be used, for example, to organize various agents (e.g., proteins, such as antibodies) with controlled spatial distance. FIGS. 6A-6F depict ssDNA nanostructures designs having various arrangements of therapeutic antibodies (e.g., stimulatory agonist antibodies and inhibitory antibodies, such as ipilimumab/nivolumab).

ssDNA nanostructures of the present disclosure may be used as "containers" that encapsulate therapeutic agents (e.g., antibodies) and deploy them specifically in the vicinity of a tissue in vivo (e.g., a tumor) using, for example, targeting peptides (e.g., tumor targeting peptides). In response to the tumor micro-environment, for example, ssDNA containers will reconfigure to reveal initially hidden therapeutic antibodies, reducing off-target toxicity. This environmentally-responsive reconfiguration can be achieved by incorporating peptide 'clasps' that are degraded by proteases which have increased expression in the tissue (e.g., tumor) microenvironment. FIGS. 7A-7B show an example of a ssDNA container. Two diamond-shaped domains are covalently attached in the rear vertex by two single-stranded scaffold hinges, and their edges are connected by nine paranemic-crossover (PX) double helices.

ssDNA nanostructures of the present disclosure may be used to construct nanocontainers with different algorithms for target recognition, each with its own drug and programmed set of inputs for drug release. Upon detection of different disease markers, such as matrix metalloproteinase-2 (MMP-2) and MMP-9, the proper drug can be released through a programmed response. Two of the very basic Boolean logic gates, AND gate (when both keys are presented, drug will be released) and OR Gate (either of the two keys are sensed, drug will be released) are designed as shown in FIGS. 7C-7J. An example of the closed state of a ssDNA nanostructure AND logic container is shown in FIG. 7C. The main body of the container is designed to be a rectangle-sandwich shape, in which two vertexes of the rectangle in the back of the image are covalently linked by ssDNA backbone hinges, and the other two are covalently fastened by two different peptide clasps, which are targets for, for example, MMP-2 and MMP-9 separately. For this AND logic container design, when either of the two target protease is presented as shown in FIGS. 7D and 7E, the corresponding peptide will be cut and opened. However, the ssDNA container will remain a close state if the other clasp is intact in this design. Only when both target proteases are presented in a tumor microenvironment, for example, the two different peptide clasps can be both opened and only then will the ssDNA container expose its initially hidden therapeutic agent (FIG. 7F). Both stimulatory and inhibitory antibodies can be encapsulated into the container so that targeted combination immunotherapy can be achieved in this manner, for example.

The specificity of ssDNA containers can be tuned by varying the clasp sequence and by changing the container design. For example, to make it harder for a tumor to alter protease expression and escape targeting, the clasps can be engineered with OR logic—the container deploys the immunotherapy when either one of the proteases is present (FIGS. 7G-7J). For this purpose, ssDNA contains can be designed with a triangle-sandwich shape. This container has one ssDNA backbone linkage in the back vertex plus two different peptide clasps in the front. The triangle geometry ensures that when either or both of the two peptide clasps are cut and opened, the hidden cargo will be exposed.

Single-stranded DNA nanostructures of the present disclosure were constructed from a ssDNA with synthetic sequence ranging in length from ~1,000 nt to ~4,000 nt, for example, which represents the largest unimolecular folding of a synthetic DNA structure achieved to date. Compared to the wire-frame DNA octahedron assembled from a 1,700 nt scaffold strand and several auxiliary short strands reported in 2004[7], the ssDNA nanostructures of the present disclosure contain no auxiliary strands and can be designed to form a wide variety of space-filling compact shapes. The ssDNA nanostructures of the present disclosure are purely de novo-designed structured that does not rely on the availability of highly sequence-specific, naturally occurring molecular interaction motifs with defined geometrical arrangements (e.g., the RNA kissing loops), and thus are more easily designed and scalable, as shown by the construction of, for example, a 4,000 nt ssDNA nanostructure.

As a homogenous system, the ssDNA of the present disclosure has unique advantages in diverse applications due to its intrinsic purity and high folding yield, e.g., for applications (e.g., in photonics, materials, etc.) that require very high precision of placing particular functional molecular entities. The large-scale cost-efficient production of ssDNA nanostructures via in vivo amplification make it sufficiently affordable to enable therapeutic applications such as targeted drug delivery, which requires large amounts of homogeneous materials.

The present disclosure further encompasses the following numbered paragraphs:

1. A nanostructure formed from nucleic acid consisting of a single strand of DNA rationally-designed to self-assemble into a hairpin loop, helical domains, and locking domains.

2. The nanostructure of paragraph 1, wherein the nanostructure comprises:
   a first layer containing helical domains and locking domains, wherein at least two helical domains of the first layer are separated from each other by a locking domain; and
   a second layer comprising helical domains and locking domains, wherein at least two helical domains of the second layer are separated from each other by a locking domain,
   wherein a locking domain of the first layer is hybridized to a locking domain of the second layer.

3. The nanostructure of paragraph 1 or 2, wherein the single strand of DNA has a length of 500 nucleotides to 10,000 nucleotides.

4. The nanostructure of paragraph 3, wherein the single strand of DNA has a length of 2,000 nucleotides to 5,000 nucleotides.

5. The nanostructure of any one of paragraphs 1-4, wherein the helical domains have a length of 10 to 50 nucleotides.

6. The nanostructure of paragraph 5, wherein the helical domains have a length of 10 to 30 nucleotides.

7. The nanostructure of paragraph 6, wherein the helical domains have a length of 10 nucleotides.

8. The nanostructure of any one of paragraphs 1-7, wherein the locking domains have a length of 4 to 20 nucleotides.

9. The nanostructure of paragraph 8, wherein the locking domains have a length of 5 to 10 nucleotides.

10. The nanostructure of paragraph 9, wherein the locking domains have a length of 6 nucleotides.

11. The nanostructure of any one of paragraphs 1-10 further comprising loop domains that connect one helical domain to another helical domain and are located along the periphery of the nanostructure.

12. The nanostructure of paragraph 11, wherein the loop domains have a length of 10 to 100 nucleotides.

13. The nanostructure of paragraph 12, wherein the loop domains have a length of 10 to 50 nucleotides.

14. The nanostructure of paragraph 13, wherein the loop domains have a length of 20 nucleotides.

15. The nanostructure of any one of paragraphs 1-14, wherein the crossing number of the nanostructure is zero and the nanostructure is unknotted.

16. The nanostructure of any one of paragraphs 1-15, wherein the nanostructure contains only parallel crossovers.

17. The nanostructure of any one of paragraphs 1-16, wherein the nanostructure contains continuous π-π stacking along greater than 50% of the helical domains of the nanostructure.

18. A composition comprising the nanostructures of any one of paragraphs 1-17.

19. A method of producing the nanostructure of any one of paragraphs 1-17, the method comprising incubating the single strand of DNA under conditions that result in the formation of the nanostructure.

20. A method of producing the nanostructure of any one of paragraphs 1-17, the method comprising:
  (a) combining in a single reaction mixture
    (i) a first DNA template and a second DNA template, wherein the templates comprise end sequences that overlap with each other,
    (ii) a first primer having a phosphorothioate modification, wherein the first primer binds to the end of the first DNA template that is opposite to the overlapping end sequences,
    (iii) a second primer having a phosphate modification, wherein the second primer binds to the end of the second DNA template that is opposite to the overlapping end sequences, and
    (iv) polymerase;
  (b) performing on the single reaction mixture a nucleic acid amplification reaction, thereby producing amplified DNA;
  (c) exposing the amplified DNA to exonuclease digestion, thereby producing a single strand of DNA; and
  (d) heating the single strand of DNA to a temperature of 85° C. to 95° C., and then progressively cooling the single strand of DNA to a temperature of 20° C. to 37° C., thereby producing the nanostructure.

21. The method of paragraph 19 or 20, wherein the single strand of DNA is heated for 1 min to 15 min, and then cooled for 90 min to 180 min.

22. The method of paragraph 19 or 20, wherein the single strand of DNA is heated for 10 min, and then cooled for 120 min.

23. The method of any one of paragraphs 20-22, wherein the exonuclease is lambda exonuclease.

24. A single strand of DNA rationally-designed to self-assemble into a nanostructure containing a hairpin loop, helical domains, and locking domains.

25. The single strand of DNA of paragraph 24, wherein the nanostructure comprises:
  a first layer containing helical domains and locking domains, wherein at least two helical domains of the first layer are separated from each other by a locking domain; and
  a second layer comprising helical domains and locking domains, wherein at least two helical domains of the second layer are separated from each other by a locking domain,
  wherein a locking domain of the first layer is hybridized to a locking domain of the second layer.

26. The single strand of DNA of paragraph 24 or 25, wherein the single strand of DNA has a length of 500 nucleotides to 10,000 nucleotides.

27. The single strand of DNA of paragraph 26, wherein the single strand of DNA has a length of 2,000 nucleotides to 5,000 nucleotides.

28. The single strand of DNA of any one of paragraphs 24-27, wherein the helical domains have a length of 10 to 50 nucleotides.

29. The single strand of DNA of paragraph 28, wherein the helical domains have a length of 10 to 30 nucleotides.

30. The single strand of DNA of paragraph 29, wherein the helical domains have a length of 10 nucleotides.

31. The single strand of DNA of any one of paragraphs 24-30, wherein the locking domains have a length of 4 to 20 nucleotides.

32. The single strand of DNA of paragraph 31, wherein the locking domains have a length of 5 to 10 nucleotides.

33. The single strand of DNA of paragraph 32, wherein the locking domains have a length of 6 nucleotides.

34. The single strand of DNA of any one of paragraphs 24-29 further comprising loop domains that connect one helical domain to another helical domain and are located along the periphery of the nanostructure.

35. The single strand of DNA of paragraph 34, wherein the loop domains have a length of 10 to 100 nucleotides.

36. The single strand of DNA of paragraph 35, wherein the loop domains have a length of 10 to 50 nucleotides.

37. The single strand of DNA of paragraph 36, wherein the loop domains have a length of 20 nucleotides.

38. A method of producing the single strand of DNA of any one of paragraphs 24-37, the method comprising:
  (a) combining in a single reaction mixture
    (i) a first DNA template and a second DNA template, wherein the templates comprise end sequences that overlap with each other,
    (ii) a first primer having a phosphorothioate modification, wherein the first primer binds to the end of the first DNA template that is opposite to the overlapping end sequences,
    (iii) a second primer having a phosphate modification, wherein the second primer binds to the end of the second DNA template that is opposite to the overlapping end sequences, and
    (iv) polymerase;
  (b) performing on the single reaction mixture a nucleic acid amplification reaction, thereby producing amplified DNA; and
  (c) exposing the amplified DNA to exonuclease digestion, thereby producing a single strand of DNA.

EXAMPLES

Example 1

Figures 3C, 3D:
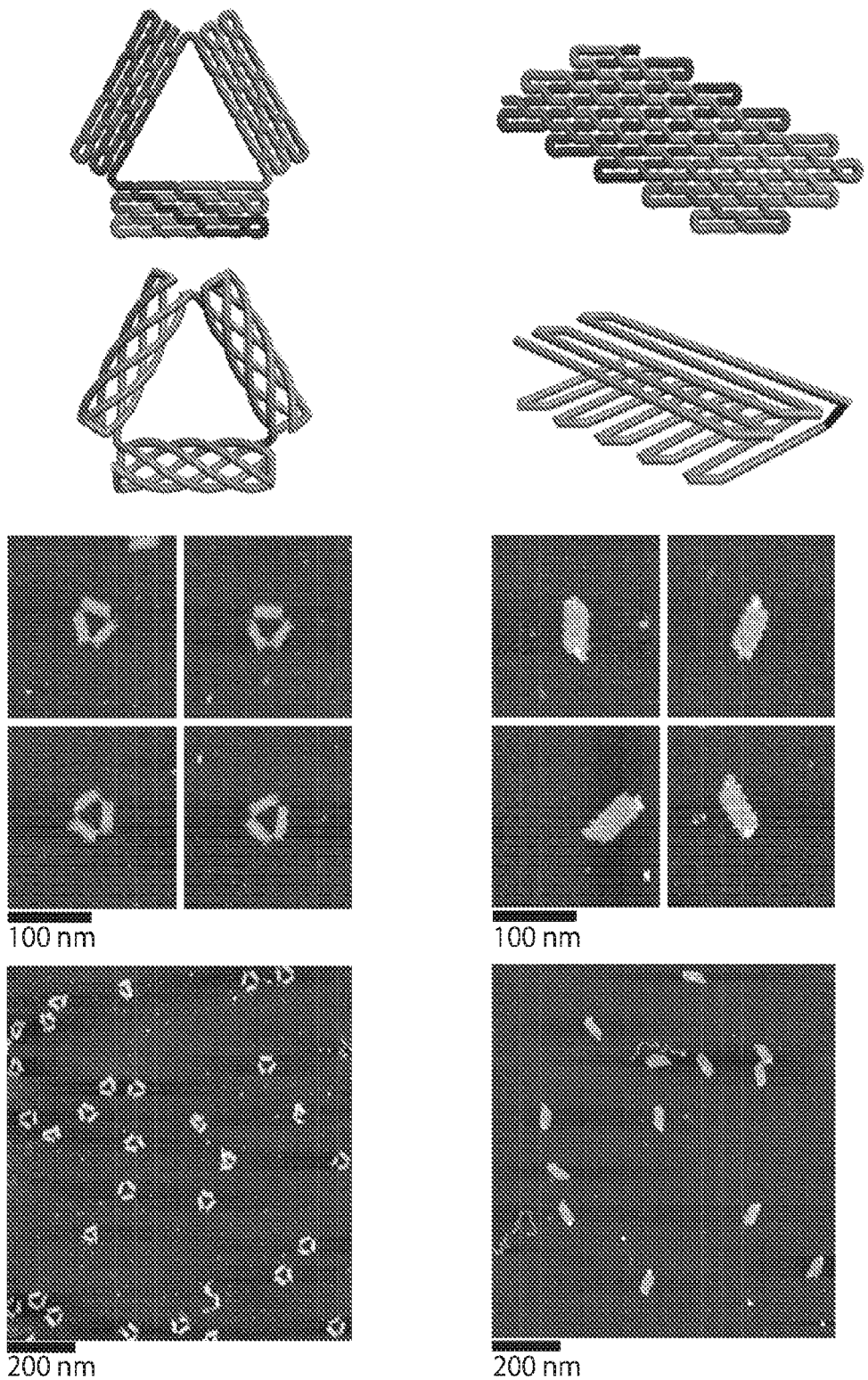

Four different ssDNA nanostructures of the present disclosure are shown in FIGS. 3A-3D. Three-dimensional (3D)

models indicating helical and locking domains are depicted in the top panels; 3D models showing the track of partially formed double strand intermediates are depicted in the middle panels; and atomic force microscopy (AFM) images are depicted in the bottom panels. FIG. 3A depicts is a diamond-shape structure, which contains 2170 nucleotides. The double-strand intermediate starts from the left side of the design in the cylinder model. It folds back and forth in a raster-filling pattern on the back of the design and goes to the top layer, starting from the vertex on the right of the model. FIG. 3B depicts a triangle-shape structure (3547 nt) with three arms that self-assemble independently. The starting and ending points of the track are both in the bottom arm of the triangle, and the double-strand intermediate travels between the bottom layer and the top layer several times in each arm without any topological entanglement. On the edges/periphery of each arm, 11 nucleotide loop domains are used for connection purposes. FIGS. 3C and 3D respectively depict the formation of a rhomboid-shape and a ribbon-shaped structure, each of which contain 4000 nucleotides, which is larger than 99.99% of all proteins in the human proteome and three times the size of the largest catalytic rRNA (16S rRNA).

Figure 3E:
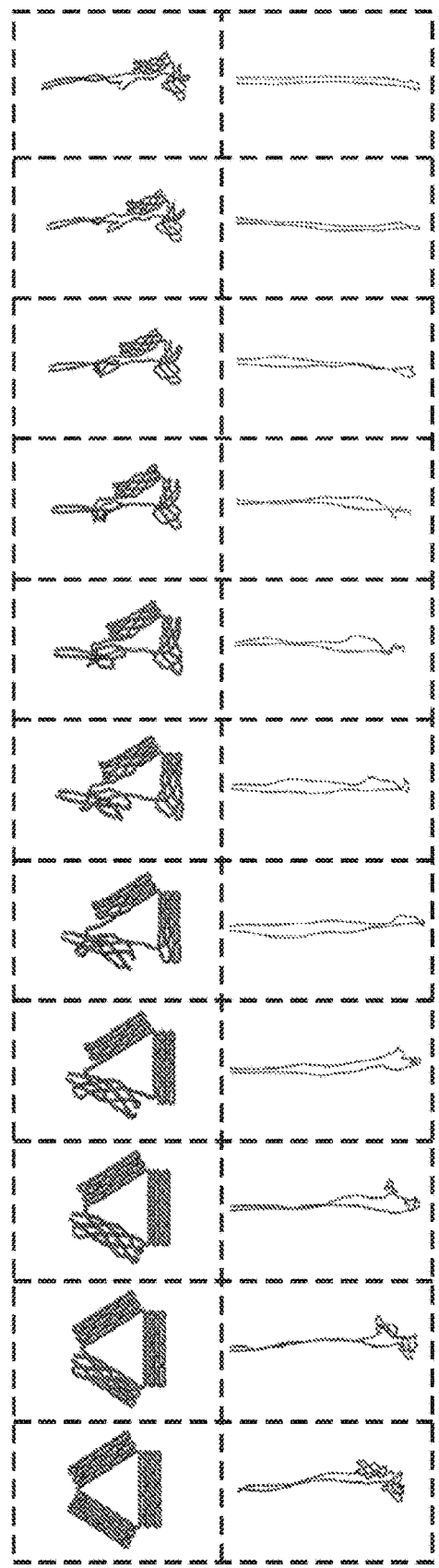
Figure 12:
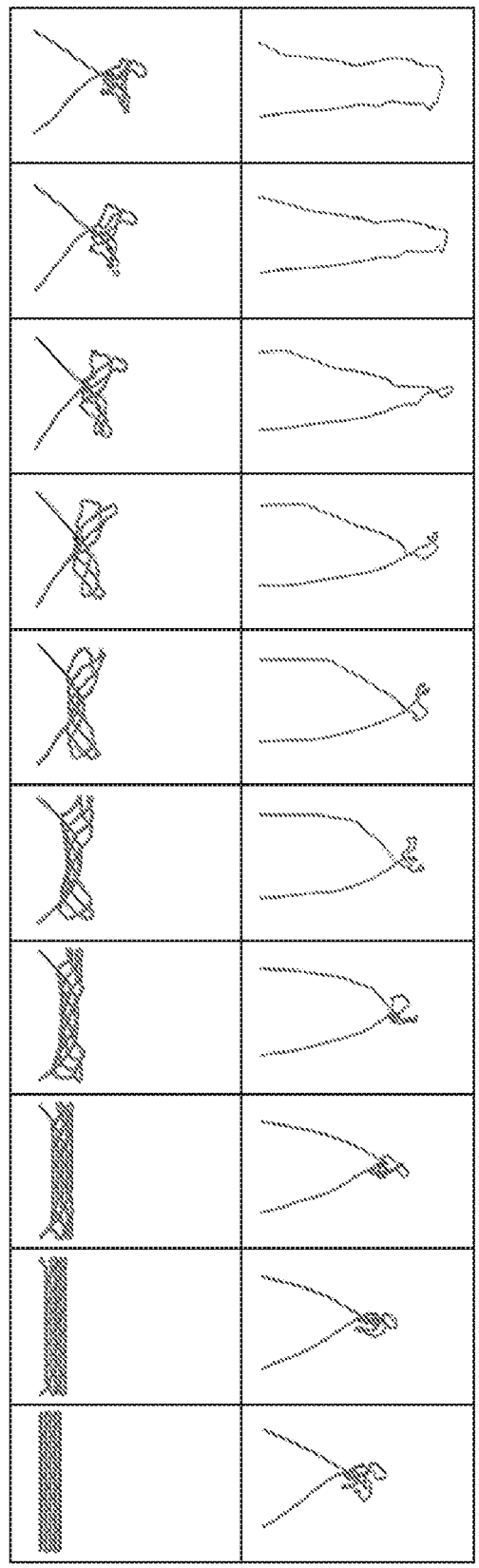
FIG. 12 shows selected screenshots of a dynamic knot relaxation process for a strip-shape ssDNA nanostructure.
Figure 13:
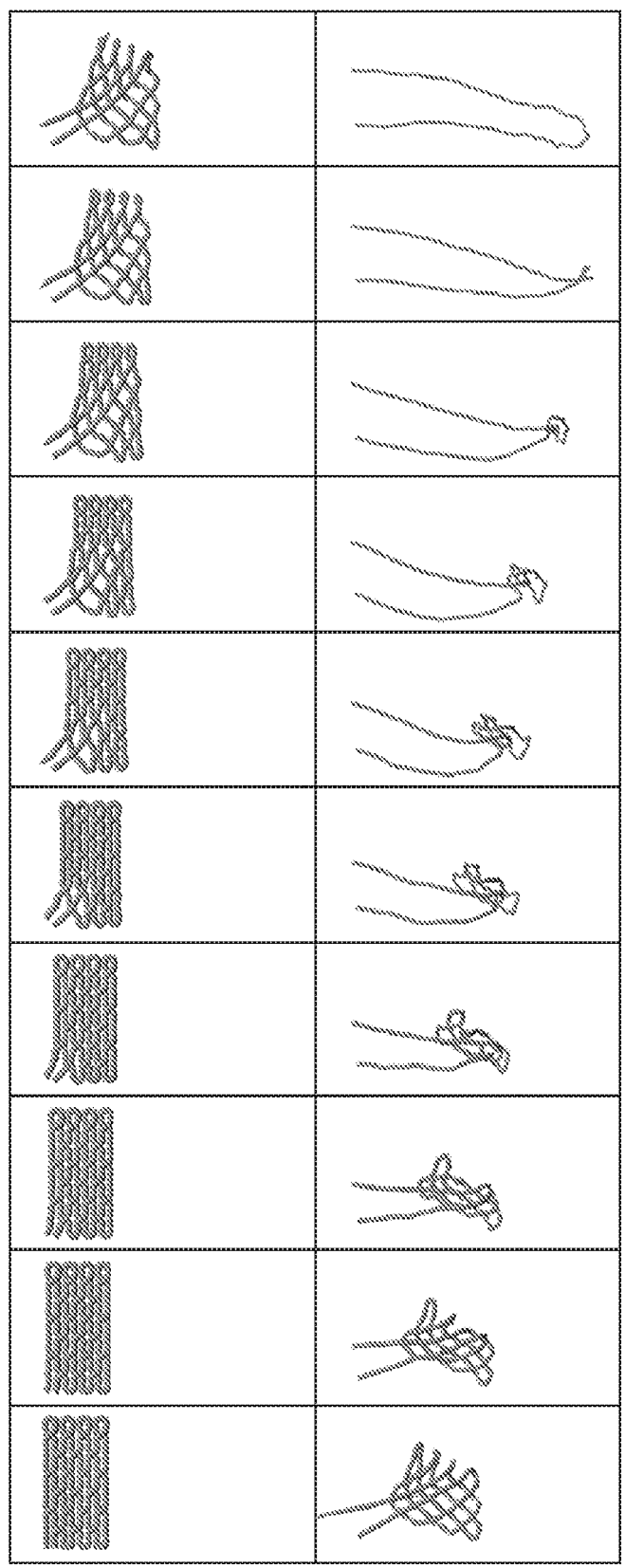
FIG. 13 shows selected screenshots of a dynamic knot relaxation process for a rectangle-shape ssDNA nanostructure.

To further demonstrate the versatility of a ssDNA design strategy, several additional ssDNA designs with different geometries were tested. First, two rectangle-shaped ssDNA designs in which the putative double-stranded intermediate wraps along the helical direction several times instead of raster-filling the bottom and top layers. Importantly, this change does not increase the global crossing number of the design (FIGS. 3A-3B). Another difference between rectangle-shaped ssDNA and diamond-shaped ssDNA is that the rectangular design contains several 26 bp helical domains on its long edges (FIGS. 10-11), which bridge the bottom and the top layer strands. Triangle-shaped ssDNA was also created (FIG. 3C). While these designs appear to have more structural complexity, their crossing number remains 0 as verified by dynamic relaxation (FIGS. 3E, 12, and 13). Additionally, a 5×10 rhomboid shape design demonstrating the successful folding of a 3,940 nt ssDNA was tested (FIG. 3D). According to SwissProt database (a subset of the Uniprot database), this structure would be the third largest in the human proteome, based on its molecular weight. The sequences for all ssDNA nanostructures of the present disclosure are provided herein.

Example 2

Single-stranded DNA nanostructures having different sizes were assembled and are shown in FIGS. 4A-4C. Three diamond shape nanostructures containing 1 k, 1.6 k and 2.3 k nucleotides (nt) are shown and were obtained with high yield.

A two-layer design strategy can be applied to diamond-shaped ssDNA nanostructures with variable sizes. Based on the number of pipeline sections in the two layers, m×n ssDNA nanostructures have been created successfully (m denotes the number of diagonally oriented, partially-paired helices in the top layer and n denotes number of partially-paired helices in the bottom layer) such as the 3×3, 4×4 and 5×5 ssDNA nanostructures of the present disclosure which are shown in FIGS. 4A-4C. For example, the 3×3 structure (FIG. 4A) contains 9 locking domains in the design and the 5×5 structure (FIG. 4C) contains 25 locking domains. When all the locking domains are correctly paired in the folding process, a well-folded ssDNA nanostructure is produced. FIGS. 4A-4C show the pipeline-style models of these structures and the corresponding AFM images. These ssDNA nanostructures were folded in 12.5 mM $Mg^{2+}$ buffer using a 2 hour annealing ramp from 85° C. to 25° C.

Figure 5A:
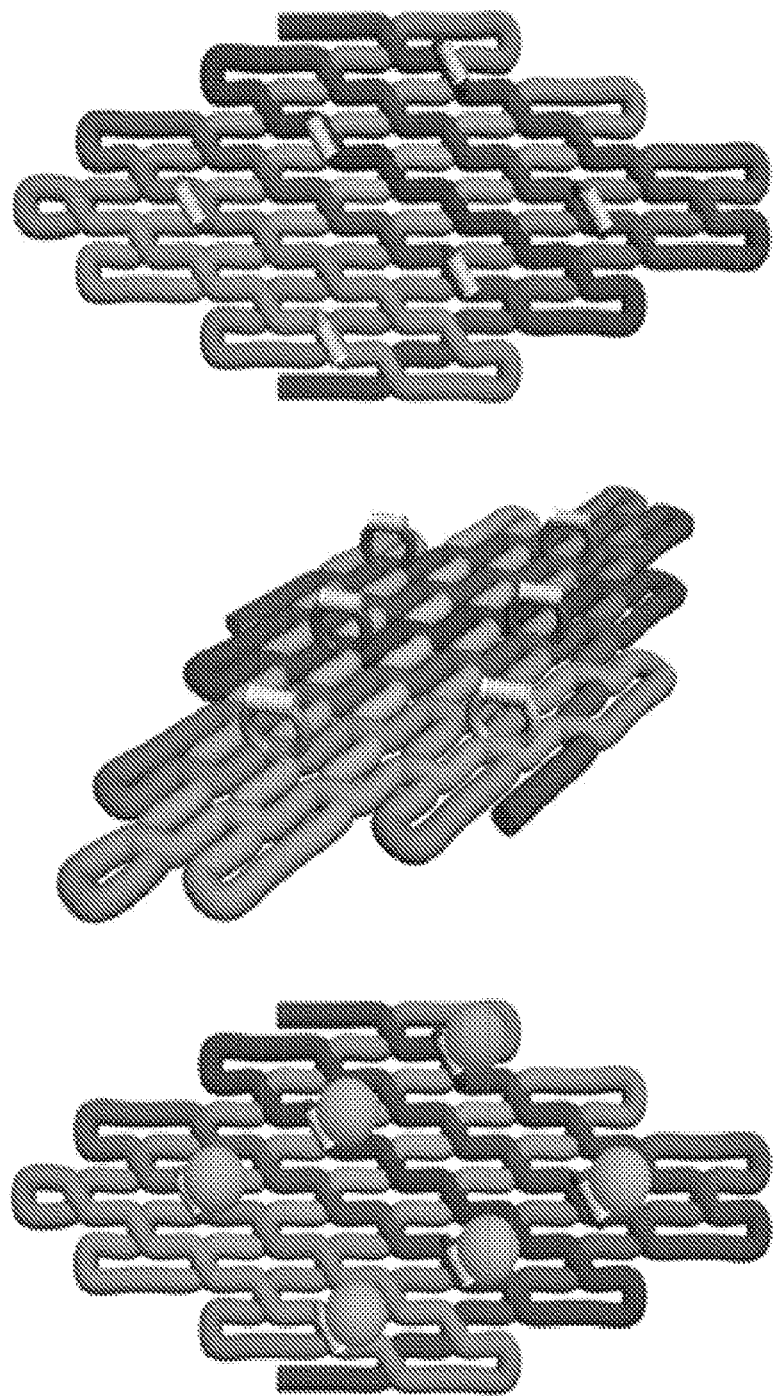
FIG. 5A shows schematics of ssDNA nanostructures directing the assembly of target molecules via single-stranded loops for target recognition and fixation.
Figure 5B:
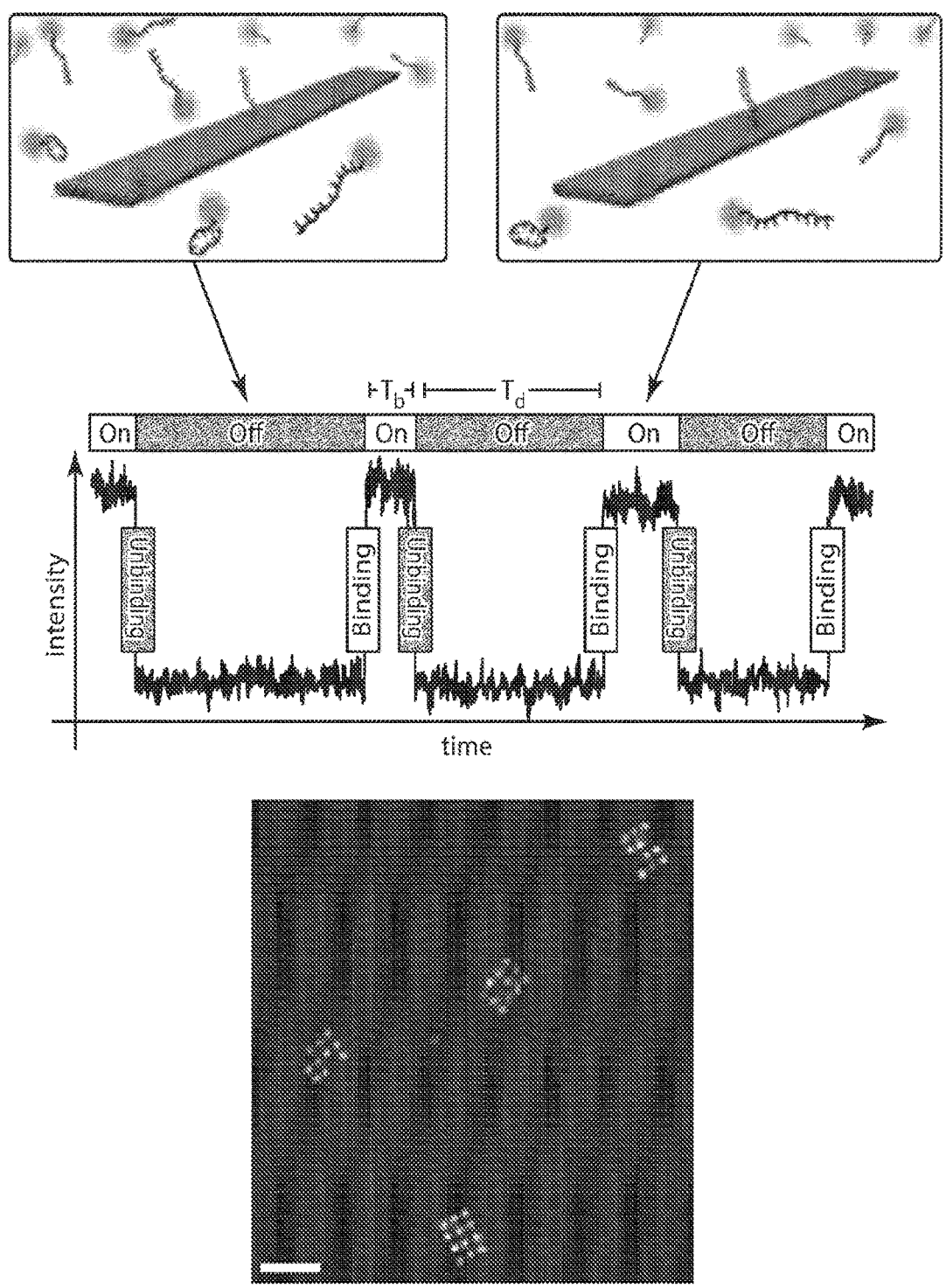
FIG. 5B is representative of a DNA-PAINT (point accumulation for imaging in nanoscale topography) technique (top panel) and data showing a 12-point rectangle nanostructure PAINT image. Scale bar: 100 nm.
Figure 6A:
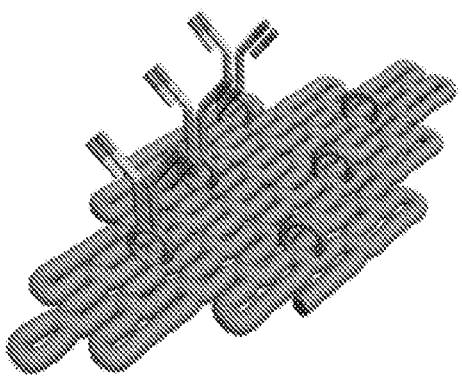
Figure 6B:
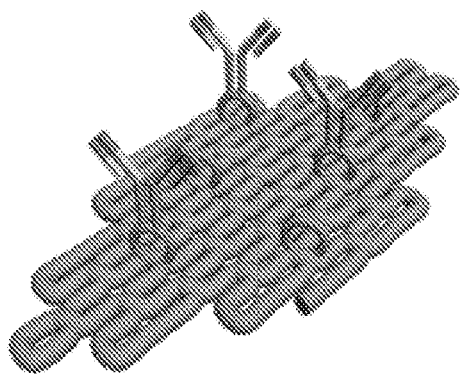
Figure 6C:
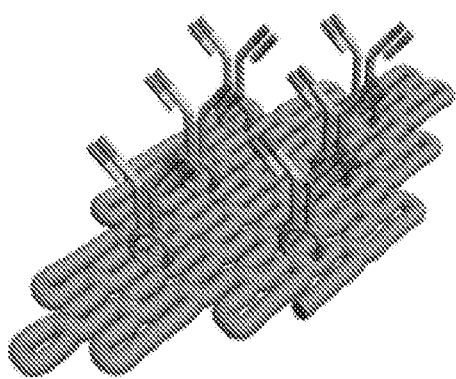
Figure 6D:
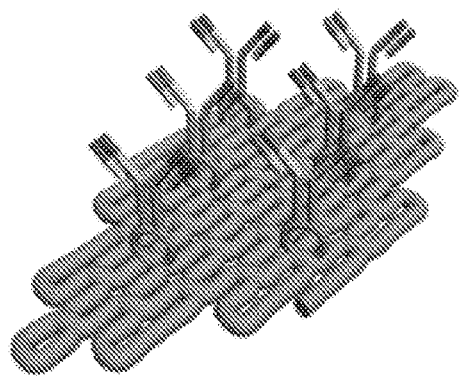

Example 3 ssDNA nanostructures are designed to contain single-stranded loops, for example, protruding from arbitrary positions on the structure. FIG. 5A illustrates an example of six-loop design based on a diamond-shape ssDNA nanostructure (top and middle panels) and attachment of heterogeneous elements, such as fluorescent dye molecules and protein structures (bottom panel). Based on this design, DNA-PAINT (points accumulation for imaging in nanoscale topography) is used to demonstrate the accurate arrangement capability of ssDNA nanostructures (FIG. 5B, top panel). FIG. 5B, bottom panel, shows reversible specific binding of fluorescently labeled nucleic acid being used to perform optical imaging with ~5 nm resolution on a nucleic acid nanostructures assembled from multiple strands of DNA. Note that one or more labeled points are missing, indicative of missing strands and local defects in such heterogeneous structures.

Example 4

Replicable ssDNA Origami
Protocol
Materials. All GBLOCK® strands were purchased from Integrated DNA Technologies Inc. at a 200 ng synthesis scale. All primer strands (with/without chemical modification) were purchased from Integrated DNA Technologies Inc. at a 100 nmole synthesis scale with HPLC purification. PHUSION® High-Fidelity PCR Master Mix with HF Buffer (100 rxns/50 µl vol) and Lambda Exonuclease (1,000 units) was purchased from NEW ENGLAND BIO LABS INC.

Synthesis of single-stranded DNA (ssDNA). All ssDNA were synthesized by multi-template polymerase chain reaction followed by Lambda Exonuclease treatment. A typical PCR reaction solution contains 25 µL 2× PHUSION® High-Fidelity PCR Master Mix with HF Buffer, 23 µL 8% DMSO, 0.5 µL GBLOCK® DNA (4 mg/L) for both temples, 0.5 phosphorothioate primer (forward, 100 uM) and 0.5 µL phosphate primer (reverse, 100 uM). Melting temperature of primer strands were designed to be 72° C. to minimize the impact of the secondary structure of the DNA product. An example of a PCR reaction is:

TABLE 1

| STEP | TEMP | TIME |
| --- | --- | --- |
| Initial Denaturation | 98° C. | 30 seconds |
| 25-35 Cycles | 98° C. | 10 seconds [strand separation stage] |
|  | 72° C. | 4 minutes [annealing stage & polymerase extension stage] |
| Final Extension | 72° C. | 10 minutes |
| Hold | 4° C. |  |

PCR products (double-stranded DNA or dsDNA) were treated with Lambda Exonuclease with/without column purification. Typically, 10 µL PCR dsDNA, 5 µl 10× Lambda Exonuclease buffer and 5 uL Lambda Exonuclease were added to 30 µL of $H_2O$ for reaction. The mixture was Incubated for 18 hours at 37° C., and then boiled at 98° C. for 5 minutes to inactivate the enzyme before use. The product (ssDNA) was then directly add to folding reaction without purification.

Assembly of ssDNA Nanostructures.

ssDNA product was added to TAE Mg$^{2+}$ buffer (40 mM Tris, 20 mM Acetic acid, 2 mM EDTA and 12.5 mM Magnesium acetate, pH 8.0). The resulting solutions were annealed from 85° C. to 25° C. to form the designed structures. The exact temperature steps for the slow anneal are as follows: 85 to 60° C. at 1° C. per 10 minutes; 60 to 40° C. at 1° C. per 30 minutes; 40 to 25° C. at 1° C. per 15 minutes. All samples were then subjected to AFM imaging without further purification.

Example 5

Synthesis of Single-Stranded DNA

Another challenge for constructing ssDNA nanostructures stems from the difficulty of synthesizing the ssDNA nanostructures. As self-complementarity is an intrinsic property of ssDNA nanostructures, its strong secondary structure may present challenges to synthesize the DNA. As a result, minimization of local self-interaction is a key part of ssDNA nanostructure design. In order to decrease self-complementarity, the length of most helical domains was limited to 10 bp. Then, the ssDNA strand is further split into two approximately equal halves to separate all helical domain sections, which decreases the self-interaction substantially (FIG. 9A). A 30 bp overlap is added to the ends of two half strands so that they can be joined and amplified at the same time through a one-step PCR reaction (FIG. 9B). Two different primers are used in the PCR step, primer 1 with a 5' phosphorothioate modification and primer 2 with a 5' phosphorylation modification. Because the phosphorothioate modification on the forward strand renders the inter-nucleotide linkage resistant to nuclease degradation while phosphorylation makes the reverse strand a substrate for DNA exonuclease, only the reverse strand will be digested by lambda exonuclease, yielding the protected ssDNA strand (FIG. 9C). After a typical 2-hour annealing process, this ssDNA will fold into the target shape as shown in FIG. 4C.

Figure 34:
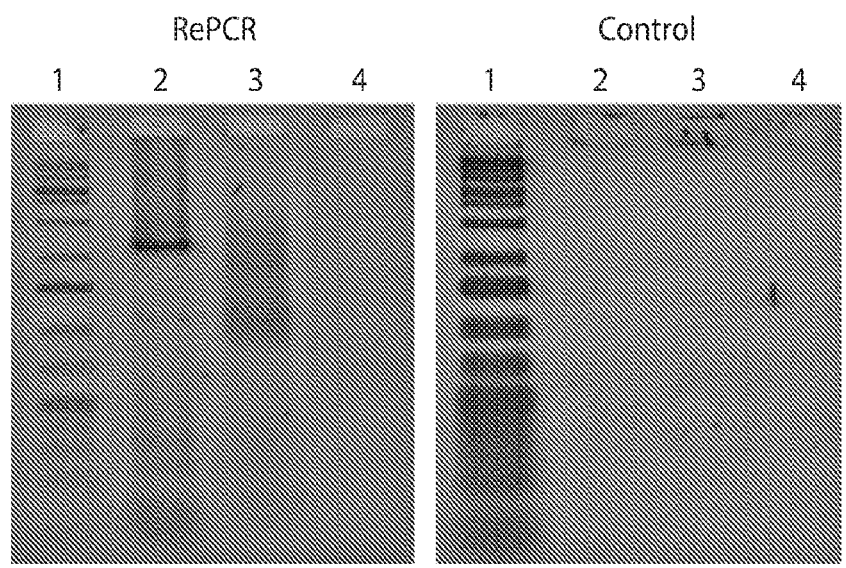
FIG. 34 shows agarose gel images of 5×5 diamond-shape ssDNA nanostructure rePCR products and a control experiment. Left: Standard rePCR Products. Lane 1: 1 Kb ladder; lane 2: PCR product; lane 3: exonuclease treated product; lane 4: annealed products. Right: rePCR control experiment with no PCR buffer added. Lane 1: 1 Kb ladder; lane 2: PCR product; lane 3: exonuclease treated product; lane 4: annealed product.

As one of the important features for ssDNA nanostructures, the replicability of the ssDNA nanostructure is tested as a single-stranded template for the next cycle of amplification and reaction. Instead of the two original double-stranded template strands, 0.5 µL of previously folded ssDNA nanostructure product (sample from FIG. 4C) was added to 50 µL PCR reaction mixture to produce the amplified dsDNA product. After repeating the synthesis processes under the same experimental conditions, the ssDNA template was successfully replicated and the annealed structures were imaged under AFM (FIG. 9E). In control experiments with no polymerase, the ssDNA nanostructure of the present disclosure was not replicated (FIG. 34).

Materials and Methods

Materials:

Double-stranded DNA (dsDNA) templates were purchased from Integrated DNA Technologies Inc. (IDTDNA.com) as GBLOCK® DNA at 200 ng synthesis scale. Primers including 5' phosphorothioate modification (T*T*T*T*T*T*) or 5' phosphorylation (/5Phos/) were purchased from Integrated DNA Technologies Inc. at 100 nmole synthesis scale with HPLC purification. PHUSION® High-Fidelity PCR Master Mix with HF Buffer (100 reactions/50 µL volume) and Lambda Exonuclease (1,000 units) was purchased from New England Biolabs, Inc. MinElute PCR Purification Kit was purchased from QIAGEN® (qiagen.com). Nicking endonuclease Nb.BbvCI (1,000 units), restriction endonucleases EcoRI (5,000 units), XhoI (5,000 units) and HindIII (5,000 units), PCR Cloning Kit (20 reactions), NEB 10-beta and NEB Stable competent E. coli were purchased from NEW ENGLAND BIO LABS INC. pGEM-7zf(−) vector, Pure yield plasmid miniprep system and the Wizard SV Gel and PCR Clean-UP System were purchased from Promega (promega.com).

DNA Sequence Design:

DNA structures and sequences were designed with the Tiamat software[40]. Sequence generation of ssDNA nanostructures uses the following criteria in the software: (1) Unique sequence limit: 8-10; (2) Repetition limit: 8; (3) G repletion limit: 4; (4) G/C percentage: 0.38-0.5.

Dynamic Relaxation Model:

The dynamic relaxation model is realized by the Autodesk 3ds Max software. Spline models of target structure are first created and treated as a fix-ended soft rope. Such rope is relaxed under simulated gravity at the chosen direction. Details about this model such as the animation parameters and the falling direction set up are described above.

In Vitro PCR Sample Preparation:

ssDNA was synthesized by multi-template polymerase chain reaction followed by Lambda Exonuclease treatment. A typical PCR reaction solution contained 25 µL 2× PHUSION® High-Fidelity PCR Master Mix with HF Buffer, 23 µL 8% DMSO, 0.5 µL GBLOCK® DNA (4 ng/µL) for both temples, 0.5 µL phosphorothioate primer (forward, 100 µM) and 0.5 µL phosphate primer (reverse, 100 µM). Primers were designed to have melting temperatures of 64° C. to minimize the impact of the secondary structure of the DNA template. A typical PCR reaction was: (1) Initial denaturation at 98° C. for 30 seconds; (2) 25-35 cycles of 10 seconds at 98° C. (strand separation stage), 30 seconds at 65° C. (annealing stage) and 1 minute at 72° C. (polymerase extension stage); (3) Final extension for 10 minutes at 72° C.; (4) Hold at 4° C. after reaction.

After PCR, 50 µL of PCR product was purified using the QIAGEN® MinElute PCR Purification Kit according to the manufacturer's instructions. 100 µL H$_2$O was used for elution of DNA after the spin columns purification. The purified DNA was then treated with Lambda Exonuclease. Typically, 5 µL 10× Lambda Exonuclease buffer and 5 µL Lambda Exonuclease (5,000 units/ml) were added to 40 µL dsDNA solution for reaction. The mixture was incubated for 12 hours at 37° C., and then boiled at 98° C. for 5 minutes to inactivate the enzyme before use. The product (ssDNA) was either directly added to a folding reaction, or gel-purified using Squeeze 'N Freeze columns (Bio-Rad) and then added to 1×TAE Mg$^{2+}$ buffer (40 mM Tris, 20 mM Acetic acid, 2 mM EDTA and 12.5 mM Magnesium acetate, pH 8.0) for folding. The resulting solution was annealed from 85° C. to 25° C. to form the designed structures. The steps for the slow annealing were as follows: 85° C. to 60° C. at 1° C. per 10 minutes; 60° C. to 40° C. at 1° C. per 30 minutes; 40° C. to 25° C. at 1° C. per 15 minutes. The steps for the fast annealing were as follows: 85° C. to 65° C. at 1° C. per 1 minute; 65° C. to 45° C. at 1° C. per 5 minutes; 45° C. to 25° C. at 1° C. per 1 minute. All samples were then subjected to AFM imaging without further purification.

AFM Imaging:

For AFM imaging, the sample (15 µL) was deposited onto a freshly cleaved mica surface (Ted Pella, Inc.) and left to adsorb for 1 minute. 40 µL 1×TAE-Mg$^{2+}$ and 15 µL 100 mM NiCl$_2$ was added onto the mica, and the sample was scanned on a Veeco 5 Multimode AFM in the Scanasyst in Fluid mode using scanasyst in fluid+ tips (Veeco, Inc.).

Yield Quantification with Native Agarose Gel Electrophoresis:

Yields of ssDNA nanostructures were estimated by analysis using native agarose gel electrophoresis. The ratio between the fluorescence intensity of the target band and that of the entire lane was used to represent the gross yield of structure formation while background intensity was subtracted from the measured intensity for correction.

REFERENCES

1. Winfree, E., Liu, F., Wenzler, L. A., & Seeman, N. C. Design and self-assembly of two-dimensional DNA crystals. Nature, 394(6693), 539-544 (1998).
2. Mao, C., Sun, W., & Seeman, N. C. Designed two-dimensional DNA Holliday junction arrays visualized by atomic force microscopy. Journal of the American Chemical Society, 121(23), 5437-5443 (1999).
3. Yan, H., Park, S. H., Finkelstein, G., Reif, J. H., & LaBean, T. H. DNA-templated self-assembly of protein arrays and highly conductive nanowires. Science, 301 (5641), 1882-1884 (2003).
4. Yan, H., LaBean, T. H., Feng, L., & Reif, J. H. Directed nucleation assembly of DNA tile complexes for barcode-patterned lattices. Proceedings of the National Academy of Sciences, 100(14), 8103-8108 (2003).
5. Rothemund, P. W., Papadakis, N., & Winfree, E. Algorithmic self-assembly of DNA Sierpinski triangles. PLoS biology, 2(12), e424 (2004).
6. Park, S. H., Yin, P., Liu, Y., Reif, J. H., LaBean, T. H., & Yan, H. Programmable DNA self-assemblies for nanoscale organization of ligands and proteins. Nano Letters, 5(4), 729-733 (2005).
7. Shih, W. M., Quispe, J. D., & Joyce, G. F. A 1.7-kilobase ssDNA that folds into a nanoscale octahedron. Nature, 427(6975), 618-621 (2004).
8. Ke, Y., Liu, Y., Zhang, J., & Yan, H. A study of DNA tube formation mechanisms using 4-, 8-, and 12-helix DNA nanostructures. Journal of the American Chemical Society, 128(13), 4414-4421 (2006).
9. Rothemund, P. W. Folding DNA to create nanoscale shapes and patterns. Nature, 440(7082), 297-302 (2006).
10. He, Y., Ye, T., Su, M., Zhang, C., Ribbe, A. E., Jiang, W., & Mao, C. Hierarchical self-assembly of DNA into symmetric supramolecular polyhedra. Nature, 452(7184), 198-201 (2008).
11. Yin, P., Hariadi, R. F., Sahu, S., Choi, H. M., Park, S. H., LaBean, T. H., & Reif, J. H. Programming DNA tube circumferences. Science, 321(5890), 824-826 (2008).
12. Sharma, J., Chhabra, R., Cheng, A., Brownell, J., Liu, Y., & Yan, H. Control of self-assembly of DNA tubules through integration of gold nanoparticles. Science, 323 (5910), 112-116 (2009).
13. Douglas, S. M., Dietz, H., Liedl, T., Hogberg, B., Graf, F., & Shih, W. M. Self-assembly of DNA into nanoscale three-dimensional shapes. Nature, 459(7245), 414-418 (2009).
14. Dietz, H., Douglas, S. M., & Shih, W. M. Folding DNA into twisted and curved nanoscale shapes. Science, 325 (5941), 725-730 (2009).
15. Zheng, J., Birktoft, J. J., Chen, Y., Wang, T., Sha, R., Constantinou, P. E., . . . & Seeman, N. C. From molecular to macroscopic via the rational design of a self-assembled 3D DNA crystal. Nature, 461(7260), 74-77 (2009).
16. Andersen, E. S., Dong, M., Nielsen, M. M., Jahn, K., Subramani, R., Mamdouh, W., . . . & Kjems, J. Self-assembly of a nanoscale DNA box with a controllable lid. Nature, 459(7243), 73-76 (2009).
17. Han, D., Pal, S., Liu, Y., & Yan, H. Folding and cutting DNA into reconfigurable topological nanostructures. Nature nanotechnology, 5(10), 712-717 (2010).
18. Han, D., Pal, S., Nangreave, J., Deng, Z., Liu, Y., & Yan, H. DNA origami with complex curvatures in three-dimensional space. Science, 332(6027), 342-346 (2011).
19. Yang, Y., Han, D., Nangreave, J., Liu, Y., & Yan, H. DNA origami with double-stranded DNA as a unified scaffold. ACS nano, 6(9), 8209-8215 (2012).
20. Wei, B., Dai, M., & Yin, P. Complex shapes self-assembled from ssDNA tiles. Nature, 485(7400), 623-626 (2012).
21. Ke, Y., Ong, L. L., Shih, W. M., & Yin, P. Three-dimensional structures self-assembled from DNA bricks. Science, 338(6111), 1177-1183 (2012).
22. Han, D., Pal, S., Yang, Y., Jiang, S., Nangreave, J., Liu, Y., & Yan, H. DNA gridiron nanostructures based on four-arm junctions. Science, 339(6126), 1412-1415 (2013).
23. Ke, Y., Ong, L. L., Sun, W., Song, J., Dong, M., Shih, W. M., & Yin, P. DNA brick crystals with prescribed depths. Nature chemistry. 6, 994-1002 (2014).
24. Marchi, A. N., Saaem, I., Vogen, B. N., Brown, S., & LaBean, T. H. Toward Larger DNA Origami. Nano letters, 14(10), 5740-5747 (2014).
25. Iinuma, R., Ke, Y., Jungmann, R., Schlichthaerle, T., Woehrstein, J. B., & Yin, P. Polyhedra self-assembled from DNA tripods and characterized with 3D DNA-PAINT. science, 344(6179), 65-69 (2014).
26. Chen, J., & Seeman, N. C. Synthesis from DNA of a molecule with the connectivity of a cube. Nature, 350 (6319), 631-633 (1991).
27. Seeman, N. C. The design and engineering of nucleic acid nanoscale assemblies. Current Opinion in Structural Biology, 6(4), 519-526 (1996).
28. Han, D., Jiang, S., Samanta, A., Liu, Y., & Yan, H. Unidirectional Scaffold-Strand Arrangement in DNA Origami. Angewandte Chemie International Edition, 52(34), 9031-9034 (2013).
29. Alexander, J. W., & Briggs, G. B. On types of knotted curves. Annals of Mathematics, 562-586 (1926).
30. Alexander, J. W. Topological invariants of knots and links. Transactions of the American Mathematical Society, 30(2), 275-306 (1928).
31. Murasugi, K. Knot theory and its applications. Springer Science & Business Media (2007).
32. Mansfield, M. L. Are there knots in proteins?. Nature Structural & Molecular Biology, 1(4), 213-214 (1994).
33. Takusagawa, F., & Kamitori, S. A real knot in protein. Journal of the American Chemical Society, 118(37), 8945-8946 (1996).
34. Taylor, W. R. A deeply knotted protein structure and how it might fold. Nature, 406(6798), 916-919 (2000).
35. Wagner, J. R., Brunzelle, J. S., Forest, K. T., & Vierstra, R. D. A light-sensing knot revealed by the structure of the chromophore-binding domain of phytochrome. Nature, 438(7066), 325-331 (2005).
36. Lin, C., Rinker, S., Wang, X., Liu, Y., Seeman, N. C., & Yan, H. In vivo cloning of artificial DNA nanostructures. Proceedings of the National Academy of Sciences, 105 (46), 17626-17631 (2008).
37. Lee, H., Popodi, E., Tang, H., & Foster, P. L. Rate and molecular spectrum of spontaneous mutations in the bacterium *Escherichia coli* as determined by whole-genome sequencing. Proceedings of the National Academy of Sciences, 109(41), E2774-E2783 (2012).
38. Geary, C., Rothemund, P. W., & Andersen, E. S. A single-stranded architecture for cotranscriptional folding of RNA nanostructures. Science, 345(6198), 799-804 (2014).

39. Horiya, S., Li, X., Kawai, G., Saito, R., Katoh, A., Kobayashi, K., & Harada, K. RNA LEGO: magnesium-dependent formation of specific RNA assemblies through kissing interactions. Chemistry & biology, 10(7), 645-654 (2003).
40. Williams, S., Lund, K., Lin, C., Wonka, P., Lindsay, S., & Yan, H. Tiamat: a three-dimensional editing tool for complex DNA structures. In DNA Computing (pp. 90-101). Springer Berlin Heidelberg (2009).
41. Lickorish, W. R. (2012). An introduction to knot theory (Vol. 175). Springer Science & Business Media.
42. Biou, V., Dumas, R., Cohen-Addad, C., Douce, R., Job, D., & Pebay-Peyroula, E. (1997). The crystal structure of plant acetohydroxy acid isomeroreductase complexed with NADPH, two magnesium ions and a herbicidal transition state analog determined at 1.65 Å resolution. The EMBO journal, 16(12), 3405-3415.

Sequences

Figure 35:
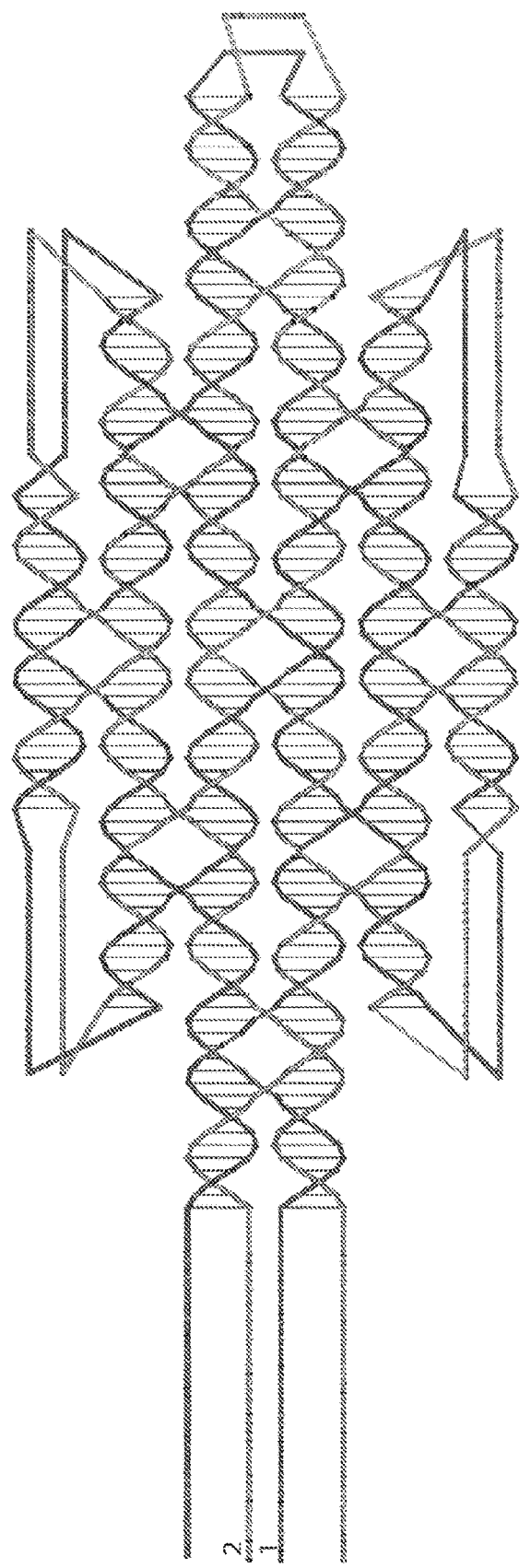
FIG. 35 shows the design detail of a 3×3 diamond-shape ssDNA nanostructure. The black strand is the forward strand and gray strand is the reverse strand.

```
3 x 3 Diamond-shape ssDNA (FIG. 35)
Forward strand:
TACGGCACGTAAGCCTTGCATTGACTAGCCCGGTACGTATTTCTTACGCAGCCATGTCTGGCCTCGGACCTCAGAG
GGAATGCGTCACTTTTCTTTCTTTCTTTCTTTTCGAGGCGTCCAATGATTGCTGTTTAGCAAAGTGGCGCACGTTG
TCGGCACCCTACGCTTTTTCTTTCTTTCTTTCTTTTCCGTCTACTTCCGGTAAGGGAGACTTCCAAGTGCGTGGGT
TTGCGAGTGGCGGACGCTTTCTTTGGTACGCCCGACTCGCACGAGATTTGCAACGCCAATTATAGCCCCTCTCCAG
CTCTGCTTTTCTTTCTTTCTTTCTTTTGTTGTCAAGTTTGAGTAAGCTGGCAAACTTTGATGGCGGACGGGCAAAT
CCGACCGAGTTTTCTTTCTTTCTTTCTTTTCGAATAAAGATACCGGTCCGGGATTCTCGAGAGTCCTCATGCTAAG
AATGGCGGAAGCACAGCGACTAGATAATCGACCGCGTCCCAT (SEQ ID NO: 1)

Reverse strand:
ACAGCGACTAGATAATCGACCGCGTCCCATGCTTCCGCCACAGCTGGCATGAGGACGCCGACGAATCCCGGAGTTG
AATCTTTATTCGTTTTCTTTCTTTCTTTCTTTTCTCGGTCGGAACTTGGCGTCCGCCATAGTCGTTTGCCAGCTTG
CCAGAACTTGACAACTTTTCTTTCTTTCTTTCTTTTGCAGAGCTGGTGGAGTGCTATAATTGATCATTCAAATCTC
GTTGGTTCCGGGCGTACCTTCTTTAGCGTCCGCCGAACCAAAACCCACGCTTTGCCAAGTCTCCCTTTCAACAAGT
AGACGGTTTTCTTTCTTTCTTTCTTTTAGCGTAGGGTTCTCGAAACGTGCGCCACGACTCTAAACAGCAGCGTTGG
GACGCCTCGTTTTCTTTCTTTCTTTCTTTTGTGACGCATTACTCCAGAGGTCCGAGACTCAACATGGCTGCGCAGC
TGATACGTACCGATCCGGCATCGCGATTCATCTTCGCGAATC (SEQ ID NO: 2)

Figure 36:
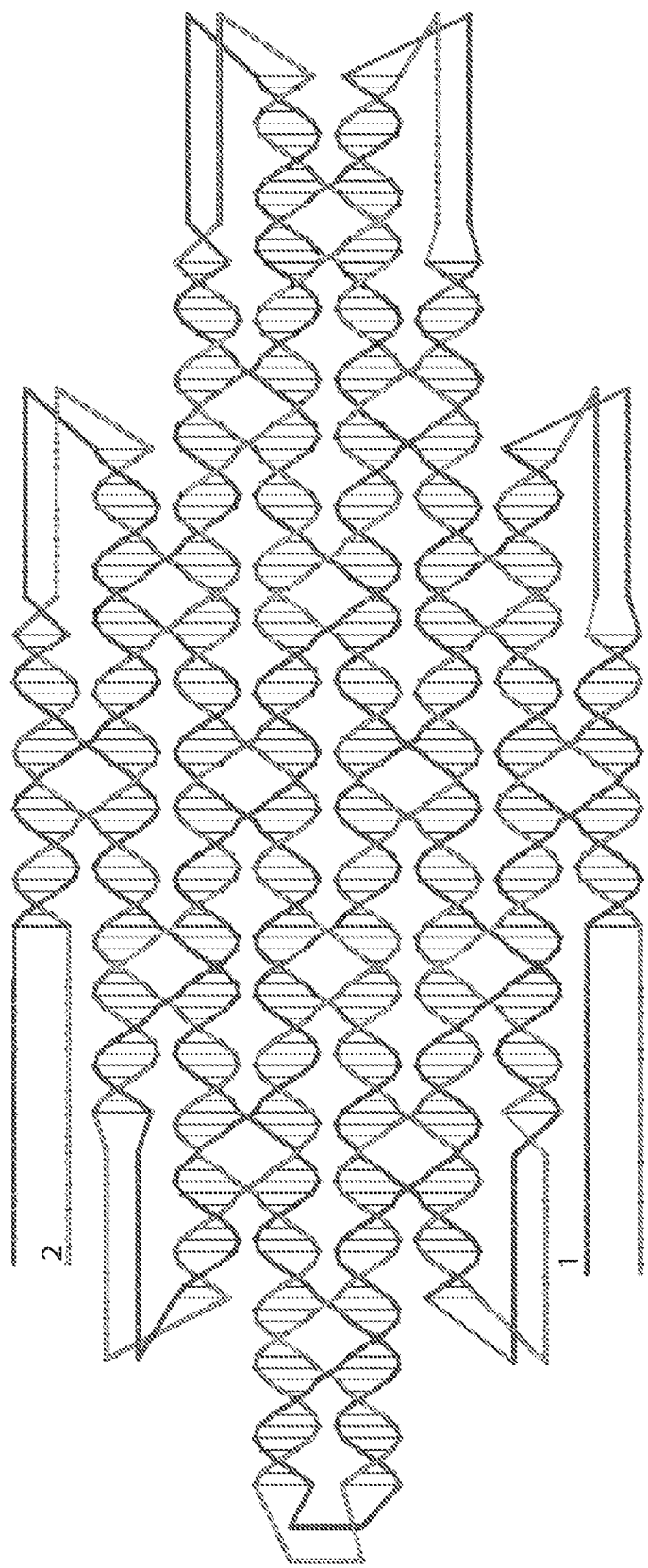
FIG. 36 shows the design detail of a 4×4 diamond-shape ssDNA nanostructure. The black strand is the forward strand and gray strand is the reverse strand.

4 x 4 Diamond-shape ssDNA (FIG. 36)
Forward strand:
TACGGCACGTAAGCCTTGCATTGACTAGCCGTCGATCAGTGGTTATGGGTGGCTGCCCGCGGGAAGGGATGGTAAA
CACGAGCATAACACAGCGGGTCGCTGTATTTTCTTTCTTTCTTTCTTTTGTTTCTACAGGCTGAGAGCGTCCGCCG
AACCAAAACCCACGCTTTGCCAAGTCTCCCTTTCAACAAGTAGACGGTTTTCTTTCTTTCTTTCTTTTAGCGTAGG
GTTCTCGAAACGTGCGCCACGACTCTAAACAGCAGCGTTGGGACGCCTCGATATCTCCCTGCATACTTTTCTTTCT
TTCTTTCTTTTTGGTGGGTAGTTCATCGTGACGCATTACTCCAGAGGTCCGAGACTCAACATGGCTGCGCAGCTGA
TACGTACCGTTCTTTGCTTCCGCCACAGCTGGCATGAGGACGCCGACGAATCCCGGAGTTGAATCTTTATTCGGGC
CACGGAAGGGTGGTTTTCTTTCTTTCTTTCTTTTGAACCGCCTCCCGCGGCTCGGTCGGAACTTGGCGTCCGCCAT
AGTCGTTTGCCAGCTTGCCAGAACTTGACAACTTTTCTTTCTTTCTTTCTTTTGCAGAGCTGGTGGAGTGCTATAA
TTGATCATTCAAATCTCGTTGGTTCCGGGCGTACCCGGCCTGGTGTATGTGTTTTCTTTCTTTCTTTCTTTTTGAG
CACATTCGCTGTAATCTCATCGCCGCAATGGCTATGGGAGATATGCATAAGTTGCCCTAAATATAGCATTACAGCG
ACTAGATAATCGACCGCGTCCCAT (SEQ ID NO: 3)

Reverse strand:
ACAGCGACTAGATAATCGACCGCGTCCCATAATGCTATATGATGAACAACTTATGCGTGGGTCCCATAGCCACTCA
GCCGATGAGATTTAGGATAATGTGCTCATTTTCTTTCTTTCTTTCTTTTCACATACACCTGTTTAGGTACGCCCGA
CTCGCACGAGATTTGCAACGCCAATTATAGCCCCTCTCCAGCTCTGCTTTTCTTTCTTTCTTTCTTTTGTTGTCAA
GTTTGAGTAAGCTGGCAAACTTTGATGGCGGACGGGCAAATCCGACCGAGGGCTCGGAGGCGGTTCTTTTCTTTCT
TTCTTTCTTTTCCACCCTTCCATAACCCGAATAAAGATACCGGTCCGGGATTCTCGAGAGTCCTCATGCTAAGAAT
GGCGGAAGCTTCTTTCGGTACGTATTTCTTACGCAGCCATGTCTGGCCTCGGACCTCAGAGGGAATGCGTCACTTA
GGGCTACCCACCATTTTCTTTCTTTCTTTCTTTTGTATGCAGGGACCCACCGAGGCGTCCAATGATTGCTGTTTAG
CAAAGTGGCGCACGTTGTCGGCACCCTACGCTTTTTCTTTCTTTCTTTCTTTTCCGTCTACTTCCGGTAAGGGAGA
CTTCCAAGTGCGTGGGTTTGCGAGTGGCGGACGCTTTCGGCGTGTAGAAACTTTTCTTTCTTTCTTTCTTTTTACA
GCGACCATCCTAGTTATGCTCGAGGCCGCCATCCCTTCCGAGCCGCAGCCACCCGTGGCCACTGATCGACATCCGG
CATCGCGATTCATCTTCGCGAATC (SEQ ID NO: 4)

Figure 37:
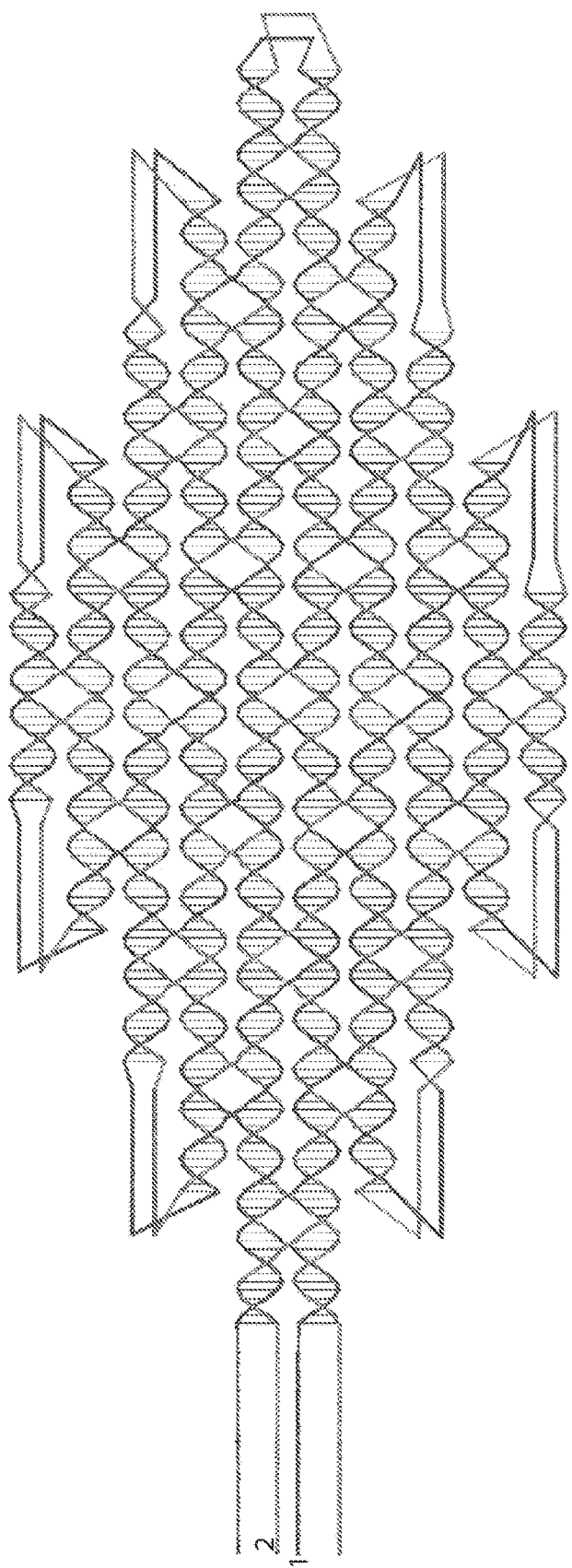
FIG. 37 shows the design detail of a 5×5 diamond-shape ssDNA nanostructure. The black strand is the forward strand and gray strand is the reverse strand.

5 x 5 Diamond-shape ssDNA (FIG. 37)
Forward strand:
TACGGCACGTAAGCCTTGCATTGACTAGCCCTCCCCACAACTGACTGATTGCTGAATCTTGCGGTGTGTGGAGTT
CATCTGCATCCTGCCCAACTCCGGCGGCGGTTGCACGATCAACATTTTCTTTCTTTCTTTCTTTTATGAAAGGCAG
TTGGGCCAGTAGGCGGTCCACCTATGAGCACCAAAGGATCCTGGTCGTCGGGCCAGCCACCACGTATTGCTATTAC
GATTTTTCTTTCTTTCTTTCTTTTACGTATGCTAACTCATTGCTCCTAAGACCAGTATAAGTTCCATGGCTGGACT
CCGGCAATGAGCGGGAACCGCTGATTCAACGACCAGCATTTTCTTTCTTTCTTTCTTTTACCATTCCGCGTCGAGG
GACGAATTGGATCTATCTCTGTGTCATTCTGGACCGTAAGCGCGCGTCAGAATTTGAAGAGGACAATCGACGTTTT
TCTTTCTTTCTTTCTTTTCGCTCTTCAAACGAGTCGGTTGCAATGTTGCGCCTCGGCGTGATCCTGCTTACTCGAC
TGCTCTAATGGACAAGGCTTAACCGCGCTTTCTTCTTTATCTCTCTTGTTAAGCAGTCTGCGAAATCGGGTAGAA
CCAATGAATCCTCAAGCACTGCCCGGGTAGAGATGAGCAACCTTCTTGTCCTTTTTCTTTCTTTCTTTCTTTTTCT
GAAGCAGACTATCTGACGCAGGGGTGGACGAAACCGAGGTGCCGAAGACAAGGGCTAGATCGGATTTCTCCGGTCC
GGATCACGCGTTTTTCTTTCTTTCTTTCTTTTGGACAATCAGCAGGATTAAGTTCAACCTTGAATCGACTCCGGCA
GCCACAGATCTCTACAGGACGAACGACACCTGAACTACGCTACCTCTTTTCTTTCTTTCTTTCTTTTGAAAGTGCT
TATCTAGACGAAACATAGCCCGAGCCGAAGCGTATGTCGCGTGCCCGAACGCGCCGTACAACCACAGGTTTTGGA
AAATCTTTTCTTTCTTTCTTTCTTTTCCTTTCCTCAACTCGTGTACGGGTCTAAACCATCAGGACAGTATGAGTAC
AGGAAGGGCTCGAAGGCATGTTCAGTCAGTAGCCCCCGCAACAGCGACTAGATAATCGACCGCGTCCCAT
(SEQ ID NO: 5)
```

-continued

Reverse strand:
ACAGCGACTAGATAATCGACCGCGTCCCATTGCGGGGGCTAGTCTTTGAACATGCCCAATACCCCTTCCTGTGGGT
GTACTGTCCTGATCCTCTAGACCCGTACCGTGGGTGAGGAAAGGTTTTCTTTCTTTCTTTTGATTTTCCAAC
GCAACTGGTTGTACGAAGTGCTCGGGGCACGACTGGTACGCTTCGGCGGTCTTTATGTTTCGTCAAGATAAGCACT
TTCTTTTCTTTCTTTCTTTCTTTGAGGTAGCGTTTTCCTGGTGTCGTTCCCTTTGTAGAGATCTGGCCAGACCGG
AGTCGACAGAATGTTGAACTTACGCATTCTGATTGTCCTTTTCTTTCTTTCTTTCTTTTACGCGTGATCAGAGCAG
GAGAAATCCAATTCTGCCCTTGTCTGCTCATCCTCGGTTTCAGAATCCCCTGCGTCATTGGGCCTGCTTCAGATTT
TCTTTCTTTCTTTCTTTTAGGACAAGAAACGGCTTCATCTCTACCCCAACAGTGCTTGAGCGGTAGTTGGTTCTAC
CTCGACTTCGCAGACTCACGCTCAAGAGAGATTTCTTTGAAAGCGCGGAGCGTGCTTGTCCATTCGGACCGTCGAG
TAAGAATGCGCACGCCGAGGAACCTGATTGCAACCGCCCACGTTGAAGAGCGTTTTCTTTCTTTCTTTCTTTTACG
TCGATTGTGGTTTTCAAATTCTGGCACTTGCTTACGGTCTTCAAGGACACAGAGAAGAATTCAATTCGTCCCCCGA
TGCGGAATGGTTTTTCTTTCTTTCTTTTTGCTGGTCGTCTACCGAGCGGTTCCCTCGGCATGCCGGAGTCTC
TGGCTGGAACTTATCGACATCTTAGGAGCAACACCCTAGCATACGTTTTTCTTTCTTTCTTTCTTTTATCGTAATA
GTTCGAGGTGGTGGCTGAAGACCCGACCAGGATGTCCTGGTGCTCATAGGATTCTCGCCTACTGGCCGGGCTGCCT
TTCATTTTTCTTTCTTTCTTTTTGTTGATCGTAGCCGTGCCGCCGGAGGATAGTAGGATGCAGAAGGAAACC
ACACACCGCTAGATTCAGCAATCAAAGACTTGTGGGGAGATCCGGCATCGCGATTCATCTTCGCGAATC
(SEQ ID NO: 6)

Figure 38:
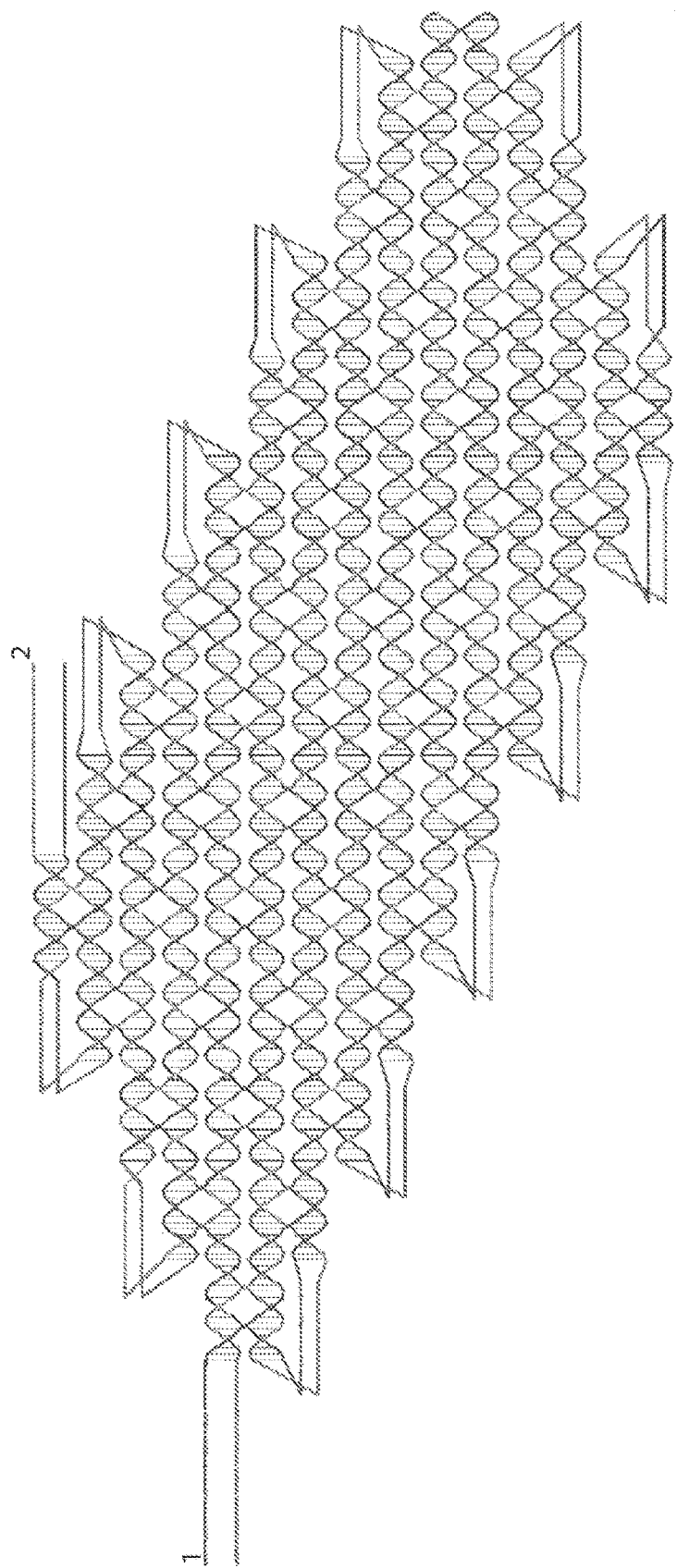
FIG. 38 shows the design detail of a rhomboid-shape ssDNA nanostructure. The black strand is the forward strand and gray strand is the reverse strand.

Rhomboid-shape ssDNA (FIG. 38)
Forward strand:
TACGGCACGTAAGCCTTGCATTGACTAGCCCTTTCGATCGTGTTAGCTTTTATATCCCCACCACTAGCAAACGCGC
GCCGTGCGGACTACAGAAGCTGAGTACGAGACCTTGTATCCTGCTGGTCTTGCAGGAGGACTCGTGTCATAGCCGC
TTTTTTTTGGCCGTGACTCATAACTTGTAAGAAGAGACTGTGGTACAGTGTTACCTACGTATGCTGAGTGGCTAGT
TCACGCCACCTCGGGTACATGCGCCCCGCCGAGATGTAGACATCTGCGTCACCGTCGGCGTTAGCACATTCTACCA
TTTCACTCACAGGCGCCTCTCCCGGGTCCTGTTTCGTCAAGGATTCAGGGCCCCTTCCTCGTACGAGAGCGACCC
GCCCAACCGTGGCGCGCACGGCGAAGAAGCGGCGGCCCCTAGTCGTCATTGCAAACTCTAGCTCGGGTTCTATTAT
TTCGTCATCAGTAGTCTAGTGACGAGTGGTTTGCGGCGGTTCTCGACTTGAAAGTTAAGATTCCAACAGCTATTGA
CGGTGTACACTCTGGGCTGCTCGGCTCCCCGCGAGAGGAAACTCGTTTTGTCCAACGGGCTGATCGCTCGGATGCA
AGACCGGGTACCACTTCTGAGTGTGTTTTAGAGGTCCACGGCCGGCGCGCCGGACATAACGGCAGTACAGGCACTA
GCGCAGATGAGGCCCTGCTCTACCTTGGCACGCTTTCGTGGGCCGTGTTAAACGGGAAATGGCCTGCGCAGGTC
CCTGTCCACTATAGCACTCCTACTTACACTTAATTTTACGAGATGGCAAGAACAGATGCCAAGGCTTAGAGTGGCC
CGCCCAAGGGCTCTCGTACTAGGGAGCGGGGAGCAGACCCACTCGCCGCTGCTGCTCAACTCAGTGCGTAGGA
TCTAGACCATTGTCCTTTGGGGTCTACCAGGGGCAGCCAGAGCGGCGAATAGACCGTTGATACGCTTCTTTGGGAC
AGTATCCTCTTGAGAAGTACAGGCGCAATAGGTCGAGTGGAACCGAGGTCTACAAATCTAATGGAGAACTTCTGCG
CATCCGGAGAGTGCTAATTGTAGACACCTGATGTAATAGGAGGGTTCGTACATCAGCGGCTCTCGACTTCATACAG
CCCAACACTGGGAATCAGTTTTCGGAAGGTGGTGAAATAACCAAGCGGCCACCCACTGGCCCCTAACCCAAGTCAC
GGGAGATGCTATTGCAAGTGTAGATGTTCTACCCAGACCAGGAGCGAGATGGACTAAAAGGCGGTGTTGTACTTGA
CAATTTGAGCAAAGCACAAGTTGCTGCTAGAGTACGAGCGACGCTTGCGCGCTGGACACGACGAAACCAAGCACG
CACTACGACTTCGCCAACCGCAGCAGTAGAGGCTGGCGTACGTCCTACACTCGCCTGAGAGCCAATCATGTACTCA
TGGTAGTCACATCACACTATTCTGAGCAGTGGCCGTTTGTGACAGGTGATCGGCACCCCTGGTACAATGCCAGTCA
CCGCCTGGACTTGGCATCGACACCGGGTTTCACGGTTGCCGTATAATACTAACGCTCGTTCAGGAGAATCAAGAGT
AGTCTCCTCGGTCATCAGGAGGGCTTGCTCTCCATGCAGGTAGCAACGCTGGCAACAGGTCCCGAAGTAATAGCCT
TTGGTCTCAAGCAGGCCAGGAAAGATATCTTGCAGCAGCTAGCACGCTTGGTCCTCGGGAAGTGAGTGTATGAGTA
AGTACCCGCACAAAGCTCGCGACTAGTGTAATCTCTTCCCGATCAGGGACCCGGGATAGGAACGTCTAAGTGCACC
CGGACTCAGTGCGTGAGGACGCGTGGGCATCCGTACGTTTCTCGCTAGGGCTTTCCCGCTCAATTAACACCCTGCCG
TTTCGGGGATAATTGGTCTATCGGCGTAAGTGCCTCCGGCAGCGACCCTGTATGCAAGGGTACATTGAGCACAGCG
ACTAGATAATCGACCGCGTCCCAT (SEQ ID NO: 7)

Reverse strand:
ACAGCGACTAGATAATCGACCGCGTCCCATTCTACTAGATGCGGCGAAACACGTTCAATTACTATAGAAACGGCAG
GTCCAGCATTGAGCGGGTTCTTCTAGCGAGAAATAACACGATGCCCACGCACGATCACGCAGAAGCTCCGTTGGGC
CGCTGACGTTCCCCACTTGGGTCCCTGACCTGAAAGAGATTACAGTAACGGCGAGCTTTGAAGCGTTACTTACTCA
AAGGGCCACTTCGTGATTAGCATGACATTGATCTGCTGCCCATCTTCTTTCCTGGCAACAGTGAGACCAAATAGAG
TTACTTCGGGATTCACCGCCAGCGTTGGCGTTTGCATGGTGCGCTAACCGCCTGCTATGACGAGGACCCGACTCTT
GATTCTGGCGCCCGAGCGTTAGTGTGAGACGGCAACCGCGCTAGCCGGTGTCGATAGCTTGTCCAGCACAAATCC
TTCTTGGCGCAGGGGTGCGGGCCACCTGTCACAGGAACTCACTGCTCAGGACATACGTGATGTGACAATAGTGAGTA
CATGACTCGTACTCAGGTCAGTACGCCTCCGAAGGTTGCCTCTACGAGAACGGTTGGCGAACGCCGAGTGCGTGCT
AGCAGCTCGTCGTGTCCGCCGGGCAAGCGTCGCCCGCGCTCTAGAACTGTGGGACCCAAGGAACAAATTGTGCTCC
CCAACACCGCCCGCGGTTCCATCTCGCAGTCGATCTGGGTAGACTGGGGACACTTGCAAAGTCCTCTCCCGCCACA
GCCCAGGACCCATCCTGGGTGGGTCTGGGGTTATTTCAGCGGGGTCCGAAAACTGCTGGCCAGTGTTGGGAGTGGT
GAAGTCGAGAGCCCCTGATGTACGAACTACAGGCCATCCGTATGTGTCTTGAGTTAGCACTCTCCGCAGGAGCAGA
AGTTCACCGTCAGATTTGTAGCATTGTGTTCCACTCGAGTCACTGCGCCCGTCAGTGGTCGGTGCTTATTGTCCCA
GCGACCCGTATCAACGAGCCACTCGCCGCTCTGGCCTACCCTGGTAGACCCGTTAGGACAATGGAGAACTTCCTAC
GCACACAATTGCAGACGCACAGGGGCGAGTGGGTCTCAAGTACGCTCCCTAGCGCGGGAGCCCTTGGGCCGATCAC
TCTAAGCCAAGCTATCTGTTCTTGAAGATACGTAAAATTAGCCCTTAGTAGGAGTGTCCCCGTGGACACGAATCTC
GAGGTACCTAGGGCCCGTTGCTGGAGGCCCCACGATGCGGGCCAAGGTAGCTGTTGGCCTCATCTGTGAAACTGC
CTGTACTAGTTCCATGTCCGGCGCAGCGCCCGTGGACCTACCGCGCACACTCAGACTGTATACCCGGTCTTTCCTG
CGAGCGATCAGCCCAAGGACAATGCGTTACGATATGGGAAACAAGCCGATAGGCCCAGAGTGTACTCCATTAATA
GCTGTTGCCAGCTTAACTTTCATCCTGGGAACCGCCGCGCTGCTCTCGTCACTAAATAGTTGATGACGAACTCACA
GAACCCGAGCGGCTATTTGCAATGACCGTTACGGGCCGCCGCGACTTCAGGTCCTCTAGGTCCGCTGCTTATGC
GCTCTGTGTTAAGGAAGGGGCTCGGGATCCTTGACGAGGTGAAACCCGGAGACCTGAATGTGAGTGAAACTATTG
AATGTGCTAAGTCGTACGGTGACGCCCCCAGCTACATCTCGCCACCTCGCATGTACCACAATGGGCGTGAACTGTC
TATTCAGCAGGACGAGGACTGCCAGAGAACCAGTCTGGTCGCACAAGTTATGACCTATGGCAAAAAACCAGACCT
ATGACACGTAGCATCCTGCAAGACTTCTCGGATACAAGGTTTGGCTCTCAGCTTCTGTCGGGCGCACGGCGCCTAC
CTGCTAGTGGTGAAGTGGTAAAAGCTAACGTCCTCGAAAGATCCGGCATCGCGATTCATCTTCGCGAATC
(SEQ ID NO: 8)

-continued

Sequences

Figure 39:
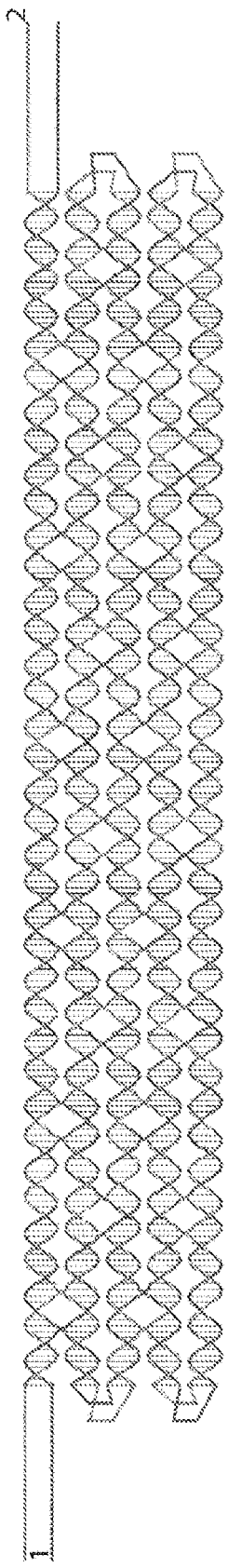
FIG. 39 shows the design detail of a strip-shape ssDNA nanostructure. The black strand is the forward strand and gray strand is the reverse strand.

Strip-shape ssDNA (FIG. 39)
Forward strand:
TACGGCACGTAAGCCTTGCATTGACTAGCCAACGTTTTGTGCCACGGCGCTATTGTGTCGTCGGTACACTCGAGAC
GTCGCCACCTAGAGCTTGGAAGGTATCTTGTACACAGCGTACCGCTGAAGGCGATCGTAAGGCCGAACAGTTATAC
GGTGTATTCATTATCCGATAACGAGCGTTTGAACCAGGCAGTTGTAAGGGTTCTCAATTGTTACGTAGCTTCGGCG
TCCGTTTTTTTGCAAATAGCGAGCTACCAGTCGTAGCACCGATAGCGCGACTGGGGCAGTGCTGACGCGACATAAA
CACCTTGCGCTTTCGTTACGTTTTCTCGGCCATGTCTGACAACTAGGCGGACTACACATGGAATTTAGTAAATGGC
ATCCTGAAGGCGAAATACCGCCGTCCAGTGACGACCTTGATACTAGGTCGACCTCATGAGCTTTTTTTCAGTTATC
TAGACTCAATCACCAAATATTGAGACGACCCTGCTCTAATCTTCCCGCGGTTGCATGGATCGTAGGTTCCATCACG
GTTAATGTAAGGGTAACCCTTCGAAACTGAGTCGGTTTAGTTGCGGCTCCCTCCTACTCTAAACCGGCGCCTGCCC
CATTAGCGTGATGCCGGCGTCACCAGCATCTAGTCCCTCGTCTTTTTTTGGGTGGGTCTTAGATGGGCGCGTCAAT
TCTGGAACCCAAGCAAAATGCAGCCAGAACTGTTATCGATTGTCAGCATAGTTAGACTAGGCAAGTTTCTCCGTAG
TTACCATAGGCAAAATAAAGGATAATGTGGCCCTCCAAGCTGTTGGGATAATTTCGCACATTTTAGGCTCAATTTC
GCGGGTAATTAGAGCAGCTTGGCTTTTTTTGCACAGCCGTACCACCACACTCCGTGCGTCTGATCCCGCTTGGGTA
TTAGGGCCGACTGTTTTTGGGCTACAAGTTATCCTGATTTATCAGAGCAGAAGTTTATGAGTCGCAAGGTTGTTTC
CGAAAGCGATTACCGCTCGAACCCCCGGGACGGCATTTTGCGGTGTTTACGCACCCATGTCTTTCGAAGCCCACTG
AGAAACAGCGACTAGATAATCGACCGCGTCCCAT (SEQ ID NO: 9)

Reverse strand:
ACAGCGACTAGATAATCGACCGCGTCCCATTTCTCAGTGGGCTTCGAAAGACATGGAGAACCAAACACCGCAGGCG
TACGTCCCGGGGAGAGTAGCGGTAATCGCAAATAGAAACAACCTTGCGACTCATAAACTTCTTCAGTGATAAATCA
TCCGCCCTTGTAGCCCATGCAAAGTCGGCCCTCATCTTCAAGCGGGATCAGACGCACGGAGTGTCGTGGCACGGCT
GTGCTTTTTTTGCCAAGCTGCTCGACCTACCCGCGAATAGGAGCCTAAAATGTGCGAAATTATCCCAACCGCTGCG
AGGGCCACAGGCGGATTTATTTTGCCCTAGTTAACTACGGACGGATATGCCTAGTCTAACTATGCTGACAATCTGC
TCGAGTTCTGGCTTACGCCTGCTTGGGTTATCGGTTTGACGCGCCAGTATTAGACCCACCCTTTTTTTGACGAGGG
ACAATACTCTGGTGACGCCGGCATCACGCTAATGAACATGGCGCCGGTTTGTTGAGGAGGGAGCCTACACCAAAC
CGACTCTATCCGGAAGGGTTACCCTTACATTAACCGTGTGCTAGCCTACGATCCAAAAACCCGCGGGAAGACGTCT
GCAGGGTCGTCTCCTAATTTGGTGATTGAGTCTAGATAACTGTTTTTTTGCTCATGAGGTCTAATTAGTATCAAGA
ATAGTACTGGACGGCAAGATGTCGCCTTCAGGATGCCATTTACTAAACTAGCAGTGTAGTCCGCTATGGTGTCAGA
CATCTTATTGAAAACGTAATATTTGCGCAAGGTGTTTATGTCGCGTCAGCACATGTTCAGTCGCGCTCCAGAAGCT
ACGACTGGATACGCGCTATTTGCTTTTTTTCGGACGCCGACGTATCGTAACAATTGGTGCGTCTTACAACTGCCTG
GTTCAAACGCTCCGAGCAGGATAATGAAGCAACTGTATAACTGTAATAAGTTACGATCGCCTGCTCCGGTACGCTG
TGTACAAGATACCTTCGCAGCGCTAGGTGGCGATTAGACGAGTGTACCACTATTACAATAGCGCGGTGGTACAAAA
CGTTATCCGGCATCGCGATTCATCTTCGCGAATC (SEQ ID NO: 10)

Figure 40:
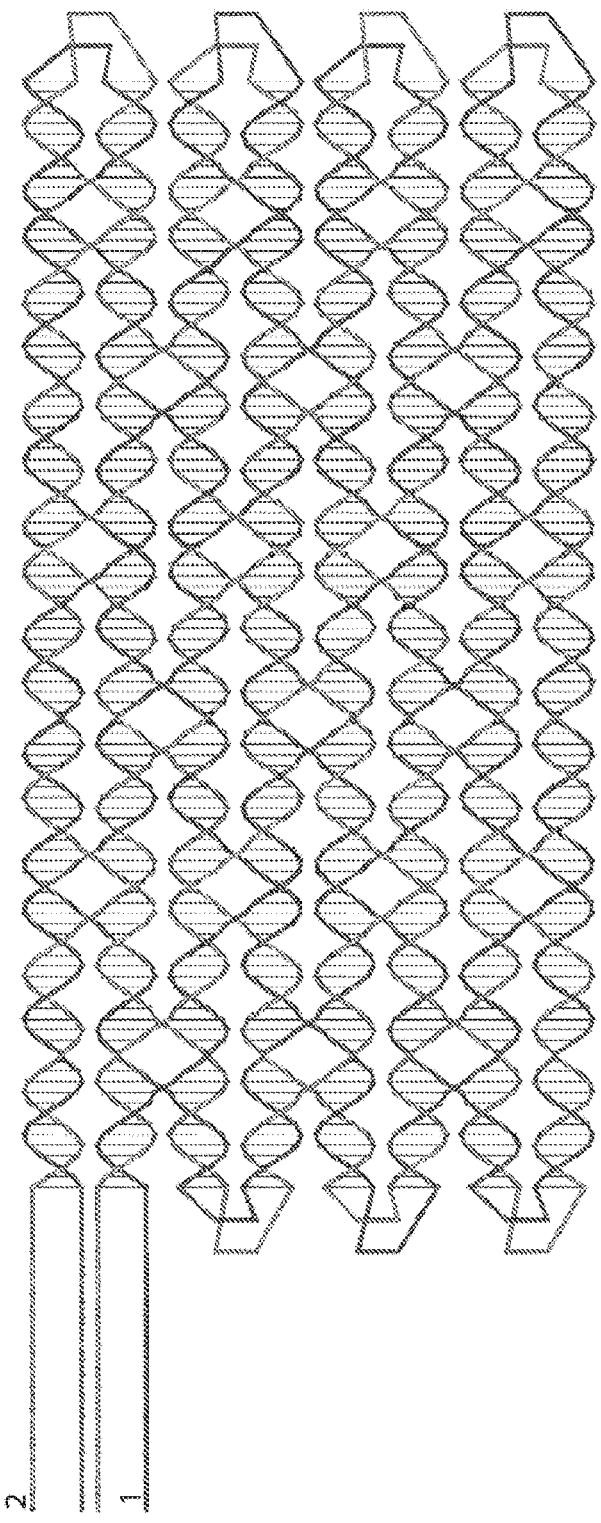
FIG. 40 shows the design detail of a rectangle-shape ssDNA nanostructure. The black strand is the forward strand and gray strand is the reverse strand.

Rectangle-shape ssDNA (FIG. 40)
Forward strand:
TACGGCACGTAAGCCTTGCATTGACTAGCCAGTAGTGTAACCCGTAATGACCCAGCCTATTATCGTCTCAGTCTGC
TGGGAGGTCAACCTCTGCGCTCTATAGAGTGGTAAAATGGCTCCGGACAGTGGAGTCAGCTTTTTTTCAAAACCTG
CCTGTCCGCCTACTCTCAAGTTCGAATGCAGGGATTATAGGATCGTTGAGATAGGGGGGTGGAGGCTATCTCAGTG
TGCTCTACGACATCAGTTATTTTTTTTCCATAAACCAGACGGGAAGGAGCGTATCAGAAGTGGGACCTCCTTACT
ATGCAACGCGCTGGTCAAAATTAGACTATCAGTAACCCAAGAATTTGTACTCCAAACTTTTTTTGAATCTCCACC
AAATTCCATGCCATGCGAGATCAATCTTAACGCAGAGCCACTCGGCTGAGTGTGAACGTGACTTGCCTAGACTGTA
TCGCTTTCCGGTTTTAGACTTTTTTTAGGCTAAAGCCGATCATCCTCCGGGGAGATAGCACGTGGCTGATTACAAT
TAGTAACGTCTTATCTAGAGCACTGCGACATATGAAGCGACAGATACTTGAGACGTTTTTTTGGGTGAATCTATC
TGCCGCGCTGTTATGTATGTATCGCCGGTGACCAGACGTAGAAGATTGGCCGAATGCATATAATAGAAAAGTAAG
TCCATACTTATATAATATTTTTTTTGCCTTGCTACTTACCAGGAATAACTAGGCAAATGTTAGGTACCTAATCGT
TCTAGCTATAATGCCAGTACTACTGATTCGGTTAGAGTGTAGGGCCTCCAAGCTTTTTTTTCCGGTCTTACCCTA
CAGCGCTGGACCTGCTCACCCGACCCCATAAGAAAGCCTTTTGTGGACATGCCACCCGGTTCTGATGGCGGCGCCT
GCTCCCTCAGCCATGACAGCGACTAGATAATCGACCGCGTCCCAT (SEQ ID NO: 11)

Reverse strand:
ACAGCGACTAGATAATCGACCGCGTCCCATCATGGCTGAGGGAGCAGGCGCCGCCACTTAAACCGGGTGGCAGCCA
ATCAAAAGGCTTTAAAAGGGGGTCGGGTATCTCGGTCCAGCGCTCTATTTTAAGACCGGATTTTTTTAGCTTGGAG
GAAATAGACTCTAACCGTACCACTAGTACTGGCTAAATAGCTAGAACGATTAGGTACCTAACATTAATTTCGTTAT
TCCTGTGATCGAGCAAGGCAATTTTTTTTATTATATAAGTCGTAACTTACTTTTTAATCGTATGCATTCGTGTCCA
CTTCTACGCTAGACCCACCGGCGATACATACATAACAGCGCGGGGCGGAGATTCACCCTTTTTTCGTCTCAAGTC
CGCCCTCGCTTCATATGATAGAGTGCTCTAGCTTTTACGTTACTAATCAGCAGCAGCCACGTGCCCGACCCCCGGA
GGAGTAAGTGCTTTAGCCTTTTTTTTGTCTAAAACCGGAAAGCGATACAGTCGAAATTAGTCACGTTCCCTATCAG
CCGAGTGGCTAGGCGTTAAGATTGGAGCAGCATGGCATGGCAGCACGTGGAGATTCTTTTTTTGTTTGGAGTAGTG
CTGCTTGGGTTACTGTCGCTCTAATTTTGGGGTCTCGCGTTGCATAGTAAGGAGGTCCCACTTTAAGTACGCTCCT
TTACGGGTGGTTTATGGTTTTTTTAATAACTGATGTATGGGAGCACACTGGTCGGGCTCCACCCCACACTCTCAA
CGATCCTATTTACCCTGCATTCGAACTTGAGAGTAGGCTGAGAAGCAGGTTTTGTTTTTTGCTGACTCCATTCTC
AGGAGCCATTTAATCAGTCTATAGAGCGCCTAGGTTGACCTCCTGTAATACTGAGACGACGATTAGCTGGGTCATC
CCGTCTTACACTACTATCCGGCATCGCGATTCATCTTCGCGAATC (SEQ ID NO: 12)

Figure 41:
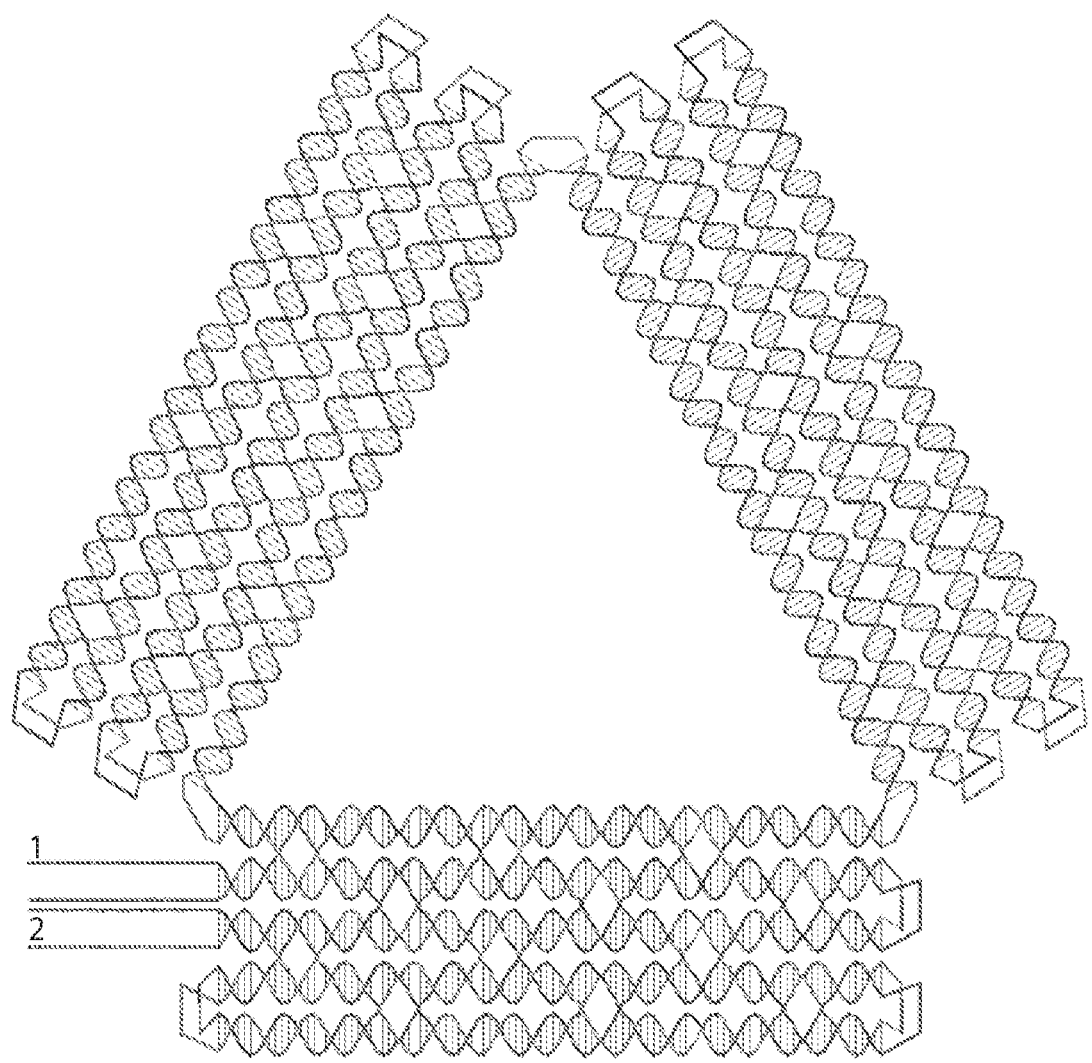
FIG. 41 shows the design detail of a triangle-shape ssDNA nanostructure. The black strand is the forward strand and gray strand is the reverse strand.

Triangle-shape ssDNA (FIG. 41)
Forward strand:
TACGGCACGTAAGCCTTGCATTGACTAGCCAAAGTGGACGGTCTTTAGGTTCACAACTTGTTGGCCGATAGGCCAC
ACAGATGTTCTAGGGCACAAGGACGCAAAGCGGAATTGGGTGTAAGCCGGTCGGTTCGACTTTATTTATTTTACAG
CTTTACCGGCTTGATACGGCCGGAGCTCCAGTGCTCCTACTTACAATGCATAGTCGGATTTTCTTAACGGAGTGTT
TTTAGAAGGAAAGACATTAGAGTCGAGCTAGTTAAATAGGACGCAATCACCGAGGGCATAGGTTATCGCCTACTTT
CGTGCCGAGATGGTCGCATGAAAGTGCCTGCTGAACTGATTCAGATGGTCTGGGTTTTATTTATTTCCGAGGCTGG
AGCGTGAACAGCGTAAACTGGTTGATACCTCTTCGACTATCTAACCTTAGAAATTTCCACTCCGCCCTCGCTTTT
GCCATCTGTAGCCTTAGGCTTTTATTTATTTGCATAACTTGTACAGAAACCATTACTGCTGTAGTTTTCATGGGAC
GCTTAGGTCTGGCAGTCGGGCGCCCTGAGCTATCACATTACGAGACACGCTGATGGCATCCTTTATTTATTTCCTC
ATCTATCCACAAGTCAACGCCACTGAATGAAACTTCACCATGGATAAAATGGATGTAGGCGATCCGCAAGTACAGC -continued

| Sequences |
|---|
| CCCCGGCCCCTGCGACGTGTTTTTTGTTTATTTATTTTCGAAAATTTGTCGCATCCCCGCGAGATGTGTTAAATCT<br>AGCGGTCGGGAGCTTATATGTCAAACTAGCAATCTACCAGTTCAGTTTTTGTTGTGGGAAGGGATTCTAAGTCTGT<br>GCCTCGATCATATTTAGCAGATAGATAAGTCCGCCGAGCAAGCTGACAGTTTAGCAACTATGAGCGGACTCGTGGG<br>TATAGGATCGGACAAGAATTCTTTATTTATTTGAGTGTATCTAGAGTCTCGGTCCGGCAGCTCCTTCTATGTCGTC<br>TACCAGCTCACGCTGGTATAAACCATGGATTATCTGGCAATTCGCGCGCAAGGCAACTCGGTTTATTTATTTGAA<br>CGCTCGCTTGGCGCACCTCCCGCTCAAATCTGACCCGCGGGAAGATTTACCGGCCCTCTAGGTGGTGATCTAGAGC<br>GATAAAAACCGGACTCTTCCTGAAGAGTTTATTTATTTTCTATATCTACGATTTGAATCTGAGCCTACTCTGTAAC<br>GTGATGATGACTCGAGCCTGGCTCGGAATGTGTATAATTTGACAGATGATTCTGTGACAAGTTACGGGTTTATTTA<br>TTTTAGCATCGCGGTCACAGCACCGTCCCTGACATCTCATTATTTCCAGTGAGAGGAAGAACGTCTAGAACTTGCA<br>AGGAGCTACTCCCCCTCAAATCGCTGGGAGTCCTGTAATCGATAGTTGACCAGGATTAAACGAGATAAAGGCCCTG<br>TGCCCACCCCTAGGGCGAGTAGAACAACGTCGAGCATACTCACTAATATGGGCGCAGTGAAGTTTATTTATTTTA<br>CTGGAAATTAAGAGGCCACAATGCACACTCATGAACCCGAGGGGGTCCTTTTTGGTCTGTGGTAGTTATGTATCTC<br>GTCAACTCAAATAACTTAAGTACGGAAATTTATTTATTTCACTCTGAGATAAGTTTCCGGCTTGATCCGCTATATT<br>TAACCAACTTAGGGGCTGAAAGAGGAATACCCAATGTTCCTTATTCGATTGATCTCTTATTGTTCGAGAACAGCGA<br>CTAGATAATCGACCGCGTCCCAT (SEQ ID NO: 13) |
| Reverse strand:<br>ACAGCGACTAGATAATCGACCGCGTCCCATTCTCGAACAATGTGCCATCAATCGAAATGCTCACATTGGCTATTCC<br>TCTTTCAGCCCCTAAGTAGGTTAAATATGCATTATCAAGCCGGATAAACGTCTCAGAGTGTTTATTTATTTTTTCC<br>GTACTCGTTTAATTTGAGTTGTTCCCATACATAACTACCACAGACCAAAAGGGTGTGGTCGGGTTCATATATAGG<br>CATTGTGGCGGCACAATTTCCAGTATTTATTTATTTCTTCACTGCCGCCCATATTAGTGAGTTAAGGAGACGTTGT<br>TCATCCGACCCTAGGGGTGAGGGTAGGGCCTTTATGGGAATTAATCCTGGTCAACTATCGATTACATTTATTTATT<br>TGGACTCCAGCGCCCAGAGGGGAGTCAGAAGTTGCAAGTTCGCTAAATTCTTCCTCTTCTTCCAAATAATGAGA<br>TGTCAGGGACGGTGCACGTACCGCGATGCTATTTATTTATTTCCCGTAACTTGTACGTGAATCATCTGCACCAATA<br>TACACATTGTTCCTCAGGCTCGAGGGTAGATCACGTTACAGAGTAGGCTCAGATTCTGGGCGTAGATATAGATTTA<br>TTTATTTCTCTTCAGGGAATCTCACGGTTTTTATGAGTCCAGATCACCACCTAGGGCCGGTAAACACTGGCGCGG<br>GTCAGTTGGTGGCGGGAGGTGACAGTCGCGAGCGTTCTTTATTTATTTCCGAGTTGCCGACTGTCGCGAATTGCAA<br>ATTAATCCATGGTTTATACCAGCGTGAGCTTCATCACGACATAGAACTTCTGGCCGGACCGATGAGATAGATACAC<br>TCTTTATTTATTTGAATTCTTGTCCGATCCTATACCCACCGCTCTGCTCATAGTTTAGACGCTGTCAGCTTAGGAA<br>CCGGACTTATCTAATTTCTAAATATGATCGAGGCACAGACTTATTTATTTATTTGAATCCCTTCCCTCTGCAAAAA<br>CTGATCTTCAAGATTGCTAGCCATCTATATAAGCTCAGCGTCGCTAGATTTAACACATCTCGCGGGGAGAAACAAA<br>ATTTTCGATTTATTTATTTCAAAAAACACTGTTTCGGGGCCGGGAGGGTGCTTGCGGATCCCCACGATCCATTTT<br>AAGTCGAGTGAAGTTTCATTCAGTGGCGTTGACCAGAGGATAGATGAGGTTTATTTATTTGGATGCCATCGCGATT<br>TCTCGTAATGAGGCACCTCAGGGCGCCCGACTGCCAGACCTACCGACCCATGAAAACCACCCTAGTAATGGTTTG<br>TTCTCAAGTTATGCTTTATTTATTTAGCCTAAGGCAGAACATGGCAAAAGCACGTCCGGAGTGGAAATTTCTAAGG<br>TTAGTATTCCATGAGAGGTATCATGAAGATTACGCTGTTAATCGCCCAGCCTCGGTTTATTTATTTACCCAGACCA<br>TCTGAATCAGTTCAGCTGATAGTTTCATGCGATTTGACCGGCACGAAACGTGGGGATAACCTATGGACGTGGTGAT<br>TGCGTCCTATTTAACTAGCTTTTATTTATTTCGACTCTAATTTTTCGCCTTCTAAAACTATATCGTTAAGAAATAC<br>TCGCTATGCATTGTAAGTTGGAGCACTGGAGCTCCGCCGTATCACCCCGATAAAGCTGTATTTATTTATTTGTCG<br>AACCGATCGGGGTACACCCAATTAATGCTTGCGTCCTTACCCTCTAGAACATCTACCCCCCCATCGGCCAACAAG<br>TTGTGAACCTCGAAAACGTCCACTTTATCCGGCATCGCGATTCATCTTCGCGAATC (SEQ ID NO: 14) |

TABLE 2

Figure 42:
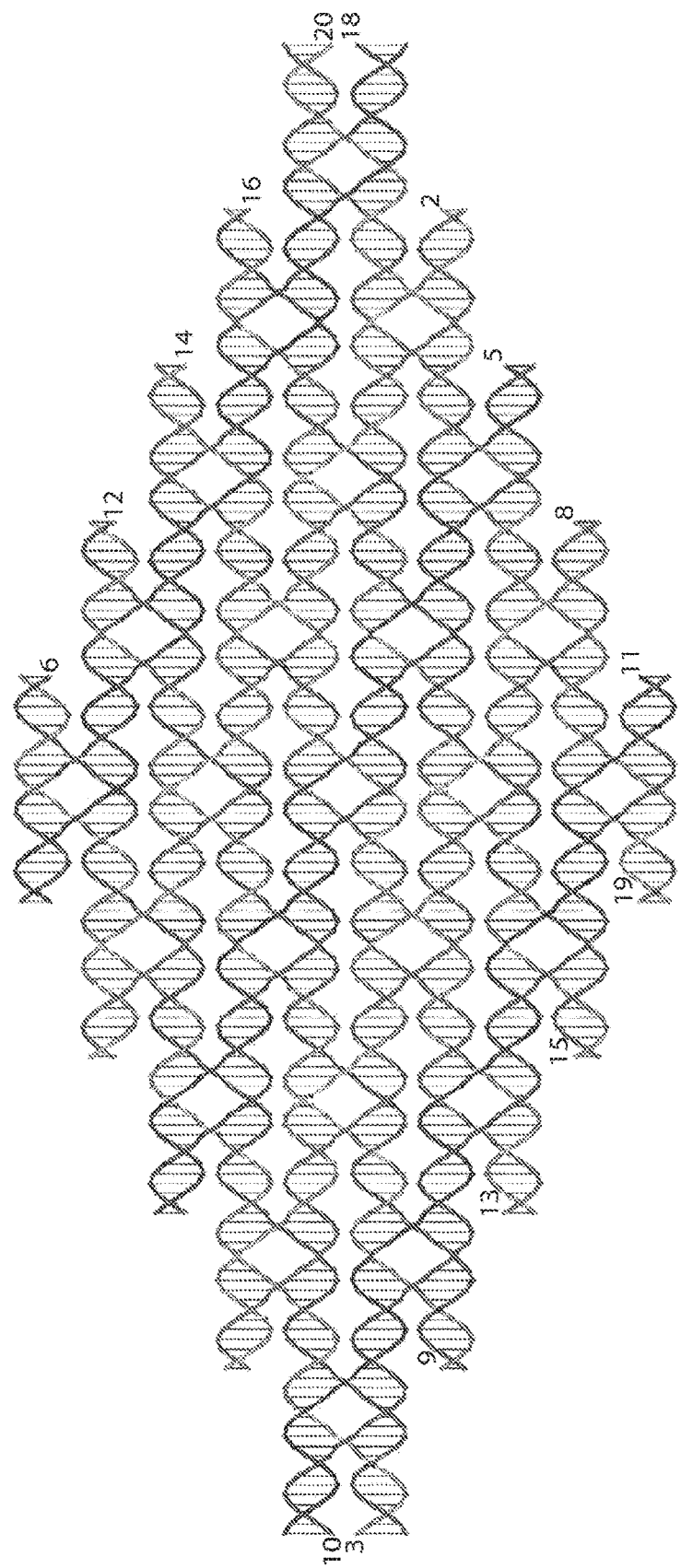
FIG. 42 shows the design detail of a 20-strand version of a 5×5 diamond-shape ssDNA nanostructure.

20-Strand version of 5 × 5 diamond-shape ssDNA (FIG. 42)

| Strand No. | Sequence | SEQ ID NO: |
|---|---|---|
| 1 | CGGTCGTCACCAATATCGTAATTGAGCCAACCTCAACGCGGGTCCGATGCGGCAT<br>GAGGCTGACACGCCATGGCAGGCATCGATTGGG | 15 |
| 2 | CCCAATCGACTGAAGCCATGGCGTGCCATACTCATGCCGCAATCTATCCGCGTTG<br>AGTTAGCATCAATTACGATGAAACTGACGACCG | 16 |
| 3 | AAACAGATCGCACTCAGCGGTCTCGTAGATCGAGTGTCTCTACCTGAGACAAGGA<br>TCTGTTTCACAAGGCCTTGTGACTTCCGCTAGTC | 17 |
| 4 | CCTCGAAGTGATTGATCTAGCGTAGGCTCTACCGTTCGGCTCGCCCTCTGCAACA<br>TGAAGATCGGTCGCCAAGCACCGATGTCGGTCC | 18 |
| 5 | GGACCGACAGGTTGTCTTGGCGACCTCGTCCCATGTTGCAGAGTGTGAGCCGAAC<br>GGAAATAACTACGCTAGACTCAGGACTTCGAGG | 19 |
| 6 | GACTAGCGGAAATGGCAAGGCCTTGTATTGGAGATCCTTGTTCAATCTAGAGACA<br>CTCGCGCCACGAGACCGCAGAGCACGATCTGTTT | 20 |
| 7 | CCGGCTGTGGGCGCGAGGTGCCGTGGCGTCTGCAAGACACAGCGCTCTGTTGATA<br>TCGCCCAGGTCTACGACAGTTGAGTGTTGGGCG | 21 |
| 8 | CGCCCAACACTGGGTTGTCGTAGACAAAATCGATATCAACAATAAGGTGTGTCTT<br>GCCCAGTACACGGCACCTCGATCTCACAGCCGG | 22 |
| 9 | TCATAGTAAAGACGTCAGGATAGAATACTGGGAAGATGCCATTATTTCCCATATG<br>TTTGCTAATCGTGGACTCCACGTCATGGCAGCC | 23 |

TABLE 2-continued

20-Strand version of 5 x 5 diamond-shape ssDNA (FIG. 42)

| Strand No. | Sequence | SEQ ID NO: |
|---|---|---|
| 10 | CAGGATCTAGTGCTCTATGGGATTAGGTCTAGGACCTTCCGGCGGGTCGGTTTGT GCATACCAGATGTTAACGTGACCGGCAGTCAAGT | 24 |
| 11 | ACTTGACTGAGGCACACGTTAACATTCGCATTGCACAAACCCACACACCGGAAGG TCACGTCTCTAATCCCATTGAGTGCTAGATCCTG | 25 |
| 12 | GGCTGCCATGAGACCGAGTCCACGAGTTGGCAACATATGGGTAGAGCTGGCATCT TCAGACGCTTCTATCCTGCTAGACTTACTATGA | 26 |
| 13 | CAGATCATCTGTGTGTGGCCGGATGCCTTATCGGGTCTCGTCACACTCGGGCACA GAATAGATCTCTAAGAGACACGTGCCCAAAGCG | 27 |
| 14 | CGCTTTGGGCCACGCTCTCTTAGAGTCGGACTCTGTGCCCGAGGGCGACGAGACC CGGAGCGCCATCCGGCCAGACCCGGATGATCTG | 28 |
| 15 | GGGACGTGCATGCGACCCACGTCGTGATTTTGTTCCACTTGGGACGAATGTCGAA GTGTATGGTGCATTACCCGTAGGCTACATCTGG | 29 |
| 16 | CCAGATGTAAGTTTTGGGTAATGCATCAGCCACTTCGACATGATCTTCAAGTGGA ACCTGGGCACGACGTGGGCTGGTAGCACGTCCC | 30 |
| 17 | CTGATAGGCCCATTTCTAATTTCGCGGTCTCTTACACGGGTGCGTGGTCTTCCTC TGAAAACTGGAGCCACAGGGAGGGACACTCGCTT | 31 |
| 18 | AAGCGAGTGTCGGCATCTGTGGCTCCGCCTACCAGAGGAAGACACGTGACCCGTG TAAGACGTGGCGAAATTAGAAGTCAGCCTATCAG | 32 |
| 19 | CAGGCTCGTGTGCCTTGGAGATGGAACCCAGCTGGAGCGAGACAACCAGATGGGA TCCTTCAGCCCATGACAAATGCCGCACAGGCAGC | 33 |
| 20 | GCTGCCTGTGCCCTCCTTGTCATGGGTGCCTGGATCCCATCTTCGGTGCTCGCTC CAGCTCAACTCCATCTCCACCGGTCACGAGCCTG | 34 |

What is claimed is:

1. A nanostructure formed from a single strand of DNA, wherein the nanostructure comprises:
   a first layer containing helical domains and locking domains, wherein at least two helical domains of the first layer are separated from each other by a locking domain;
   a second layer comprising helical domains and locking domains, wherein at least two helical domains of the second layer are separated from each other by a locking domain; and
   loop domains that connect one helical domain to another helical domain and are located along the periphery of the nanostructure,
   wherein a locking domain of the first layer is hybridized to a locking domain of the second layer.

2. The nanostructure of claim 1, wherein the single strand of DNA has a length of 500 nucleotides to 10,000 nucleotides.

3. The nanostructure of claim 2, wherein the single strand of DNA has a length of 2,000 nucleotides to 5,000 nucleotides.

4. The nanostructure of claim 1, wherein the helical domains have a length of 10 to 50 nucleotides.

5. The nanostructure of claim 4, wherein the helical domains have a length of 10 to 30 nucleotides.

6. The nanostructure of claim 1, wherein the locking domains have a length of 4 to 20 nucleotides.

7. The nanostructure of claim 6, wherein the locking domains have a length of 5 to 10 nucleotides.

8. The nanostructure of claim 1, wherein the loop domains have a length of 10 to 100 nucleotides.

9. The nanostructure of claim 8, wherein the loop domains have a length of 10 to 50 nucleotides.

10. The nanostructure of claim 9, wherein the loop domains have a length of 20 nucleotides.

11. The nanostructure of claim 1, wherein the crossing number of the nanostructure is zero and the nanostructure is unknotted.

12. The nanostructure of claim 1, wherein the nanostructure contains only parallel crossovers.

13. The nanostructure of claim 1, wherein the nanostructure contains continuous $\pi$-$\pi$ stacking along greater than 50% of the helical domains of the nanostructure.

14. A method of producing the nanostructure of claim 1, the method comprising incubating the single strand of DNA under conditions that result in the formation of the nanostructure.

15. A method of producing the nanostructure of claim 1, the method comprising:
   (a) combining in a single reaction mixture
      (i) a first DNA template and a second DNA template, wherein the templates comprise end sequences that overlap with each other,
      (ii) a first primer having a phosphorothioate modification, wherein the first primer binds to the end of the first DNA template that is opposite to the overlapping end sequences,
      (iii) a second primer having a phosphate modification, wherein the second primer binds to the end of the second DNA template that is opposite to the overlapping end sequences, and
      (iv) polymerase;
   (b) performing on the single reaction mixture a nucleic acid amplification reaction, thereby producing amplified DNA;
   (c) exposing the amplified DNA to exonuclease digestion, thereby producing a single strand of DNA; and
   (d) heating the single strand of DNA to a temperature of 85° C. to 95° C., and then progressively cooling the single strand of DNA to a temperature of 20° C. to 37° C., thereby producing the nanostructure.

* * * * *